(12) United States Patent
Hell et al.

(10) Patent No.: US 12,174,197 B2
(45) Date of Patent: Dec. 24, 2024

(54) SULFONATED 2(7)-AMINOACRIDONE AND 1-AMINOPYRENE DYES AND THEIR USE AS FLUORESCENT TAGS, IN PARTICULAR FOR CARBOHYDRATE ANALYSIS

(71) Applicant: Max-Planck-Gesellschaft zur Foerderung der Wissenschaften e. V., Munich (DE)

(72) Inventors: Stefan W. Hell, Goettingen (DE); Vladimir N. Belov, Goettingen (DE); Matthias Bischoff, Dortmund (DE); Dirk Meineke, Cologne (DE); Laura Thomas, Wustrow (DE); Gyuzel Mitronova, Goettingen (DE); Elizaveta Savicheva, Goettingen (DE); Kirill Kolmakov, Magdeburg (DE); Marvin J. Boehm, Uslar (DE); Erdmann Rapp, Magdeburg (DE); René Hennig, Magdeburg (DE)

(73) Assignee: Max-Planck-Gesellschaft zur Foerderung der Wissenschaften e. V., Munich (DE)

( * ) Notice: Subject to any disclaimer, the term of this patent is extended or adjusted under 35 U.S.C. 154(b) by 743 days.

(21) Appl. No.: 17/424,415

(22) PCT Filed: Jan. 21, 2019

(86) PCT No.: PCT/EP2019/051396
§ 371 (c)(1),
(2) Date: Jul. 20, 2021

(87) PCT Pub. No.: WO2020/151804
PCT Pub. Date: Jul. 30, 2020

(65) Prior Publication Data
US 2022/0107325 A1 Apr. 7, 2022

(51) Int. Cl.
*C09B 15/00* (2006.01)
*C09B 57/00* (2006.01)
*G01N 33/58* (2006.01)

(52) U.S. Cl.
CPC .......... *G01N 33/582* (2013.01); *C09B 15/00* (2013.01); *C09B 57/001* (2013.01); *G01N 2400/10* (2013.01)

(58) Field of Classification Search
CPC .. G01N 33/582; G01N 2400/10; C09B 15/00; C09B 57/001; C07C 2603/50;
(Continued)

(56) References Cited

U.S. PATENT DOCUMENTS 5,472,582 A 12/1995 Jackson
6,706,879 B2 * 3/2004 Anderson ............... C09B 23/06
546/88
(Continued)

FOREIGN PATENT DOCUMENTS

DE 102018124199 A1 4/2020
WO 9005916 A1 5/1990
(Continued)

OTHER PUBLICATIONS

STIC Search Report dated Apr. 22, 2024.*
(Continued)

*Primary Examiner* — Eisa B Elhilo
(74) *Attorney, Agent, or Firm* — CAESAR RIVISE, PC

(57) ABSTRACT

Sulfonated 2(7)-aminoacridone and 1-aminopyrene dyes and their use as fluorescent tags, in particular for carbohydrate analysis The invention relates to fluorescent dyes with multiple negatively charged groups in their ionized form which are aminoacridone sulfonamides or 1-aminopyrenes having of one of the following general formulae A-D:
(Continued)

Formula (A), Formula (B), Formula (C), Formula (D), wherein the ionizable groups X are typically selected from the following: SH, COOH, $SO_3H$, $OSO_3H$, $OP(O)(OH)_2$, $OP(O)(OH)R^a$, $P(O)(OH)_2$, $P(O)(OH)R^a$, where $R^a = C_1$-$C_4$alkyl or substituted $C_1$-$C_4$alkyl. The invention further relates to the use of these dyes as fluorescent tags, in particular for reducing sugars and glycans.

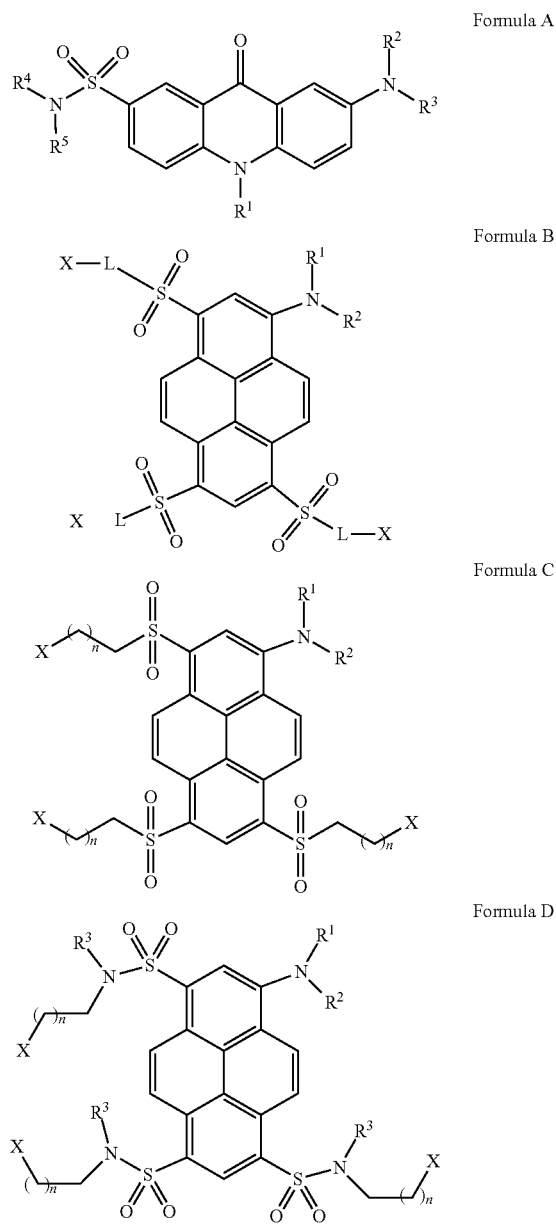

Formula A

Formula B

Formula C

Formula D

20 Claims, 3 Drawing Sheets

(58) Field of Classification Search
CPC ... C07C 317/36; C07C 317/40; C07C 311/40; C07H 1/00; C07H 15/18; C07D 219/08; C07F 9/3808; C07F 9/64; C07F 9/6561

USPC .................................................. 8/648
See application file for complete search history.

(56) References Cited

U.S. PATENT DOCUMENTS

| 8,506,655 B1* | 8/2013 | Li ..................... C09B 69/103 8/633 |
| 2011/0097734 A1* | 4/2011 | Feaster ............ G01N 33/54388 435/7.1 |
| 2011/0097735 A1 | 4/2011 | Mao et al. |
| 2021/0373028 A1 | 12/2021 | Berndt et al. |

FOREIGN PATENT DOCUMENTS

| WO | WO 9005916 A * | 5/1990 | .......... C07C 309/86 |
| WO | 9211531 A1 | 7/1992 | |
| WO | 2009112791 A1 | 9/2009 | |
| WO | WO 2012027717 A2 * | 3/2012 | .......... C07C 311/39 |
| WO | WO 2013033046 A2 * | 3/2013 | .......... C07C 311/32 |
| WO | WO 2016090076 A2 * | 6/2016 | .......... C07D 311/84 |
| WO | 2020069945 A1 | 4/2020 | |

OTHER PUBLICATIONS

Singapore Search Report dated Apr. 3, 2023.
Office Action re EP 19 701 605.8 dated Mar. 28, 2024.
Anumula. (2012). New high-performance liquid chromatography assay for glycosyltransferases based on derivatization with anthranilic acid and fluorescence detection. Glycobiology, 22(7), 912-917.
Bigge et al. (1995). Nonselective and efficient fluorescent labeling of glycans using 2-amino benzamide and anthranilic acid. Analytical Biochemistry, 230, 229-238.
Blazquez et al. (2006). Acridone heterocycles as fluorescent sensors for anions. Heterocycles, 69, 73-81.
Borch et al. (1969). Lithium Cyanohydridoborate, a Versatile New Reagent. Journal of the American Chemical Society, 91, 3996-3997.
Greene. (1999). Protective groups in organic synthesis, p. 557.
Hennig et al. (2011). Glycoconjugate J.,28, p. 331.
Kolmakov et al. (2012). Red-emitting rhodamines with hydroxylated, sulfonated, and phosphorylated dye residues and their use in fluorescence nanoscopy. Chem. Eur. J., 18, 12986-12998.
Kolmakov et al. (2014). Polar red-emitting rhodamine dyes with reactive groups: synthesis, photophysical properties, and two-Color STED nanoscopy applications. Chem. Eur. J., 20, 146-157.
Li et al. (1994). Synthesis and characterization of functionalized analogs of 1,3,6,8-tetrakis(methylsulfanyl)pyrene and their electron-conducting radical-cation salts. J. Am. Chem. Soc., 116, 9890-9893.
Mispelaere-Canivet et al. (2005). Pd2(dba)3/Xantphos-catalyzed cross-coupling of thiols and aryl bromides/triflates. Tetrahedron, 61, 5253-5259.
Riekkola et al. (2004). Terminology for analytical capillary electromigration techniques. Pure Appl. Chem, 76(2), 443-451.
Ruhaak et al. (2010). Optimized workflow for preparation of APTS-labeled N-Glycans allowing high-throughput analysis of human plasma glycomes using 48-channel multiplexed CGE-LIF. Journal of Proteome Research, 9, 6655-6664.
Sharrett et al. (2009). Exploring the use of APTS as a fluorescent reporter dye for continuous glucose sensing. Org. Biomol. Chem., 7, 1461-1470.
Shilova et al. (2003). Fluorescent labels for the analysis of mono- and oligosaccharides. Russian Journal of Bioorganic Chemistry, 29(4), 309-324. Translated from Bioorganicheskaya Khimiya, vol. 29, No. 4, 2003, pp. 339-355.
Volpi et al. (2011). Capillary electrophoresis of carbohydrates, From monosaccharides to complex polysaccharides, Humana Press, 1-51.
Xu et al. (2010). Synthesis and crystal structure of novel sulfone derivatives containing 1,2,4-triazole moieties. Molecules, (2010), 15, 766-779.
Anumula. "Advances in fluorescence derivatization methods for high-performance liquid chromatographic analysis of glycoprotein carbohydrates." Analytical biochemistry 350, No. 1 (2006): 1-23.

(56) References Cited

OTHER PUBLICATIONS

CAS Registry No. 1360684-35-0; STN Entry Date Mar. 13, 2012.
CAS Registry No. 131539-59-8 (1990).
CAS Registry No. 1360595-18-1; STN Entry Date Mar. 12, 2012.
CAS Registry No. 1360684-33-8; STN Entry Date Mar. 13, 2012.
CAS Registry No. 1360684-34-9; STN Entry Date Mar. 13, 2012.
Australian Examination Report dated Oct. 26, 2022.
Translation of Japanese Office Action dated Oct. 5, 2022.

* cited by examiner

SULFONATED 2(7)-AMINOACRIDONE AND 1-AMINOPYRENE DYES AND THEIR USE AS FLUORESCENT TAGS, IN PARTICULAR FOR CARBOHYDRATE ANALYSIS

CROSS-REFERENCE TO RELATED APPLICATIONS

This application is a U.S. National Phase Application of PCT/EP2019/051396, filed Jan. 21, 2019, the contents of which are incorporated herein by reference in their entireties for all purposes.

BACKGROUND OF THE INVENTION

The present invention relates to fluorescent dye compounds which provide novel efficient and advantageous tags for carbohydrate analysis, particularly in those methods that involve reductive amination, followed by chromatographic or electrokinetic separation and fluorescence detection by means of hydrophilic interaction chromatography with fluorescence detection (HILIC-FLR, reversed phase liquid chromatography with fluorescence detection (RPLC-FLR), capillary (gel) electrophoresis with laser-induced fluorescence detection (CE-LIF, respectively CGE-LIF) or other separation based glycoanalytical methods. Chromatographic methods can be operated as high performance or as ultra-high-performance liquid chromatography (HPLC or UHPLC) and all separation-based methods can be coupled to mass-spectrometry, either alternatively or in addition to fluorescence detection. Characteristically, the fluorescent maxima of the dye-carbohydrate conjugates are considerably shifted to the red, relative to that with known dye tags (considered below).

The term "carbohydrate(s)" as used herein is the collective term for monosaccharide(s), like xylose arabinose, glucose, galactose, mannose, fructose, fucose, N-acetylglucoseamine, sialic acids; (homo or hetero) disaccharide(s), like lactose, sucrose, maltose, cellobiose; (homo or hetero) oligosaccharide(s), like glycans (e.g. N- and O-glycans), galactooligosaccharides (GOS), fructooligosaccharides (FOS), milk oligosaccharides (MOS) or even the glycomoiety of glycolipids; and polysaccharide(s), like amylose, amylopektin, cellulose, glycogen, glycosaminoglycan, or chitin. Oligo- and polysaccharides can either be linear or (multiple) branched.

Glycoconjugates are compounds in which a carbohydrate (the glycone) is linked to a noncarbohydrate moiety (the aglycon). Typically, the aglycone is either a protein (glycoprotein) or a lipid (glycolipid). In a more general sense, glycoconjugate means a carbohydrate covalently linked to any other chemical entity such as protein, peptide, lipid, or even saccharide.

Glycoconjugates represent the structurally and functionally most diverse molecules in nature. They range in complexity from relatively simple glycolipids to extraordinarily complex and multiple glycosylated proteins. Although the carbohydrate moiety is commonly composed of only a few monosaccharides, including N-acetylglucosamine, N-acetylgalactosamine, mannose, galactose, fucose, glucose, and sialic acids, their structural diversity is possibly much larger than that of proteins or DNA. The reasons for this diversity are the presence of the anomers and the ability of monosaccharides to branch and to build different (glycosidic) linkages. Accordingly, an oligosaccharide with a relatively small chain length may have an enormous number of structural isomers. Moreover, unlike protein biosynthesis, which is based on RNA as a template, the information flow from the genome to the glycome (see next paragraph for a definition) is a complex and no longer a template-driven process. The co- and post-translational modification of proteins in glycan biosynthesis is provided by enzymatic reactions. This leads to a drastic increase of complexity and structural diversity of glycans (as depicted in scheme 1 below). In practice, the term glycan refers to the carbohydrate portion of a glycoconjugate. The terms glycan, oligosaccharide and polysaccharide are synonyms and mean "compounds consisting of a medium to large number of monosaccharides linked glycosidically" (a IUPAC definition).

In order to elucidate the structural features of the glycome, which means the complete set of glycoconjugates that cells produce under specified conditions, and to understand its functions and its "counterplay" with DNA and protein "machinery", rapid, robust and high resolution bioanalytical techniques must be available.

Many analytic techniques have been utilized to analyze carbohydrates. Complex samples containing a variety of different oligosaccharides can be separated by chromatographic or electrokinetic techniques. Common chromatographic modes include size exclusion chromatography (SEC), hydrophilic interaction chromatography (HILIC), reversed phase liquid chromatography (RPLC) and reversed-phase ion-pairing chromatography (RPIPC), as well as porous graphitized carbon chromatography (PGC). Mass spectrometry (MS) and nuclear magnetic resonance (NMR) allow de novo structural characterization of complex oligosaccharides. A combination of several techniques is often applied, e.g. LC-NMR, LC-MS or CE-MS. As soon as the structure of a particular glycan is determined, its characteristic properties, such as retention or migration times, are tabulated. By comparing the data obtained for unknown samples with tabulated parameters, the rapid screening and evaluation of unknown samples can be performed. Electrokinetic separation techniques are based on the motion of charged particles under the influence of an electric field and include various electrophoretic techniques. The most important electrokinetic separation methods for glycoanalysis are capillary zone electrophoresis (CZE) and capillary gel electrophoresis (CGE). These techniques provide simultaneously high resolution, fast separation, and allow for quantification.

Multiplex capillary gel electrophoresis with laser induced fluorescence detection (xCGE-LIF) has shown to be an especially powerful tool for glycoanalysis (e.g., in R. Hennig, U. Reichl, E. Rapp, *Glycoconjugate J.* 2011, 28, 331). One advantage is the possibility to utilize a multiplex capillary array setup which offers the potential for very high throughput analysis due to parallelization of separation. Another reason for using xCGE-LIF is the very high sensitivity due to LIF detection (R. Hennig, *Diploma Thesis*, Otto-von-Guericke Universitat, Magdeburg, 2010).

Capillary electrophoresis (CE) is a family of electrokinetic separation methods and is defined by the IUPAC as "separation techniques carried out in capillaries based solely on the differences in the electrophoretic mobilities of charged species (analytes) either in aqueous or non-aqueous background electrolyte solution" (see also M.-L. Riekkola, J. A. Jönsson, R. M. Smith, *Pure Appl. Chem.* 2004, 76, 443-451). In other words, CE terms the separation of ions by electrophoresis within a very thin capillary.

CGE is defined by the IUPAC as "a special case of capillary sieving electrophoresis when the capillary is filled with a cross-linked gel" (see also M.-L. Riekkola et al., above).

The electrophoretic mobility of a compound depends on the mass to charge ratio, and when employing CGE—due to the gels sieving effect—it depends additionally from the molecular shape. Commonly, native carbohydrates cannot be separated by their mass to charge ratio, because most of them are electroneutral except the ones that contain charged residues like sialic acids, glucuronic acids, or sulfated or phosphorylated monosaccharide units.

Further, native carbohydrates show no fluorescence. Thus, for analysis via chromatographic or electrokinetic separation and fluorescence detection, it is necessary to label the oligosaccharides prior to the analysis (FIG. 1). Besides providing proper excitation and emission wavelengths (and (necessary for electrokinetic separation) additional electric charges), the dyes must be suited for coupling to the carbohydrates (see, for example, N. V. Shilova, N. V. Bovin, *Russ. J. Bioorg. Chem.* 2003, 29 (4), 339-355.

The most common and straightforward method for labeling carbohydrates with fluorescent dyes is the reductive amination. The two-step procedure yields a covalent bond between the reducing end of a carbohydrate (acetal or aldehyde group) and a primary amine. The primary amine is either incorporated into the structure of the fluorophore or bound to a linker, which is connected with the fluorescent dye.

FIG. 1 shows the main steps of separation-based glycan analysis. The glycan analysis procedure can be divided into five steps: sample preparation, glycan release, labeling, sample purification, chromatographic or electrokinetic separation with fluorescent detection and the data evaluation. In the following, the labeling of glycans and detection of labeled products according to the state of art will be described in more detail. Scheme 2 below shows the principal reaction mechanism of the reductive amination of carbohydrates (see, for example, N. Volpi, *Capillary electrophoresis of carbohydrates. From monosaccharides to complex polysaccharides*, Humana Press, New York, 2011, pp. 1-51).

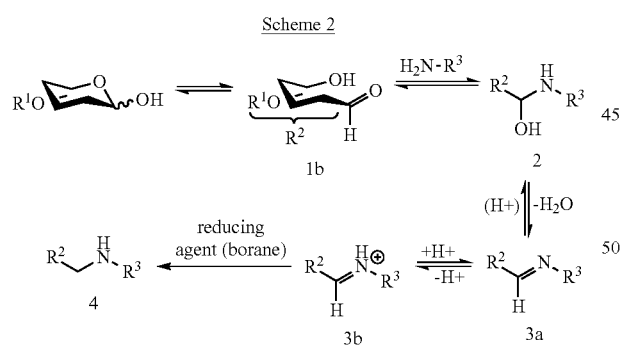

Scheme 2

The first step of the reductive amination involves a nucleophilic addition reaction where the lone electron pair of the amine nitrogen attacks the electrophilic aldehyde carbon atom of the carbohydrate residue in its open-chain form (1b). The acid-catalyzed elimination of water from intermediate 2 gives an imine (3a). Since the imine formation is reversible, the imine has to be converted into a secondary amine (4) via irreversible acid-catalyzed reduction with a hydride source, such as sodium cyanoborohydride, triacetoxy borohydride, 2-picolynyl borane, or related reagents (reducing agents in Scheme 2). The nature of borane is important, because only iminium ions 3b need to be reduced, while carbohydrates $R^2CHO$ (1b) have to remain unreactive towards the reduction (they react only with amines $R^3NH_2$ which represent fluorescent tags).

The reaction sequence depicted in Scheme 2 is based on the availability and sufficient reactivity of special reducing agents (boranes) which do not react with aldehydes (or reduce them very slowly), but under acidic conditions readily reduce iminium ions (3b). Weak or medium strong acids such as acetic ($pK_a$=4.76), malonic ($pK^1_a$=2.83) or citric acid ($pK^1_a$=3.13) are frequently used at pH=3-6 to achieve an irreversible and rapid reduction (K. R. Anumula, *Anal. Biochem.* 2006, 350, 1-23). Therefore, the applied amine ($R^3NH_2$) has to be a weak base (because only the non-protonated amine can react with aldehyde 1b in Scheme 2). In proteins, the aliphatic amino groups of lysine, nucleophilic nitrogen atoms in histidine and arginine residues are protonated at pH=3-6 and do not react with carbohydrates according to Scheme 2. Therefore, only aromatic amines with rather low $pK_a$ values of 3-5 (these are values for the conjugated acids) are required and widely used as analytical reagents for reductive amination of natural glycans. Shown below are 3 commercially available aromatic amines applicable for labeling of glycans via reductive amination, chromatographic or electrokinetic separation of conjugates and sensitive detection by fluorescence.

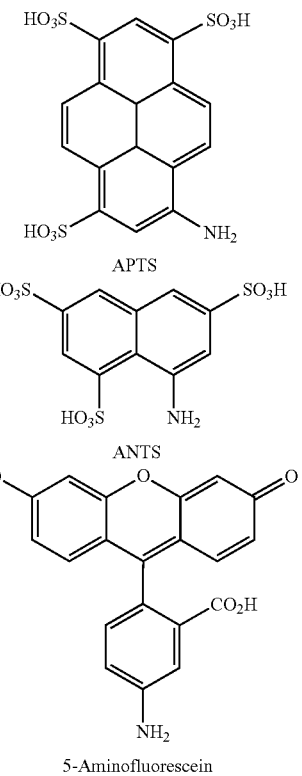

3-Aminopyrene-1,6,8-trisulfonic acid (APTS) is currently the most widely used reagent for carbohydrate labeling. Three strongly acidic residues (sulfonic acid groups) introduce three negative charges at pH>2 (in a very wide pH range). ANTS also has three negative charges, but its absorption maximum is too blue-shifted and, therefore, does not fit for the commercial 488 nm laser.

After purification (to remove proteins, excess electrolytes, excess dye, labeling reagents, etc., as also described in the Example 2 of the section "Examples" below and in references therein), the labeled sample is injected into the chromatographic column, respectively the electrokinetic capillary, and the separation is carried out. Due to their different properties (like hydrophobicity, mass/charge, shape, etc.) the different carbohydrates reach the detector according to their characteristic retention, respectively migration times.

When the labeled carbohydrates reach the fluorescence detector, the fluorescent markers are excited and the emission signal is detected.

Today, "real" high throughput analysis of labeled glycans is typically performed on commercial multiplex CGE-systems. These xCGE-LIF instruments contain a multiplexed capillary gel electrophoresis unit for the separation of charged analytes (e.g., APTS-labeled glycans), a laser and a fluorescence detector.

Scheme 3
Spectral properties of APTS and its N-alkylated derivatives in aqueous buffers (according to Z. Sharrett, S. Gamsey, L. Hirayama, B. Vilozny, J. T. Suri, R.A. Wessling, B. Singaram, *Org. Biomol. Chem.* 2009, 7, 1461-1470).

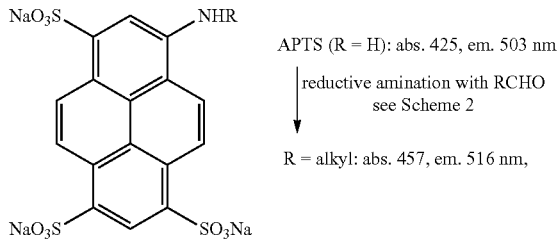

APTS (R = H): abs. 425, em. 503 nm reductive amination with RCHO
see Scheme 2

R = alkyl: abs. 457, em. 516 nm,

Other dyes than APTS may be used as fluorescent tags for carbohydrates (e.g., ANTS and 5-aminofluorescein) and their derivatives. For example, acridone dyes are described in WO 2002/099424 A3 and WO 2009/112791 A1, but not 7-aminoacridone-2-sulfonamides. WO 2012/027717 A1 describes systems comprising functionally substituted 1,6,8-trisulfonamido-3-aminopyrenes (APTS derivatives), an analyte-reactive group, a cleavable anchor as well as a porous solid phase. WO 2010/116142 A2 describes a large variety of fluorophores and fluorescent sensors compounds which also encompass aminopyrene-based dyes. However, none of these dyes has been shown or suggested to have superior spectral and electrophoretic properties, in particular as conjugates with carbohydrates, in comparison with APTS.

In view of the drawbacks of the fluorescent dyes of the prior art, the main objective of the present invention was to provide novel fluorescent dyes with improved properties, such as even higher electrophoretic mobility and/or higher brightness or other favorable spectroscopic characteristics, as compared to APTS. These properties are highly demanded from fluorescent tags for carbohydrate analysis based on electrokinetic separation with fluorescence detection and thus would provide a superior performance, here.

This objective has been achieved by providing novel fluorescent acridone and pyrene dyes with multiple negatively charged groups according to the invention, as well as the use of the disclosed novel fluorescent dyes according to.

DESCRIPTION OF THE INVENTION

In their ionized (deprotonated) form, the novel fluorescent dyes of the invention feature multiple negatively charged residues and an aromatic amino or hydrazine group attached to the fluorophore, which is excitable e.g. with an argon ion laser. Importantly, the novel dyes and their carbohydrate conjugates emit light with the maximum that is considerably shifted from that of APTS-labeled analogs. Multiple negative net charges, which are especially high in the phosphorylated derivatives (e.g. −6), provide higher electrophoretic mobility of dye-glycoconjugates, as compared to APTS—glyco-conjugates.

The structures of the novel fluorescent dyes of the invention are selected from the group consisting of compounds of the following general Formulae A-B or salts thereof:

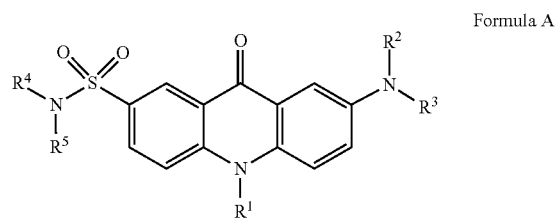

Formula A wherein
$R^1, R^2, R^3, R^4, R^5$ are independent from each other and may represent:
H, $CH_3$, $C_2H_5$, a straight or branched $C_3$-$C_{12}$, preferably $C_3$-$C_6$, alkyl or perfluoroalkyl group, a phosphonylated alkyl group $(CH_2)_mP(O)(OH)_2$, where m=1-12, preferably 2-6, with a straight or branched alkyl chain, $(CH_2)_nCOOH$, where n=1-12, preferably 1-5, or $(CH_2)_nCOOR^6$, where n=1-12, preferably 1-5, and $R^6$ may be alkyl, in particular $C_1$-$C_6$, $CH_2CN$, benzyl, fluorene-9-yl, polyhalogenoalkyl, polyhalogenophenyl, e.g. tetra- or pentafluorophenyl, pentachlorophenyl, 2- and 4-nitrophenyl, N-succinimidyl, sulfo-N-succinimidyl, 1-oxybenzotriazolyl or other potentially nucleophile-reactive leaving groups, alkyl sulfonate $((CH_2)_nSO_3H)$ or alkyl sulfate $((CH_2)_nOSO_3H)$ where n=1-12, preferably 1-5, and the alkyl chain in any $(CH_2)_n$ may be straight or branched;

a hydroxyalkyl group $(CH_2)_mOH$ or thioalkyl group $(CH_2)_mSH$, where m=1-12, preferably 2-6, with a straight or branched alkyl chain, a phosphorylated hydroxyalkyl group $(CH_2)_mOP(O)(OH)_2$, where m=1-12, preferably 2-6, with a straight or branched alkyl chain; one of $R^1$ or $R^2$ groups may be a carbonate or carbamate derivative $(CH_2)_mOCOOR^7$ or $(CH_2)_mNHCOOR^7$, where m=1-12 and $R^7$=methyl, ethyl, tert-butyl, benzyl, fluoren-9-yl, $CH_2CN$, N-succinimidyl, sulfo-N-succinimidyl, 1-oxybenzotriazolyl, phenyl, substituted phenyl group, e.g., 2- or 4-nitrophenyl, pentachlorophenyl, pentafluorophenyl, 2,3,5,6-tetrafluoro-phenyl, 2-pyridyl, 4-pyridyl, pyrimid-4-yl; $(CH_2)_mNR^aR^b$, where m=1-12, preferably 2-6, with a straight or branched alkyl chain; $R^a$, $R^b$ are independent from each other and represent hydrogen and/or $C_1$-$C_4$ alkyl groups, a hydroxyalkyl group $(CH_2)_mOH$, where m=2-6, with a straight or branched alkyl chain, a phosphorylated hydroxyalkyl group $(CH_2)_mOP(O)(OH)_2$, where m=2-6, with a straight or branched alkyl chain; an alkyl azide $(CH_2)_mN_3$, where m=1-12, preferably 2-6, with a straight or branched alkyl chain;

$R^1, R^2, R^3, R^4, R^5$ may contain a terminal alkyloxyamino group $(CH_2)_mONH_2$, where m=1-12, preferably 2-6, with a straight or branched alkyl chain, that can include one or multiple alkylamino $(CH_2)_mNH$ or alkylamido $(CH_2)_mCONH$ groups in all possible combinations with m=0-12;

$(CH_2)_nCONHR^8$, with n=1-12, preferably 1-5; $R^8$=H, $C_1$-$C_6$ alkyl, $(CH_2)_mN_3$, or $(CH_2)_m$—N-maleimido, $(CH_2)_m$—NH—COCH$_2$X (X=Br or I), with m=1-12, preferably 2-6, and with straight or branched alkyl chains in $(CH_2)_n$, $(CH_2)_m$ and $R^6$;

a primary amino group;

further, one of the residues $R^1$, $R^2$, $R^3$, $R^4$, $R^5$ may represent $CH_2$—$C_6H_4$—$NH_2$, $COC_6H_4$—$NH_2$, $CONHC_6H_4$—$NH_2$ or $CSNHC_6H_4$—$NH_2$ with $C_6H_4$ being a 1,2-, 1,3- or 1,4-phenylene, $COC_5H_3N$—$NH_2$ or $CH_2$—$C_5H_3N$—$NH_2$, with $C_5H_3N$ being pyridin-2,4-diyl, pyridin-2,5-diyl, pyridin-2,6-diyl, or pyridin-3,5-diyl;

additionally, $R^2$-$R^3$ ($R^4$-$R^5$) may form a four-, five, six-, or seven-membered cycle, or a four-, five, six-, or seven-membered cycle with or without a primary amino group $NH_2$, secondary amino group $NHR^a$, where $R^a$=$C_1$-$C_6$ alkyl, a hydroxyl group OH, or a phosphorylated hydroxyl group —OP(O)(OH)$_2$ attached to one of the carbon atoms in this cycle;

optionally $R^2$-$R^3$ ($R^4$-$R^5$) may form a four-, five, six-, or seven-membered heterocycle with an additional 1-3 heteroatoms such as O, N or S included into this heterocycle;

further, $R^1$ may represent an unsubstituted phenyl group, a phenyl group with one or several electron-donor substituents chosen from the set of OH, SH, $NH_2$, $NHR^a$, $NR^aR^b$, $R^aO$, $R^aS$, where $R^a$ and $R^b$ are independent from each other and may be $C_1$-$C_6$ alkyl groups with straight or branched carbon chains, a phenyl group with one or several electron-acceptors chosen from the set of $NO_2$, CN, COH, COOH, CH=CHCN, CH=C(CN)$_2$, $SO_2R^a$, $COR^a$, $COOR^a$, CH=CHCOR$^a$, CH=CHCOOR$^a$, CONHR$^a$, $SO_2NR^aR^b$, CONR$^a$R$^b$, where $R^a$ and $R^b$ are independent from each other and may be H, or $C_1$-$C_6$ alkyl group(s) with straight or branched carbon chains;

or $R^1$ may represent a heteroaromatic group;

with the proviso that in all compounds of Formula A above at least two, preferably at least 3, 4, 5 or 6 negatively charged groups are present under basic conditions, i.e. 7<pH<14, and these negatively charged groups represent at least partially deprotonated residues of ionizable groups selected from the following: SH, COOH, a sulfonic acid residue $SO_3H$, a primary phosphate group OP(O)(OH)$_2$, a secondary phosphate group OP(O)(OH)R$^a$, where $R^a$=$C_1$-$C_4$ alkyl or substituted $C_1$-$C_4$ alkyl, a primary phosphonate group P(O)(OH)$_2$, a secondary phosphonate group P(O)(OH)R$^a$, where $R^a$=$C_1$-$C_4$ alkyl or substituted $C_1$-$C_4$ alkyl;

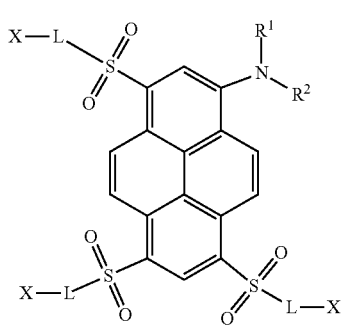

Formula B wherein $R^1$ and/or $R^2$ are independent from each other and may represent:

H, deuterium, alkyl or deutero-substituted alkyl, wherein one, several or all H atoms of the alkyl group may be replaced by deuterium, in particular alkyl or deutero-substituted alkyl with 1-12 C atoms, preferably 1-6 C atoms, e.g. $CH_3$, $C_2H_5$, a linear or branched $C_3$-$C_{12}$ alkyl or perfluoroalkyl group, or a substituted $C_2$-$C_{12}$ alkyl group; in particular, $(CH_2)_nCOOR^3$, where n=1-12, preferably 1-5, $R^3$ may be H, alkyl, in particular $C_1$-$C_6$, $CH_2CN$, benzyl, 2- and 4-nitrophenyl, fluorene-9-yl, polyhalogenoalkyl, polyhalogeno-phenyl, e.g. tetra- or pentafluorophenyl, pentachlorophenyl, N-succinimidyl, sulfo-N-succinimidyl, 1-oxybenzotriazolyl or other potentially nucleophile-reactive leaving groups, and the alkyl chain in $(CH_2)_n$ may be straight or branched; and $R^1$-$R^2$ may form a four-, five, six-, or seven-membered non-aromatic carbocycle with an additional primary amino group $NH_2$, secondary amino group $NHR^a$, where $R^a$=$C_1$-$C_6$ alkyl, or hydroxyl group OH attached to one of the carbon atoms in this cycle; optionally $R^1$-$R^2$ may form a four-, five, six-, or seven-membered non-aromatic heterocycle with an additional heteroatom such as O, N or S included into this heterocycle;

a hydroxyalkyl group $(CH_2)_mOH$, where m=1-12, preferably 2-6, with a straight or branched alkyl chain; one of $R^1$ or $R^2$ groups may be a carbonate or carbamate derivative $(CH_2)_mOCOOR^4$ or $(CH_2)_mNHCOOR^4$, where m=1-12 and $R^4$=methyl, ethyl, 2-chloroethyl, N-succinimidyl, sulfo-N-succinimidyl, 1-oxybenzotriazolyl, a phenyl group or substituted phenyl group, e.g., 2- and 4-nitrophenyl, pentachlorophenyl, pentafluorophenyl, 2,3,5,6-tetrafluoro-phenyl, 2-pyridyl, or 4-pyridyl;

$(CH_2)_mNR^aR^b$, where m=1-12, preferably 2-6, with a straight or branched alkyl chain; $R^a$, $R^b$ are independent from each other and may be H, or optionally substituted $C_1$-$C_4$ alkyl group(s), in particular, one of $R^1$ or $R^2$ groups may be an alkyl azide group $(CH_2)_mN_3$ with m=2-6 and a straight or branched alkyl chain; one of $R^1$ or $R^2$ may be $(CH_2)_nSO_2NR^5NH_2$ with n=1-12, while the substituent $R^5$ can be represented by H, alkyl, hydroxyalkyl or perfluoroalkyl groups $C_1$-$C_{12}$;

one of $R^1$ or $R^2$ groups may be a primary amino group to form aryl hydrazines Ar—NR$^6$NH$_2$ where Ar is the entire pyrene residue in Formula B and $R^6$=H or alkyl;

one of $R^1$ or $R^2$ groups may be a primary amino group to form aryl hydrazines Ar—NR$^6$NH$_2$ where Ar is the entire pyrene residue in Formula B and $R^6$=H or alkyl;

one of $R^1$ or $R^2$ groups may be a hydroxy group to form aryl hydroxylamines Ar—NR$^7$OH where Ar is the entire pyrene residue in Formula B and $R^7$=H or alkyl;

one of $R^1$ or $R^2$ groups may be an alkyloxyamino group $(CH_2)_nONH_2$ with n=1-12;

one of $R^1$ or $R^2$ groups may be $(CH_2)_nCOOR^8$, with n=1-5 and a straight or branched alkyl chain $(CH_2)_n$ and with $R^8$ selected from H, straight or branched $C_1$-$C_6$ alkyl, $CH_2CN$, 2- and 4-nitrophenyl, 2,3,5,6-tetrafluorophenyl, pentachlorophenyl, pentafluorophenyl, N-succinimidyl, sulfo-N-succinimidyl, 1-oxybenzo-triazolyl;

further, one of $R^1$ or $R^2$ may be $(CH_2)_nCONHR^9$, with n=1-5 and $R^9$=H, $C_1$-$C_6$ alkyl, $(CH_2)_mN_3$, $(CH_2)_m$—N-maleimido, $(CH_2)_m$—NHCOCH$_2$X (X=Br or I), where m=2-6 and with straight or branched alkyl chains in $(CH_2)_n$ and $R^9$; or one of $R^1$ or $R^2$ may represent $CH_2$—$C_6H_4$—$NH_2$, $COC_6H_4$—$NH_2$, $CONHC_6H_4$—$NH_2$ or $CSNHC_6H_4$—$NH_2$ with $C_6H_4$ being a 1,2-, 1,3- or 1,4-phenylene, $COC_5H_3N$—$NH_2$ or $CH_2$—$C_5H_3N$—$NH_2$, with $C_5H_3N$ being pyridin-2,4-diyl, pyridin-2,5-diyl, pyridin-2,6-diyl, or pyridin-3,5-diyl; or one of $R^1$ or $R^2$ may be an alkyl azide $(CH)N_3$ or alkine, in particular propargyl;

the linker L (which connects the dye core with the group X and tailors the spectral properties of the dye) comprises at least one carbon atom and may comprise alkyl, heteroalkyl, in particular alkyloxy such as $CH_2OCH_2$, $CH_2CH_2O$ $CH_2CH_2OCH_2$, alkylamino or dialkylamino, particularly diethanolamine or N-methyl (alkyl) monoethanolamine moieties such as $N(CH_3)CH_2CH_2O$— and $N(CH_2CH_2O$—$)_2$, difluoromethyl $(CF_2)$, alkene or alkine moieties in any combinations, at any occurrence, linear or branched, with the length ranging from $C_1$ to $C_{12}$;

the linker L may also include a carbonyl ($CH_2CO$, $CF_2CO$) moiety;

X denotes a solubilizing and/or ionizable anion-providing moiety, in particular consisting of or including a moiety selected from the group comprising hydroxyalkyl $(CH_2)_nOH$, thioalkyl $((CH_2)_nSH)$, carboxy alkyl $((CH_2)_nCO_2H)$, alkyl sulfonate $((CH_2)_nSO_3H)$, alkyl sulfate $((CH_2)_nOSO_3H)$, alkyl phosphate $((CH_2)_nOP(O)(OH)_2)$ or phosphonate $((CH_2)_nP(O)(OH)_2)$, wherein n is an integer ranging from 0 to 12 or 1 to 12, or an analogon thereof wherein one or more of the $CH_2$ groups are replaced by $CF_2$, further, the anion-providing moieties may be linked by means of non-aromatic O, N and S-containing heterocycles, e. g., piperazines, pipecolines, or, alternatively, one of the groups X may bear any of the moieties listed above for groups $R^1$ and $R^2$, also with any type of linkage listed for group L, and independently from other substituents;

with the proviso that in all compounds represented by Formula B three or six negatively charged groups are present in the residues X of Formula B under basic conditions, i.e. 7<pH<14, and these negatively charged groups represent at least partially deprotonated residues of ionizable groups selected from the following: SH, COOH, $SO_3H$, $OSO_3H$, $OP(O)(OH)_2$, $OP(O)(OH)R^a$, where $R^a$=$C_1$-$C_4$ alkyl or substituted $C_1$-$C_4$ alkyl, $P(O)(OH)_2$, $P(O)(OH)R^a$, where $R^a$=$C_1$-$C_4$ alkyl or substituted $C_1$-$C_4$ alkyl.

Compounds of Formulae A and B can exist and be applied in the form of salts that involve all possible types of cations, preferably $Na^+$, $K^+$, $Li^+$, $NH_4^+$, organic ammonium (e.g. trialkylammonium) or organic phosphonium cations.

In more specific embodiments, a fluorescent dye salt according to the present invention may comprise negatively charged acid groups, in particular sulfonate and/or phosphate groups, and counterions selected from inorganic or organic cations, preferably alkaline metal cations, ammonium cations or cations of organic ammonium or phosphonium compounds (such as trialkylammonium cations), and/or may comprise a positively charged group or a charge-transfer complex formed at the nitrogen site $N(R^1)R^2$ in the dye of Formulae A-D as well as a counterion, in particular selected from anions of a strong mineral, organic or a Lewis acid.

The term "substituted" as used herein, generally refers to the presence of one or more substituents, in particular substituents selected from the group comprising straight or branched alkyl, in particular $C_1$-$C_4$ alkyl, e.g. methyl, ethyl, propyl, butyl; isoalkyl, e.g. isopropyl, isobutyl (2-methylpropyl); secondary alkyl group, e.g. sec-butyl (but-2-yl); tert-alkyl group, e.g. tert-butyl (2-methylpropyl). Additionally, the term "substituted" may refer here to alkyl groups having at least one deuterium-, fluoro-, chloro- or bromo substituent instead of hydrogen atoms, or methoxy, ethoxy, 2-(alkyloxy)ethyloxy groups ($AlkOCH_2CH_2O$), and, in a more general case, oligo(ethylenglycol) residues of the art $Alk(OCH_2CH_2)_nOCH_2CH_2$—, where Alk=$CH_3$, $C_2H_5$, $C_3H_7$, $C_4H_{10}$, and n=1-23.

The term "alkyl" generally may refer to any alkyl group selected from the group comprising straight or branched alkyl, more specifically $C_1$-$C_{20}$ alkyl, $C_1$-$C_{12}$ alkyl, or $C_1$-$C_6$ alkyl, e.g. methyl, ethyl, propyl, butyl; isoalkyl, e.g. isopropyl, isobutyl (2-methylpropyl); secondary alkyl group, e.g. sec-butyl (but-2-yl); tert-alkyl group, e.g. tert-butyl (2-methylpropyl) etc.

The terms "aromatic heterocyclic group" or "heteroaromatic group", as used herein, generally refer to an unsubstituted or substituted cyclic aromatic radical (residue) having from 5 to 10 ring atoms of which at least one ring atom is selected from S, O and N; the radical being joined to the rest of the molecule via any of the ring atoms. Representative, but not limiting examples are furyl, thienyl, pyridinyl, pyrazinyl, pyrimidinyl, pyrrolyl, imidazolyl, thiazolyl, oxazolyl, isooxazolyl, thiadiazolyl, oxadiazolyl, quinolinyl and isoquinolinyl.

Compounds of the general structural Formula A above are acridone dyes, compounds of the Formula B above are pyrene dyes.

More specifically, according to the IUPAC rules the compounds of Formula A are 7-aminoacridon-2-sulfonamides, whereas the compounds of Formula B are 1-aminopyrene dyes with functionally substituted sulfonyl groups in positions 3, 6, 8, i.e. (functionally substituted) 1,6,8-trisulfonyl-3-aminopyrenes, as shown in the basic structural formulae in Scheme 4 below.

Scheme 4

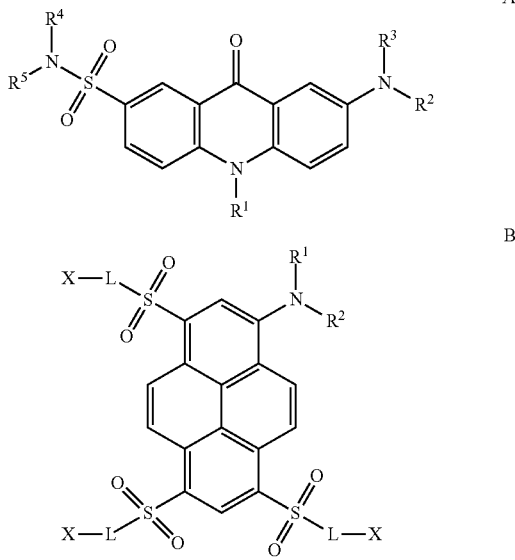

The novel fluorescent dyes of the present invention exhibit a number of favorable characteristics:

aromatic amino (ArNH$_2$), hydrazine (NRNH$_2$), hydrazide (CONRNH$_2$), hydroxylamine (RNHOH) or alkoxyamino group (RONH$_2$) with pK$_b$=11-8 (pK$_a$=3-6) for efficient and clean reductive amination at pH~2-5 or direct condensation with carbohydrates; preferably, the aromatic amino group is primary, but it can also be a secondary one; see Scheme 4 for structures large net charges in conjugates—in the range of −3 to −6 at pH=7-10 very good solubility in aqueous media at a wide range of pH; high brightness (which is the overall result of the fluorescence quantum yield and extinction)

exceptional stability of the dye core against reduction with borane-based reagents and at pH=3-6 the ability to be excited with an argon ion laser (emitting at 488 and 514 nm) with a perfect spectral match and high fluorescence quantum yields minimal emission at ca. 520 nm The dyes are amenable to purification up to 99%.

The novel fluorescent tags of the invention even allow the detection of "heavy" glycans with very long migration times. Due to these long migration times and peak-broadening, such "heavy" glycans are very difficult to detect electrokinetically; especially if APTS is used as fluorescent tag.

In the following, more specific embodiments of the present invention are described.

In Formula A above, NR$^1$ and/or N(R$^2$)R$^3$ comprise carbonyl- or nucleophile-reactive groups. Preferably, R$^1$, R$^2$, and R$^3$ are represented by H, linear or branched alkyl, hydroxyalkyl or perfluoroalkyl groups. Substituents R$^3$, R$^4$ and R$^5$ preferably comprise solubilizing and/or anion-providing groups, particularly hydroxyalkyl ((CH$_2$)$_n$OH), thioalkyl ((CH$_2$)$_n$SH), carboxyalkyl ((CH$_2$)$_n$CO$_2$H), alkyl sulfonate ((CH$_2$)$_n$SO$_3$H), alkyl sulfate ((CH$_2$)$_n$OSO$_3$H), alkyl phosphate ((CH$_2$)$_n$OP(O)(OH)$_2$) or alkyl phosphonate ((CH$_2$)$_n$P(O)(OH)$_2$), wherein n is an integer ranging from 1 to 12.

Alternatively, substituents R$^1$, R$^2$, R$^3$, R$^4$ and R$^5$ may be represented by carboxylic acid residues (CH$_2$)$_n$COOH, where n=1-12, and their reactive esters (CH$_2$)$_n$COOR$^6$ as nucleophile-reactive groups. R$^6$ can be H, alkyl, (tert-butyl including), benzyl, fluorene-9-yl, polyhalogenoalkyl, CH$_2$CN, polyhalogenophenyl (e. g., tetra- or pentafluorophenyl, pentachlorophenyl), 2- and 4-nitrophenyl, N-succinimidyl, sulfo-N-succinimidyl, 1-oxybenzotriazolyl or other potentially nucleophile-reactive leaving groups. The alkyl chains (or backbones) (CH$_2$)$_n$ may be linear or branched.

Further, the aryl amino groups (NR$^1$ and NR$^2$R$^3$) in Formula A can be connected to an analyte-reactive group via (poly)methylene, carbonyl, nitrogen or sulfur-containing linear or branched linkers, particularly (CH$_2$)$_m$CON(R$^7$), CO(CH$_2$)$_m$N(R$^7$), CO(CH$_2$)$_m$S(CH$_2$)$_n$, (CH$_2$)$_m$S(CH$_2$)$_n$CO, CO(CH$_2$)$_m$SO$_2$ (CH$_2$)$_n$, (CH$_2$)$_m$SO$_2$(CH$_2$)$_n$CO, their combinations, or linked as a part of nitrogen-containing non-aromatic heterocycles (e.g., piperazines, pipecolines, oxazolines); m and n are integers ranging from 0 to 12 or 1 to 12. The substituent R$^7$ may be represented by any of the functional groups listed for R$^1$, R$^2$ R$^3$, R$^4$ and R$^5$ above.

Substituents R$^1$, R$^2$ and R$^3$ in Formula A may be also represented by a primary amino group, thus comprising carbonyl-reactive aryl hydrazines, (R$^2$=H, R$^1$ or R$^3$=NH$_2$ or R$^1$=NH$_2$, R$^2$, R$^3$=alkyl, perfluoroalkyl or alkyl) conjugated or substituted with solubilizing and/or anion-providing moieties, listed as possible candidates for R$^4$ and R$^5$, particularly: hydroxyalkyl (CH$_2$)$_n$OH, thioalkyl ((CH$_2$)$_n$SH), carboxyalkyl ((CH$_2$)$_n$CO$_2$H), alkyl sulfonate ((CH$_2$)$_n$SO$_3$H), alkyl sulfate ((CH$_2$)$_n$OSO$_3$H), alkyl phosphate ((CH$_2$)$_n$OP(O)(OH)$_2$) or phosphonate ((CH$_2$)$_n$P(O)(OH)$_2$), wherein n is an integer ranging from 0 to 12 or 1 to 12. Alternatively, hydrazine derivatives might be represented by sulfonyl hydrazides, where R$^4$=NH$_2$, while R$^5$ are alkyl, perfluoroalkyl or alkyl groups decorated with solubilizing and/or anion-providing groups of the types mentioned above.

Alternatively, aryl amino groups (NR$^1$ and/or NR$^2$R$^3$) in Formula A can be connected to an acyl hydrazine or alkyl hydrazine moiety indirectly, via linkers, thus comprising hydrazides (ZCONHNH$_2$) or hydrazines (ZNHNH$_2$), respectively. Here Z denotes the dye residue of Formula A that includes aryl amino groups and linkers. In particular, R$^1$ and R$^2$ may be represented by: (CH$_2$)$_m$CON(R$^7$), CO(CH$_2$)$_m$N(R$^7$), CO(CH$_2$)$_m$S(CH$_2$)n, (CH$_2$)$_m$S(CH$_2$)$_n$CO, CO(CH$_2$)$_m$SO$_2$ (CH$_2$)n, (CH$_2$)$_m$SO$_2$(CH$_2$)$_n$CO and their combinations; m and n are integers ranging from 0 to 12. Substituent R$^7$ can be represented by any of the functional groups for R$^1$, R$^2$, R$^3$, R$^4$ and R$^5$ that are listed above as candidates for functional groups R$^1$-R$^5$, particularly: hydroxyalkyl (CH$_2$)$_n$OH, thioalkyl ((CH$_2$)$_n$SH), carboxyalkyl ((CH$_2$)$_n$CO$_2$H), alkyl sulfonate ((CH$_2$)$_n$SO$_3$H), alkyl sulfate ((CH$_2$)$_n$OSO$_3$H), alkyl phosphate ((CH$_2$)$_n$OP(O)(OH)$_2$) or phosphonate ((CH$_2$)$_n$P(O)(OH)$_2$), wherein n is an integer ranging from 0 to 12 or 1 to 12. Linkers may also be represented by non-aromatic O, N and S-containing heterocycles (e. g., piperazines, pipecolines).

Further, R$^1$, R$^2$ and R$^3$ may be represented by CH$_2$—C$_6$H$_4$—NH$_2$, COC$_6$H$_4$—NH$_2$, CONHC$_6$H$_4$—NH$_2$ or CSNHC$_6$H$_4$—NH$_2$ with C$_6$H$_4$ being a 1,2-, 1,3- or 1,4-phenylene, COC$_5$H$_3$N—NH$_2$ or CH$_2$—C$_5$H$_3$N—NH$_2$, with C$_5$H$_3$N being pyridine-2,4-diyl, pyridine-2,5-diyl, pyridine-2,6-diyl, pyridine-3,5-diyl.

The analyte-reactive group at variable positions R$^1$, R$^2$, R$^3$, R$^4$ and R$^5$ may be represented by an aromatic or heterocyclic amine, carboxylic acid, ester of the carboxylic acid (e.g., N-hydroxysuccinimidyl or another amino reactive ester); or represented by alkyl azide (CH$_2$)$_n$N$_3$, alkine (propargyl), amino-oxyalkyl (CH$_2$)$_n$ONH$_2$, maleimido (C$_4$H$_3$NO$_2$ with a nucleophile-reactive double bond) or halogeno ketone function (COCH$_2$X; X=Cl, Br and I), as well as halogeno amide group (NRCOCH$_2$X, R=H, C1-C6-alkyl, X=Cl, Br, I) connected either directly or indirectly via carbonyl, amido, nitrogen, oxygen or sulfur-containing linkers listed for hydrazine derivatives where n=1-12.

According to some more preferred embodiments of the present invention, the substituent R$^1$ in the above Formula A is defined as follows:

R$^1$ in Formula A represents hydrogen, a lower alkyl group (C$_1$-C$_4$), an unsubstituted phenyl group, a phenyl group with one or several electron-donor substituents chosen from the set of OH, SH, NH$_2$, NHR$^a$, NR$^a$R$^b$, R$^a$O, R$^a$S, OP(O)(OR$^a$)(OR$^b$) where R$^a$ and R$^b$ are independent from each other and may be C$_1$-C$_{12}$, preferably C$_1$-C$_6$, alkyl groups with linear or branched chains, a phenyl group with one or several electron-acceptors chosen from the set of NO$_2$, CN, COH, COOH, CH=CHCN, CH=C(CN) 2, SO$_2$R$^a$, SO$_3$R$^a$, COR$^a$, COOR$^a$, CH=CHCOR$^a$, CH=CHCOOR$^a$, CONHR$^a$, SO$_2$NR$^a$R$^b$, CONR$^a$R$^b$, P(O)(OR$^a$)(OR$^b$) where R$^a$ and R$^b$ are independent from each other and may be H, or C$_1$-C$_6$ alkyl group(s) with straight or branched carbon chains;

alternatively, R$^1$ may represent an aromatic heterocyclic group, in particular, 2-pyridyl, 3-pyridyl, 4-pyridyl, 2-thienyl, 3-thienyl, pyrimidin-4-yl, pyrimidin-2-yl, pyrimidin-5-yl, or other electron acceptor groups derived from aromatic heterocycles, such as 4-pyridyl-N-oxides, N-alkylpyridinium salts, or betaines, in particular, N-(ω-sulfoalkyl)-4-pyridinium, N-(ω-sulfoalkyl)-2-pyridinium, N-(1-hydroxy-4,4,5,5-tetrafluorocyclopent-1-en-3-on-2-yl)-4-pyridinium, N-(1-hydroxy-4,4,5,5-tetrafluorocyclopent-1-en-3-on-2-yl)-2-pyridinium.

In particular, $R^1$ may represent a positively charged heterocyclic group derived from 2-pyridyl, 3-pyridyl, or 4-pyridyl precursors with an 7-aminoacridon-2-sulfonamide backbone and alkylating agents (e.g. alkyl halides, alkyl sulfonates, alkyl triflates, 1,3-propanesulton, 1,4-butanesulton) or electrophiles (e. g., perfluorocyclopentene).

Especially preferred are compounds of the structural Formula A above that have one of the following formulae:

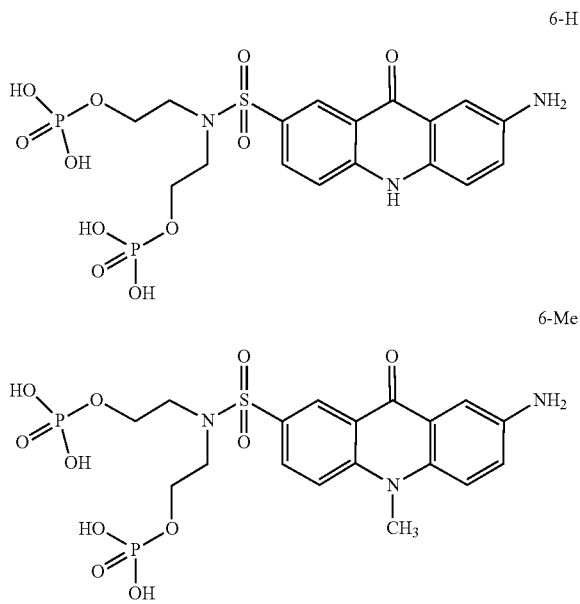

In the Formula B, L is a divalent linker that connects the dye core with solubilizing and/or ionizable moieties and also tailors the spectral properties.

Typically, its presence results in considerable bathofloric and bathochromic shifts accompanied by a better match to the 488 nm commercial lasers, as compared to APTS dye tag, where fragment L is absent and X is OH.

The linker L in the Formula B comprises or consists of at least one carbon atom and can represent alkyl, heteroalkyl (e. g., alkyloxy: $CH_2OCH_2$, $CH_2CH_2O$ $CH_2CH_2OCH_2$), difluoromethyl ($CF_2$), alkene or alkine moieties in any combinations, at any occurrence, linear or branched, with the length ranging from C1 to C12. The linker can also include a carbonyl ($CH_2CO$, $CF_2CO$) and Sulfonamides are the case when L is an alkylamino or a dialkylamino group, particularly diethanolamine or N-methyl (alkyl) monoethanolamine moieties (i.e., $N(CH_3)CH_2CH_2O$— and $N(CH_2CH_2O—)_2$), which allow further connection to a solubilizing and/or ionizable moieties X. Certain embodiments of this invention represent the combination of moieties L and X according to the formulae $(CH_2)_3OP(O)(OH)_2$ and $N(CH_3)(CH_2)_2OP(O)(OH)_2$. The sulfonamides of this type thus have general formula $SO_2NR^3R^4$, where $R^3$ and $R^4$ are independent from each other and can be represented by H, alkyl, heteroalkyl (e. g., alkyloxy: $CH_2OCH_2$, $CH_2CH_2O$, $CH_2CH_2OCH_2$), difluoromethyl ($CF_2$) in any combinations, linear or branched, with the length ranging from C1 to C12, also bearing terminal OH groups.

$N(R^1)R^2$ in the Formula B preferably comprises a carbonyl- or nucleophile-reactive group. Substituents $R^1$ and $R^2$ are independent from each other and can be both represented by hydrogen. One of those can be a linear or branched alkyl (perfluoroalkyl) group $C_1$-$C_{12}$. At the same time, one of $R^1$ and $R^2$ may be represented by carboxylic acid residues $(CH_2)_nCOOH$ and their regular or reactive esters $(CH_2)_nCOR^3$ where n is an integer ranging from 1 to 12. The residue $R^3$ is H, alkyl, (tert-butyl including), benzyl, fluorene-9-yl, polyhalogenoalkyl, $CH_2CN$, polyhalogenophenyl (e. g., tetra- or pentafluoro phenyl, pentachlorophenyl), 2- and 4-nitrophenyl, N-succinimidyl, sulfo-N-succinimidyl, 1-oxybenzotriazolyl or other potentially nucleophile-reactive leaving groups. The alkyl chains (or backbones) ($CH_2$), may be linear or branched. Particularly, the formula can be depicted as Z—$NR^1(CH_2)_nCOR^4$, where Z is the rest of the molecule in Formula B that also includes groups L and X.

Further, the nucleophile-reactive group $COR^5$ can be connected to the aryl amino group $N(R^1)$ $R^2$ via (poly) methylene, oxymethylene ($CH_2OCH_2$, $CH_2CH_2OCH_2$, PEG) carbonyl, carbonate, carbamate, urethane, nitrogen or sulfur-containing linkers (spacers) branched or linear, particularly $(CH_2)_mCON(R^6)$, $CONH(CH_2)n$, $(CH_2)_mOCONH(CH_2)_n$, $CO(CH_2)_n$, $CO(O)NR^6$, $(CH_2)_mSO_{2m}N(R^6)$, $CO(CH_2)_mS(CH_2)_n$, $(CH_2)_mS(CH_2)_nCO$, $CO(CH_2)_mSO_2(CH_2)_n$, $(CH_2)_mSO_2NR^6$, and their combinations; m and n are integers ranking from 0 to 12, $R^6$=alkyl. The reactive group $R^5$ can be linked by means of non-aromatic O, N and S-containing heterocycles (e. g., piperazines, pipecolines, oxazolines). Substituent $R^6$ might be represented by H, alkyl, hydroxyalkyl or perfluoroalkyl groups $C_1$-$C_{12}$.

One of the substituents $R^1$ and $R^2$ in Formula B may be represented by a primary amino group, thus comprising carbonyl-reactive aryl hydrazines ($R^1$=$NH_2$, $R^2$=alkyl, perfluoroalkyl) or by a hydroxy group to form aryl hydroxylamines (ArNHOH). Alternatively, the alkyl hydrazine or hydroxylamine reactive moiety in Formula B can be connected to aryl amino group $N(R^1)R^2$ via linkers listed above for the reactive group $R^4$. Sulfonyl hydrazides constitute a special case when $R^1$ or $R^2$=$(CH_2)_nSO_2NR^6NH_2$ with n=1-12, while the substituent $R^6$ can be represented by H, alkyl, hydroxyalkyl or perfluoroalkyl groups $C_1$-$C_{12}$. The sulfonylamide (sulfonamide, sulfamide) group can be also attached via diverse linkers listed above for the case with the reactive groups $R^4$, $R^3$ and $R^5$.

Further, $R^1$ and $R^2$ may be represented by $CH_2$—$C_6H_4$—$NH_2$, $COC_6H_4$—$NH_2$, $CONHC_6H_4$—$NH_2$ or $CSNHC_6H_4$—$NH_2$ with $C_6H_4$ being a 1,2-, 1,3- or 1,4-phenylene, $COC_5H_3N$—$NH_2$ or $CH_2$—$C_5H_3N$—$NH_2$, with $C_5H_3N$ being pyridine-2,4-diyl, pyridine-2,5-diyl, pyridine-2,6-diyl, pyridine-3,5-diyl.

Substituents $R^1$ and $R^2$ may be also represented by alkyl azide $(CH_2)_nN_3$, alkine (propargyl), maleimido ($C_4H_3NO_2$ with a nucleophile-reactive double bond) or halogeno-ketone function ($COCH_2X$; X=Cl, Br and I) connected either directly or via carbonyl, amido, nitrogen or sulfur-containing linkers listed for hydrazine derivatives; n=1-12.

Group X in Formula B denotes solubilizing and/or ionizable anion-providing moieties, particularly the ones that provide enhanced electrophoretic mobility. Group X can include hydroxyalkyl $(CH_2)_nOH$, thioalkyl $((CH_2)_nSH)$, carboxy alkyl $((CH_2)_nCO_2H)$, alkyl sulfonate $((CH_2)_nSO_3H)$, alkyl sulfate $((CH_2)_nOSO_3H)$, alkyl phosphate $((CH_2)_nOP(O)(OH)_2)$ or phosphonate $((CH_2)_nP(O)(OH)_2)$, wherein n is an integer ranging from 0 to 12. Alternatively, the CH$_2$ group can be replaced by CF$_2$. The anion-providing moieties can be also linked by means of non-aromatic O, N and S-containing heterocycles (e.g., piperazines, pipecolines). Alternatively, one of the groups X can bear any of the carbonyl- or nucleophile-reactive moieties listed for groups R$^1$ and R$^2$, also with any type of linkage listed for group L, and independently from other substituents.

As already mentioned above, compounds of Formula B can exist and be applied in the form of salts that involve all possible types of cations, preferably Na$^+$, Li$^+$, K$^+$, NH$_4^+$ and organic ammonium or organic phosphonium cations.

According to one specific embodiment of the invention, the anion-providing group(s) X may represent, at each occurrence in Formula B, one to four groups SO$_3$H attached to the respective linker group L at one or more sites (and for each type of linkage as defined for L above).

According to another specific embodiment of the invention, the compounds of the structural Formula B above are alkylsulfonyl derivatives as depicted in Formula C

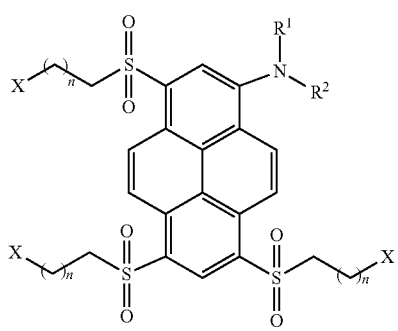

Formula C wherein
R$^1$ and/or R$^2$ are independent from each other and may represent: H, deuterium, alkyl or deutero-substituted alkyl, wherein one, several or all H atoms in the alkyl group may be replaced by deuterium atoms, in particular alkyl or deutero-alkyl with 1-12 C atoms, preferably 1-6 C atoms, e.g. CH$_3$, C$_2$H$_5$, a straight or branched C$_3$-C$_{12}$, preferably C$_3$-C$_6$, alkyl group, or a substituted C$_2$-C$_{12}$, preferably C$_2$-C$_6$, alkyl group; in particular, (CH$_2$)$_n$COOR$^3$, where n=1-12, preferably 1-5, R$^3$ may be H, CH$_2$CN, 2- and 4-nitrophenyl, 2,3,5,6-tetrafluorophenyl, pentachlorophenyl, pentafluorophenyl, N-succinimidyl, sulfo-N-succinimidyl, 1-oxybenzotriazolyl and the alkyl chain in (CH$_2$)$_n$ may be straight or branched; and R$^1$-R$^2$ may form a four-, five, six-, or seven-membered non-aromatic carbocycle with an additional primary amino group NH$_2$, secondary amino group NHR$^a$, where R$^a$=C$_1$-C$_6$ alkyl, or hydroxyl group OH attached to one of the carbon atoms in this cycle;

optionally R$^1$-R$^2$ may form a four-, five-, six-, or seven-membered non-aromatic heterocycle with an additional heteroatom such as O, N or S included into this heterocycle;

a hydroxyalkyl group (CH$_2$)$_m$OH, where m=1-12, preferably 2-6, with a straight or branched alkyl chain; one of R$^1$ or R$^2$ groups may be a carbonate or carbamate derivative where one of R$^1$ or R$^2$ groups is (CH$_2$)$_m$OCOOR$^4$ or (CH$_2$)$_m$NHCOOR$^4$, where m=1-12 and R$^4$=methyl, ethyl, 2-chloroethyl, N-succinimidyl, sulfo-N-succinimidyl, a phenyl group or substituted phenyl group, e.g., 2- and 4-nitrophenyl, pentachlorophenyl, pentafluorophenyl, 2,3,5,6-tetrafluoro-phenyl, 2-pyridyl, or 4-pyridyl;

(CH$_2$)$_m$NR$^a$R$^b$, where m=1-12, preferably 2-6, with a straight or branched alkyl chain; R$^a$, R$^b$ are independent from each other and may be H, or optionally substituted C$_1$-C$_4$ alkyl group(s), in particular, one of R$^1$ or R$^2$ groups may be an alkyl azide group (CH$_2$)$_m$N$_3$ with m=2-6 and a straight or branched alkyl chain; one of R$^1$ or R$^2$ groups may be (CH$_2$)$_n$COOR$^b$, with n=1-5 and a straight or branched alkyl chain (CH$_2$)$_n$ and with R$^3$ selected from H, straight or branched C$_1$-C$_6$ alkyl, CH$_2$CN, 4-nitrophenyl, 2,3,5,6-tetrafluorophenyl, pentachlorophenyl, pentafluoro-phenyl, N-succinimidyl, 1-oxybenzotriazolyl;

further, one of R$^1$ or R$^2$ may be (CH$_2$)$_n$CONHR$^6$, with n=1-12, preferably 1-5, and R$^6$=H, C$_1$-C$_6$ alkyl, (CH$_2$)$_m$N$_3$, (CH$_2$)$_m$—N-maleimido, (CH$_2$)$_m$—NHCOCH$_2$X (X=Br or I), where m=2-6 and with straight or branched alkyl chains in (CH$_2$)$_n$ and R$^6$; or one of R$^1$ or R$^2$ may represent CH$_2$—C$_6$H$_4$—NH$_2$, COC$_6$H$_4$—NH$_2$, CONHC$_6$H$_4$—NH$_2$ or CSNHC$_6$H$_4$—NH$_2$ with C$_6$H$_4$ being a 1,2-, 1,3- or 1,4-phenylene, COC$_5$H$_3$N—NH$_2$ or CH$_2$—C$_5$H$_3$N—NH$_2$, with C$_5$H$_3$N being pyridin-2,4-diyl, pyridin-2,5-diyl, pyridin-2,6-diyl, or pyridin-3,5-diyl; the (CH$_2$)$_n$—CH$_2$ linker, with n=1-5, between the SO$_2$ fragment and the residue X in Formula C may represent a straight-chain, branched or cyclic group having 2-6 carbon atoms;

X=SH, COOH, OSO$_3$H, SO$_3$H, OP(O)(OH)$_2$, OP(O)(OH)R$^a$, where R$^a$=optionally substituted C$_1$-C$_4$ alkyl, P(O)(OH)$_2$, P(O)(OH)R$^a$, where R$^a$=optionally substituted C$_1$-C$_4$ alkyl;

with the proviso that in all compounds represented by Formula C three or six negatively charged groups are present in the residues X of Formula C under basic conditions, i.e. 7<pH<14, and these negatively charged groups represent at least partially deprotonated residues of ionizable groups selected from the following: SH, COOH, OSO$_3$H, SO$_3$H, OP(O)(OH)$_2$, OP(O)(OH)R$^a$, where R$^a$=C$_1$-C$_4$ alkyl or substituted C$_1$-C$_4$ alkyl, P(O)(OH)$_2$, P(O)(OH)R$^a$, where R$^a$=C$_1$-C$_4$ alkyl or substituted C$_1$-C$_4$ alkyl.

According to a more specific embodiment, of the invention, the fluorescent dye of the invention is represented by Formula C wherein X at each occurrence is SO$_3$H and n is 1-12, preferably 1-6, or a salt thereof.

According to another specific embodiment of the invention, the compounds of the structural Formula B above are sulfamide derivatives as depicted in Formula D

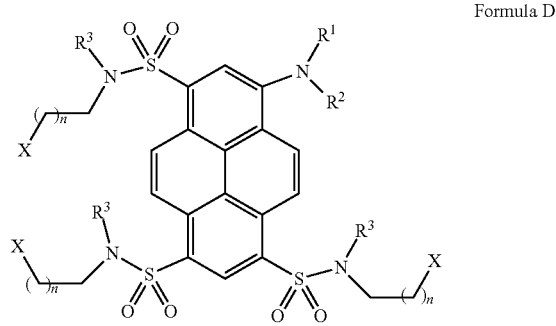

Formula D wherein

R¹ and/or R² are independent from each other and may represent H, deuterium, alkyl or deutero-substituted alkyl, wherein one, several or all H atoms in the alkyl group may be replaced by deuterium atoms, in particular alkyl or deutero-alkyl with 1-12 C atoms, preferably 1-6 C atoms, e.g. $CH_3$, $C_2H_5$, or a straight or branched, optionally substituted, $C_3$-$C_{12}$, preferably $C_3$-$C_6$, alkyl group; in particular, $(CH_2)_n COOR^4$, where n=1-12, preferably 1-5, $R^4$ may be H, $CH_2CN$, 2- and 4-nitrophenyl, 2,3,5,6-tetrafluorophenyl, pentachlorophenyl, pentafluorophenyl, N-succinimidyl, N-sulfosuccinimidyl, and the alkyl chain in $(CH_2)_n$ may be straight or branched; and R¹-R² may form a four-, five, six-, or seven-membered non-aromatic carbocycle with an additional primary amino group $NH_2$, secondary amino group $NHR^a$, where $R^a$=optionally substituted $C_1$-$C_6$ alkyl, or hydroxyl group OH attached to one of the carbon atoms in this cycle; or optionally R¹-R² may form a four-, five, six-, or seven-membered non-aromatic heterocycle with a heteroatom such as O, N or S included into this heterocycle; R¹ and/or R² may further represent:

a hydroxyalkyl group $(CH_2)_m OH$, where m=1-12, preferably 2-6, with a straight or branched, optionally substituted alkyl chain; one of R¹ or R² groups may be a carbonate or carbamate derivative $(CH_2)_m OCOOR^5$ or $(CH_2)_m NHCOOR^5$, where m=1-12 and $R^5$=methyl, ethyl, 2-chloroethyl, $CH_2CN$, N-succinimidyl, sulfo-N-succinimidyl, 1-oxybenzotriazolyl, a phenyl group or substituted phenyl group, such as 2- and 4-nitrophenyl, pentachlorophenyl, pentafluoro-phenyl, 2,3,5,6-tetrafluorophenyl, 2-pyridyl, 4-pyridyl;

$(CH_2)_m NR^a R^b$, where m=1-12, preferably 2-6, with a straight or branched alkyl chain; $R^a$, $R^b$ are independent from each other and represent hydrogen and/or optionally substituted $C_1$-$C_4$ alkyl groups;

$(CH_2)_m N_3$, m=1-12, preferably 2-6, with a straight or branched alkyl chain;

—$(CH_2)_n COOR^4$, with n=1-12, preferably 1-5 and a straight or branched alkyl chain $(CH_2)_n$ and with $R^4$ selected from H, straight or branched $C_1$-$C_6$ alkyl, $CH_2CN$, 2- and 4-nitrophenyl, 2,3,5,6-tetrafluorophenyl, pentachlorophenyl, pentafluorophenyl, N-succinimidyl, sulfo-N-succinimidyl, 1-oxybenzotriazolyl;

$(CH_2)_n CONHR^5$, where n=1-12, preferably 1-5 and $R^5$=H, substituted or unsubstituted $C_1$-$C_6$ alkyl, $(CH_2)_m N_3$, $(CH_2)_m$—N-maleimido, $(CH_2)_m$—$NHCOCH_2Y$ (Y=Br, I) where m=1-12, preferably 2-6, with straight or branched alkyl chains in $(CH_2)_n$ and $R^5$;

further, R¹ or R² may represent $CH_2$—$C_6H_4$—$NH_2$, $COC_6H_4$—$NH_2$, $CONHC_6H_4$—$NH_2$ or $CSNHC_6H_4$—$NH_2$ with $C_6H_4$ being a 1,2-, 1,3- or 1,4-phenylene, $COC_5H_3N$—$NH_2$ or $CH_2$—$C_5H_3N$—$NH_2$, with $C_5H_3N$ being pyridin-2,4-diyl, pyridin-2,5-diyl, pyridin-2,6-diyl, or pyridin-3,5-diyl; $R^3$=H, $(CH_2)_q CH_2X$, $C_2H_5$, a straight or branched $C_3$-$C_6$ alkyl group, $C_m H_{2m} OR$, where m=2-6, with a straight or branched alkane-diyl chain $C_m H_{2m}$, and $R^3$=H, $CH_3$, $C_2H_5$, $C_3H_7$, $CH_3 (CH_2CH_2O)_k CH_2CH_2$; with k=1-12; while the $(CH_2)_q CH_2$ linker may represent a straight-chain, branched or cyclic group having 2-6 carbon atoms;

in Formula D, the $(CH_2)_n$—$CH_2$ linker, with n=1-12, preferably 1-5, between the sulfonamide fragment $SO_2N$ and the residue X may represent a straight-chain, branched or cyclic group having 2-6 carbon atoms;

X=SH, COOH, $SO_3H$, $OSO_3H$, $OP(O)(OH)_2$, $OP(O)(OH)R^a$, where $R^a$=substituted or unsubstituted $C_1$-$C_4$ alkyl, $P(O)(OH)_2$, $P(O)(OH)R^a$, where $R^a$=substituted or unsubstituted $C_1$-$C_4$ alkyl;

with the proviso that in all compounds represented by Formula D three, six, nine or twelve negatively charged groups are present in the residues X of Formula C under basic conditions, i.e. 7<pH<14, and these negatively charged groups represent at least partially deprotonated residues of ionizable groups selected from the following: SH, COOH, $SO_3H$, $OSO_3H$, $OP(O)(OH)_2$, $OP(O)(OH)R^a$, where $R^a$=$C_1$-$C_4$ alkyl or substituted $C_1$-$C_4$ alkyl, $P(O)(OH)_2$, $P(O)(OH)R^a$, where $R^a$=$C_1$-$C_4$ alkyl or substituted $C_1$-$C_4$ alkyl.

According to preferred embodiments of the invention, the substituents R¹ and R² in the above Formulae B, C and D are defined as follows:

R¹ and/or R² in Formula B represent H, deuterium, alkyl or deutero-substituted alkyl, wherein one, several or all H atoms in the alkyl group may be replaced by deuterium atoms, in particular alkyl or deutero-alkyl with 1-12 C atoms, preferably 1-6 C atoms, such as methyl, ethyl, propyl etc., 4,6-dihalo-1,3,5-triazinyl ($C_3N_3X_2$) where halogen X is preferably chlorine, 2-, 3- or 4-aminobenzoyl ($COC_6H_4NH_2$), 2-, 3- or 4-aminophenylureyl ($NCONHC_6H_4NH_2$), 2-, 3- or 4-aminophenylthioureyl ($NCSNHC_6H_4NH_2$) or linked carbonic acid residues and their reactive esters of the general formulae $(CH_2)_{m1} COOR^3$, $(CH_2)_{m1} OCOOR^3$ $(CH_2)_{n1} COOR^3$ or $(CO)_{m1}(CH_2)_{m2}(CO)_{n1}(NH)_{n2}$ $(CO)_{n3}(CH_2)_{n4} COOR^3$ where the integers m1, m2 and n1, n2, n3, n4 independently range from 1 to 12 and from 0 to 12, respectively, with the chain $(CH_2)_m$/n being straight, branched, saturated, unsaturated, partially or completely deuterated, and/or or included into a carbo- or heterocycle containing N, O or S, whereas $R^3$ is H, D or a nucleophile-reactive leaving group, preferably including but not limited to N-succinimidyl, sulfo-N-succinimidyl, 1-oxybenzotriazolyl, cyanomethyl, polyhalogenoalkyl, polyhalogenophenyl, e.g. tetra- or pentafluorophenyl, 2- or 4-nitrophenyl.

Compounds of Formulae C and D can exist and be applied in the form of salts that involve all possible types of cations, in particular as mentioned above for Formula B, preferably $Na^+$, $Li^+$, $K^+$, $NH_4^+$ and organic ammonium or organic phosphonium cations.

Especially preferred compounds of the general structural Formulae B, C and D above have one of the following formulae:

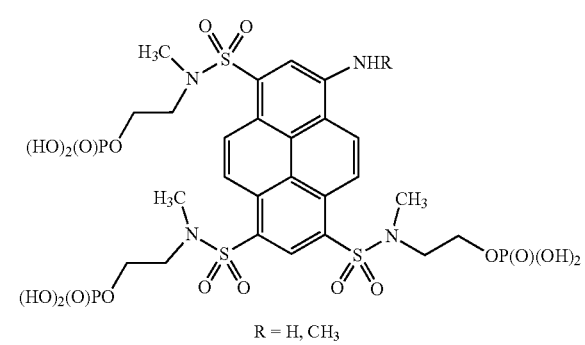

8-R

R = H, $CH_3$

-continued

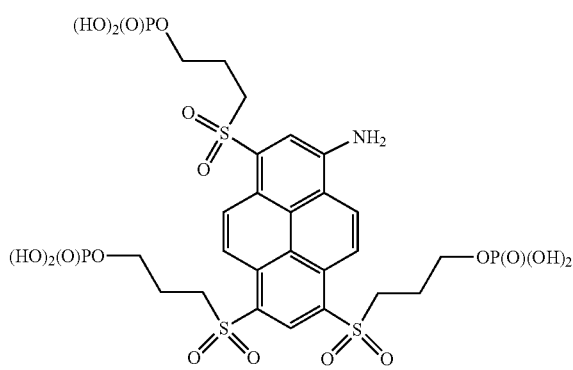

15

One preferred embodiment of the present invention relates to compounds Formulae A-B or A-D above, where the negative charges are provided by several primary phosphate groups, in particular, doubly O-phosphorylated 7-aminoacridon-2-sulfonamides (two phosphate groups), triple O-phosphorylated 1,6,8-tris[(o-hydroxyalkyl)sulfonyl]-pyrene-3-amines (three phosphate groups), and 1,6,8-tris[N-(ω-hydroxyalkyl)sulfonylamido]pyrene-3-amines. These compounds possess superior brightness and considerably better electrophoretic mobilities, compared to APTS.

The novel compounds of the invention have small molecular size and, in preferred embodiments, a drastically increased high negative net charge (z) is provided (such as, at least, z=−4 for phosphorylated acridones and z=−6 for phosphorylated pyrene dyes). These two requirements are equivalent to a low hydrodynamic radius and a low mass to charge ratio (m/z), respectively. As a result, high velocities and fast separations at good analytical resolution can be achieved in electrokinetic measurements for these compounds and the corresponding labeled carbohydrates.

The negative charges are provided by acidic groups which can be deprotonated in basic or even neutral media. Phosphate groups are preferred for this purpose, because primary alkyl phosphates (R—OPO$_3$H$_2$) have pK$_a$ values for the first and the second acidic protons in the range of 1-2 and 6-7, respectively. As a consequence, one single phosphate group can introduce two negative charges in buffer solutions under basic conditions (e.g., at pH 8, R—OPO$_3^{2-}$ is present). To achieve the negative charge of −4, the attachment of two phosphate groups is necessary, etc. However other acidic groups, in particular selected from the groups X as defined in Formulae A-B above are also suitable.

Generally, the compounds of Formulae A-B above are suitable and advantageous for the use as a fluorescent label for amino acids, peptides, proteins, including primary and secondary antibodies, single-domain antibodies, docetaxel, avidin, streptavidin and their modifications, aptamers, nucleotides, nucleic acids, toxins, lipids, carbohydrates, including 2-deoxy-2-aminoglucose and other 2-deoxy-2-aminoaminopyranosides, glycans, glucans, biotin, and other small molecules, i.e. having molecular masses of less than 1500 Da, e.g., jasplakinolide and its modifications.

Compounds 7-R (R=H, Me), 13a, 13b, 16 and 18 (Scheme 5 below) possess free hydroxyl groups and are suitable as precursors for obtaining phosphorylated pyrene dyes of the general Formula B. In particular, compounds 7-R (R=H, Me) were phosphorylated directly (POCl$_3$ in trimethyl phosphate) and afforded dyes 8-R (R=H, Me). Analogously, dyes 13a,b and 18 were phosphorylated using POCl$_3$ in trimethyl phosphate. Thus, both precursor dyes 13a and 13b gave (after the basic work-up of the reaction mixture) compound 15. Compound 16 has a free carboxyl group which can be used a reactive center for bioconjugation. Thus, compound 16 represents a fluorescent label for amino acids, peptides, proteins, including primary and secondary antibodies, single-domain antibodies, docetaxel, avidin, streptavidin and their modifications, aptamers, modified nucleotides, modified nucleic acids containing an amino group, toxins, lipids, carbohydrates, including 2-deoxy-2-aminoglucose and other 2-deoxy-2-aminoaminopyranosides, modified biotin (e.g., biocytin), and other small molecules, i.e. having molecular masses of less than 1500 Da (e.g., jasplakinolide and its modifications).

Scheme 5

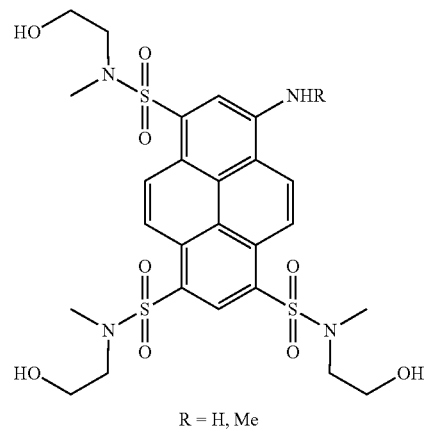

7-R

R = H, Me

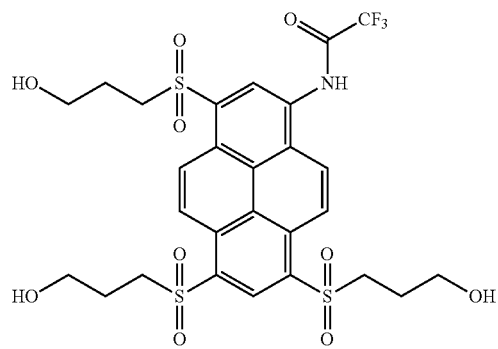

13a

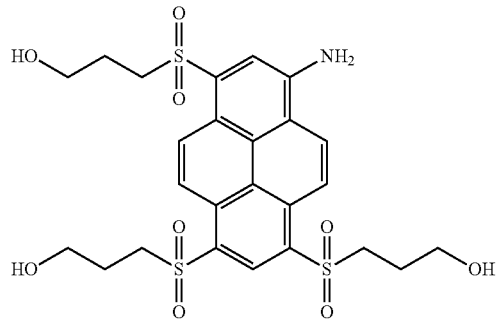

13b

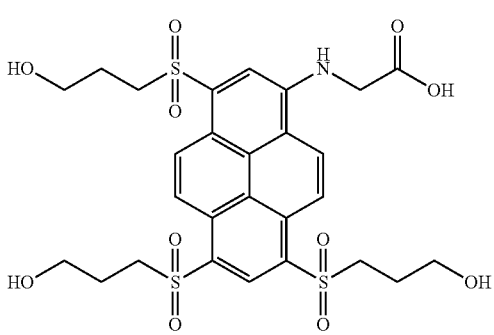

16

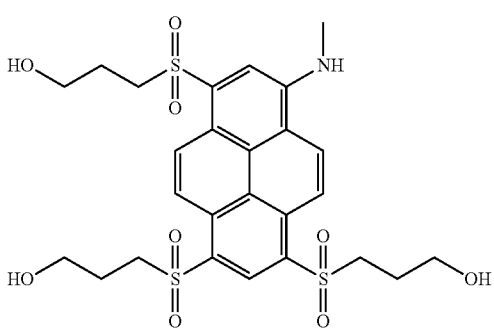

18

Consequently, a closely related aspect of the present invention relate to the use of compounds of the structural Formulae A-B as fluorescent reagents for conjugation to a broad range of analytes, wherein the conjugation comprises formation of at least one covalent chemical bond or at least one molecular complex with a chemical entity or substance, such as amine, carboxylic acid, aldehyde, alcohol, aromatic compound, heterocycle, dye, amino acid, amino acid residue coupled to any chemical entity, peptide, protein, carbohydrate, nucleic acid, toxin and lipid.

The claimed compounds are suitable for and may be used in a method for fluorescent labelling and detecting of target molecules. Typically, such a method implies reacting a compound according to any one of Formulae A-D above with a target molecule selected from the group comprising amino acids, peptides, proteins, including primary and secondary antibodies, single-domain antibodies, docetaxel, avidin, streptavidin and their modifications, aptamers, (modified) nucleotides, (modified) nucleic acids, toxins, lipids, carbohydrates, including 2-deoxy-2-aminoglucose and other 2-deoxy-2-aminoaminopyranosides, glycans, glucans, (modified) biotin (e.g., biocytin), and other small molecules, i.e. having molecular masses of less than 1500 Da (e.g., jasplakinolide and its modifications). The labeling is followed by separation, detection, quantification and/or isolation of the labeled fluorescent derivatives by means of chromatographic and/or electrokinetic techniques.

Further the present invention encompasses also carbohydrate-dye conjugates comprising a fluorescent dye according to Formulae A-B or A-D above.

More specifically, the dye in said conjugates, in particular carbohydrate-conjugates, is selected from the compounds of the formulae 6-H, 6-Me, 8-H, 15 or 19 and 20 as shown in Scheme 6 below.

The compounds of Formulae A-B or A-D above are suitable and advantageous for the use in the reductive amination of reducing sugars, i.e. monomeric, oligomeric or polymeric carbohydrates possessing an aldehyde group in a free form or protected form, e.g. as semiacetal, including glycans (as shown in Scheme 2 and 6).

Consequently, closely related aspects of the present invention relate to this use and to a method for the reductive amination of reducing sugars comprising reacting a compound of Formulae A-D above with a monomeric, oligomeric or polymeric carbohydrate possessing an aldehyde group in a free form or as semiacetal, including a glycan, for a sufficient time to effect the reductive amination and chromatographic or electrokinetic separation of the labeled fluorescent derivatives optionally followed by detection of analytes by means of optical spectroscopy, including fluorescence detection and/or mass spectrometric detection. Examples of dye-conjugate structures are given in Scheme 6.

The compounds of Formulae A-D and the carbohydrate-dye conjugates comprising the same make up a dye set that features high negative net charges, accompanied by favorable absorption/emission properties (see Table 2) and electrophoretic mobilities.

Scheme 6

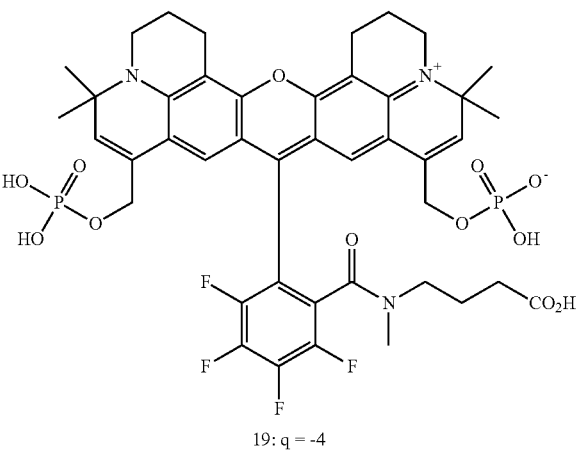

19: q = -4

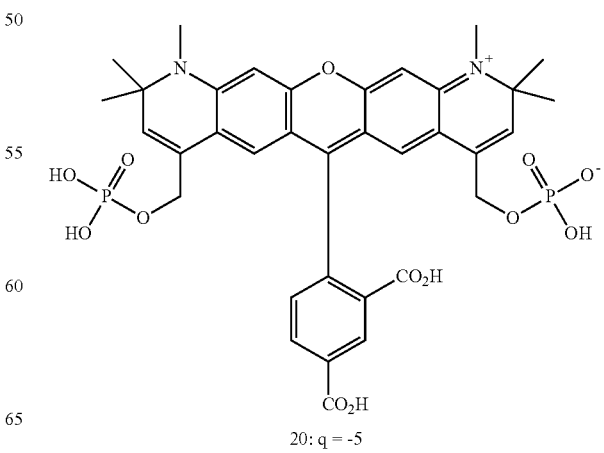

20: q = -5

23

-continued

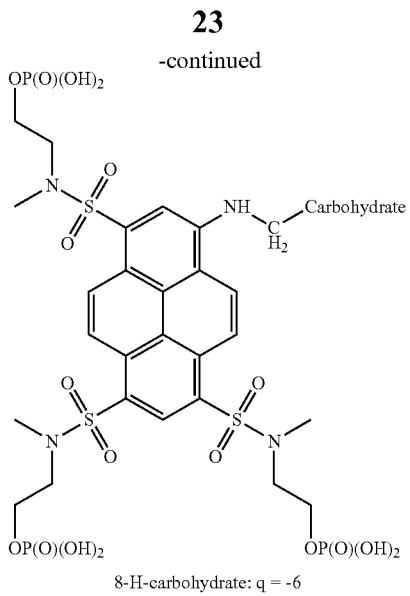

8-H-carbohydrate: q = -6

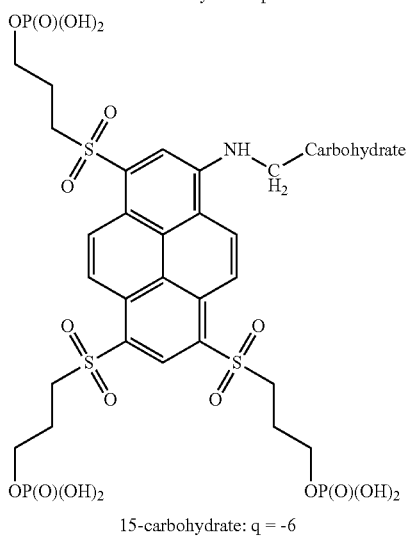

15-carbohydrate: q = -6

24

-continued

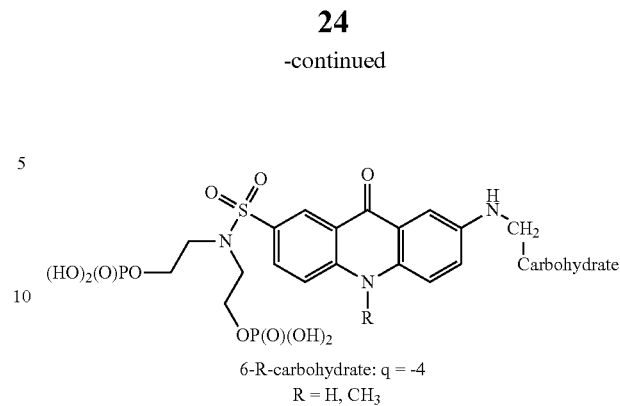

6-R-carbohydrate: q = -4
R = H, CH₃

General Synthesis of the Novel Fluorescent Dyes of the Invention

Synthetic routes to the new sulfonated 2 (7)-aminoacridone and 1-aminopyrene dyes are given in schemes 7-10 below.

Scheme 7 depicts the preparation of the double O-phosphorylated 7-aminoacridone-2-[N,N'-bis-(2-hydroxyethyl)]-sulfonamides 6-H and 6-Me. The known reaction between 2-chloro-5-nitrobenzoic acid and aniline in the presence of $K_2CO_3$ and catalytic amounts of $Cu(NO_2)_2$ (185° C., 2-4 h) afforded 4-nitro-N-phenylanthranilic acid (not shown in Scheme 5) according to the procedures described in WO 2007/049057 and US2012/0015373. 4-Nitro-N-phenylanthranilic acid was cyclized to 2-nitroacridin-9 (10H)-one (1-H) ($POCl_3$, reflux, 3 h). Experimental details of the further syntheses are given in a special section with examples.

Scheme 7. Preparation of the doubly O-phosphorylated 7-aminoacridon-2-[N,N-bis-(2-hydroxyethyl)]sulfonamides.

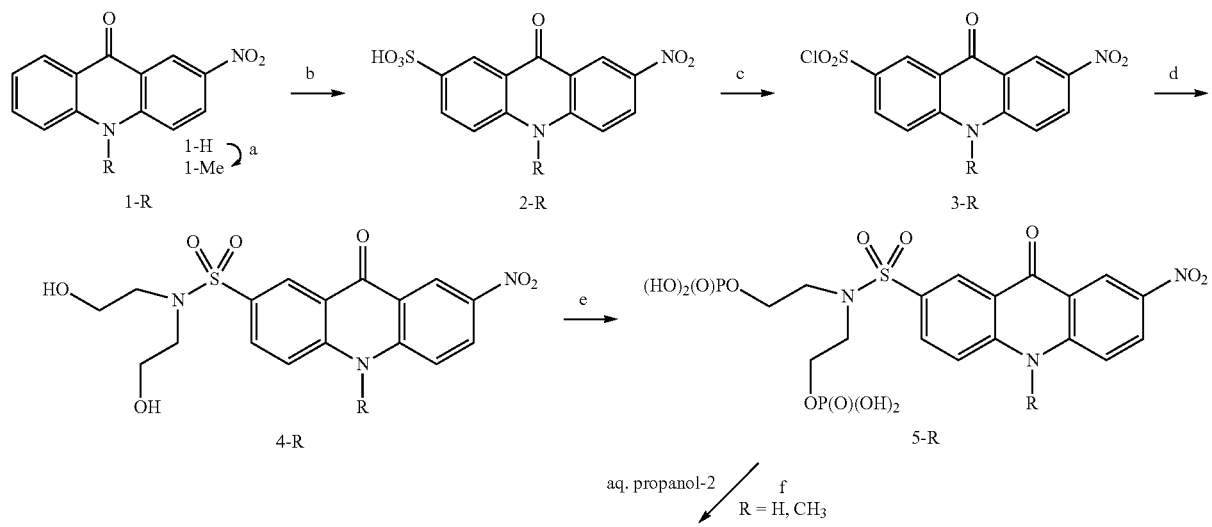

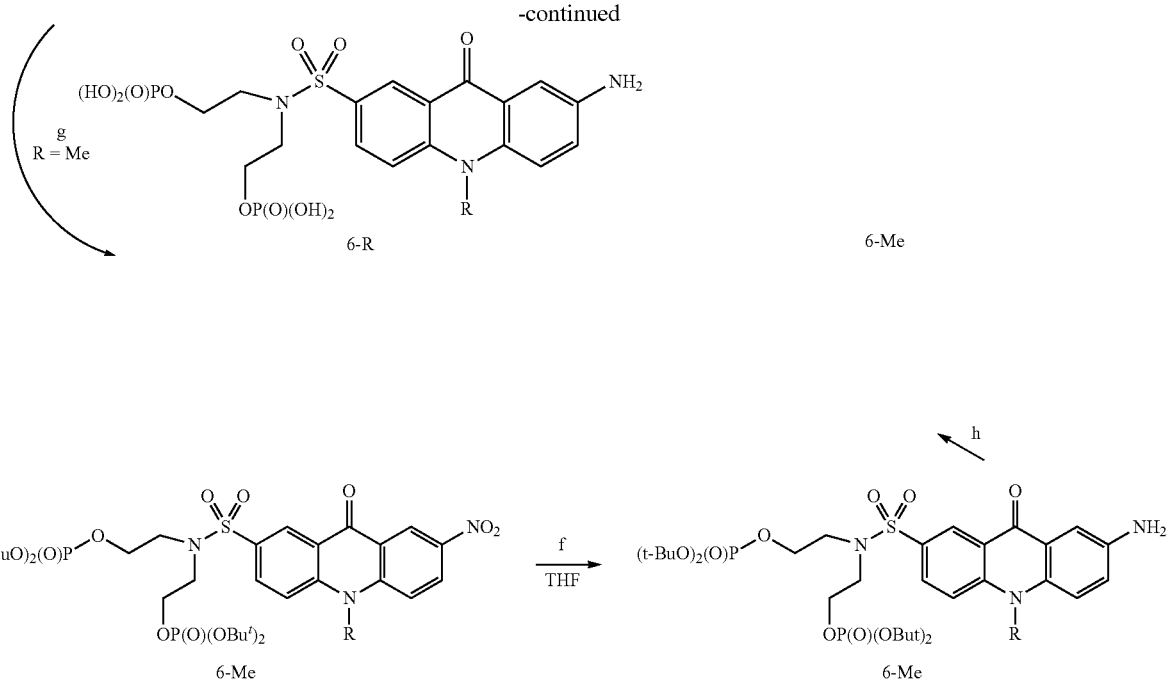

Reagents and conditions: a) NaH, DMSO, 50-60° C., then CH₃I, r.t., overnight; b) 20% SO₃ in H₂SO₄, 100° C., 1.5 h; c) ClSO₃H, 50° C., 2 h, then r.t., overnight; d) diethanolamine, aq THF or aq. MeCN, r.t., overnight; e) POCl₃, (MeO)₃PO, r.t., then aq. Et₃N*H₂CO₃ buffer (pH 8); f) H₂, Pd/C (10% Pd, oxidized form), aq. propanol-2, overnight, r.t. and ambient pressure; g) (tBuO)₂PN(i-C₃H₇)₂, 1H-tetrazol, DMF, 40° C., 1.5 h; then 5-6M tBuOOH in decane, 0° C.-r.t.; h) TFA, aq. MeCN, room temp; then aq. Et₃N*H₂CO₃ buffer (pH 8).

The synthetic route to the triple O-phosphorylated 1,6,8-tris[[N-(2-hydroxyethyl)-N-methyl]sulfonylamido]pyrene-3-amines 8-R is shown in Scheme 8. Detailed experimental procedures are given in the section with examples.

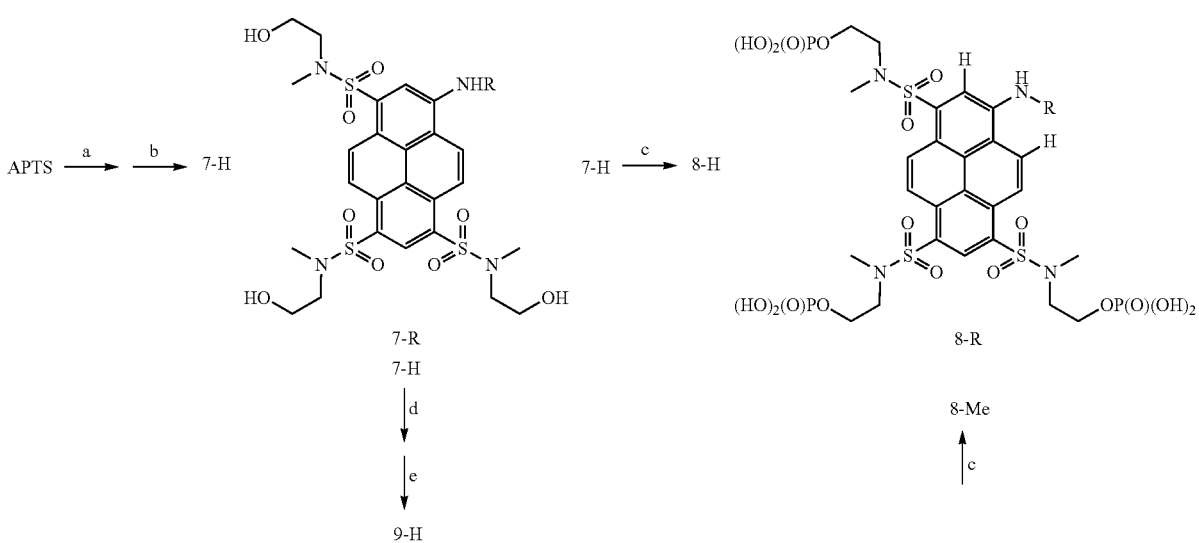

Scheme 8.
Preparation of the triple O-phosphorylated 1,6,8-tris [[N-(2-hydroxyethyl)-N-methyl]sulfonylamido]pyrene-3-amines.

-continued

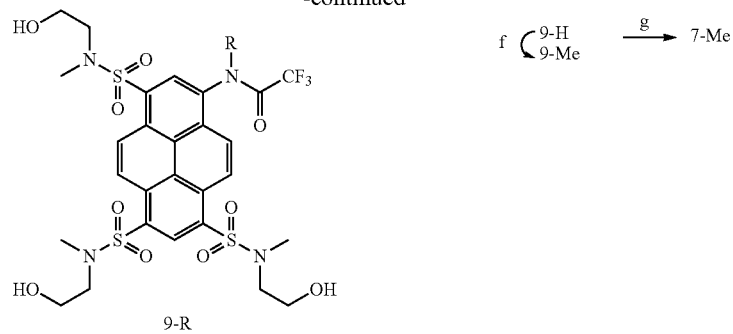

9-R

Reagents and conditions: a) ClSO₃H, 65° C., 3 h overnight;
b) CH₃NHCH₂CH₂OH, aq. MeCN, r. t., overnight; c) POCl₃, (MeO)₃PO,
r. t., then aq. Et₃N*H₂CO₃ buffer (pH 8-8.5); d) (CF₃CO)₂O,
CH₂Cl₂, Et₃N, r. t.; e) MeOH, NaHCO₃; f) CH₃I, Cs₂CO₃, DMF, 70° C.,
40 min; g) Na₂CO₃, aq. MeOH; r. t.

The synthetic route to the triple O-phosphorylated 1,6,8-tris[(3-hydroxypropyl)sulfonyl]-pyrene-3-amine 15 is shown in Scheme 9. Detailed experimental procedures are given in the Example Section.

Scheme 9.
Preparation of the triple O-phosphorylated 1,6,8-tris[(3-hydroxypropyl)-sulfonyl]-pyrene-3-amine 15.

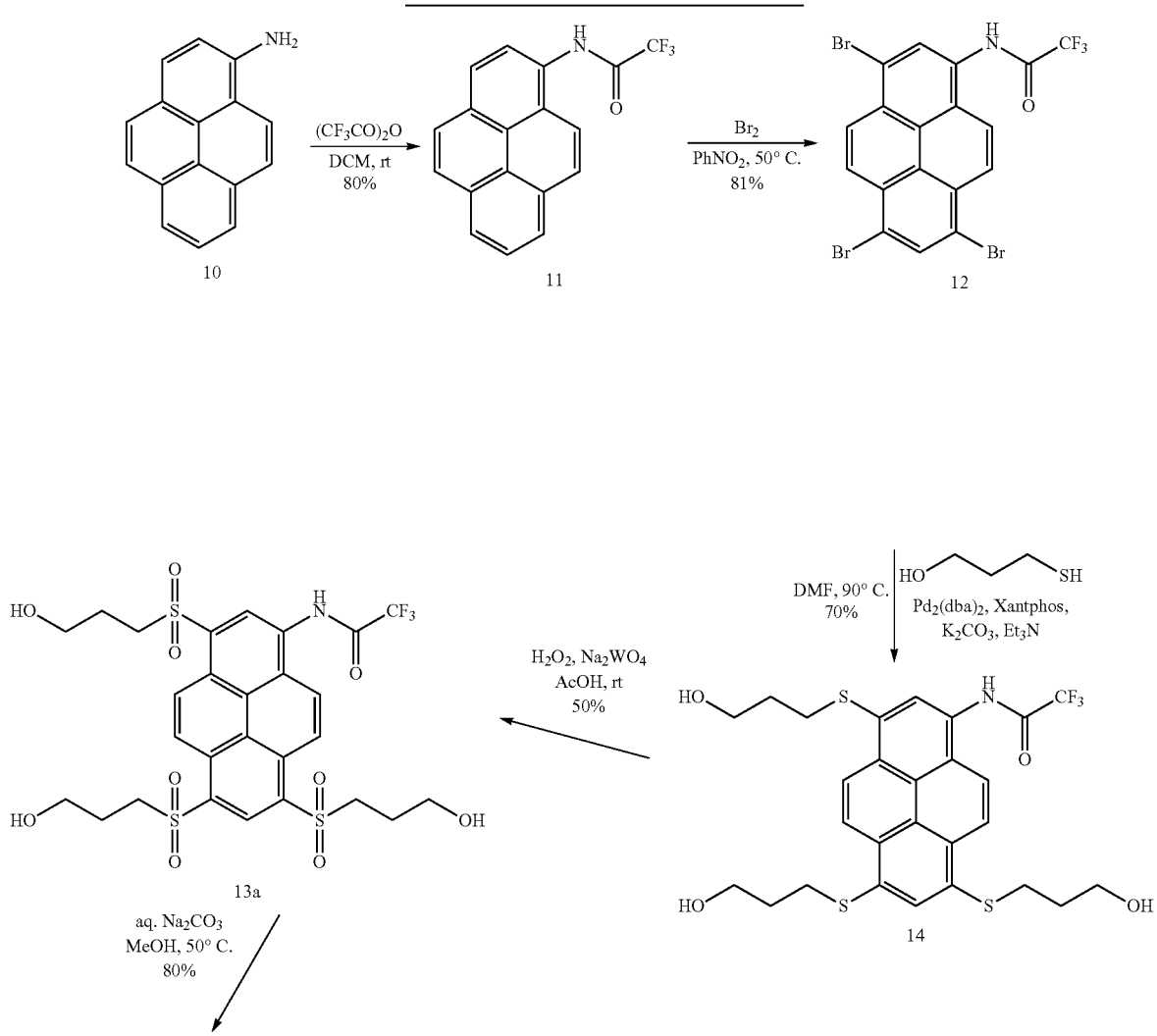

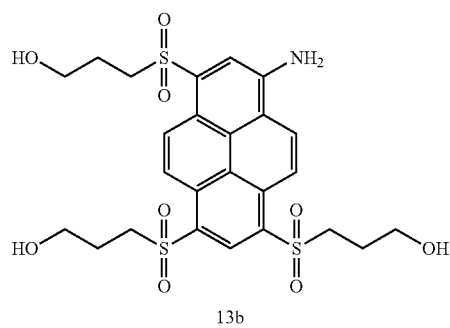

13b

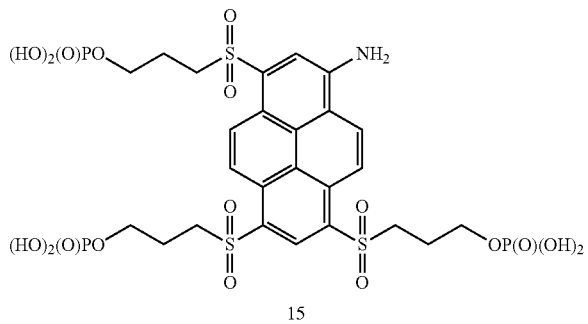

15 a) POCl₃
(MeO)₃P, r. t.;
b) aq.
Et₃N*H₂CO₃
pH 8-8.5
60%

A priori, pyrene derivatives 7-R/8-R and 15 promised better photophysical properties than 7-aminoacridon-2-[N, N-bis-(2-hydroxyethyl)]sulfonamides 6-H and 6-Me. In particular, higher molar extinction coefficients and higher fluorescence quantum yields (higher "brightness") could be expected. For example, in order to prepare pyrene dye 15, 1-aminopyrene (10)—a cheap commercially available starting material—was used as a building block (Scheme 9). APTS was also synthesized by the inventors starting from 1-aminopyrene (10) and using the reported method (Sharrett et al., Org. Biomol. Chem. 2009, 7, 1461-1470). 1-Aminopyrene (10) has an amino group which acts as an electron-donor residue and a reactive site. Shifting the absorption spectrum to the red is necessary, as compound 10 has an absorption maximum at 336 nm and the emission maximum at 445 nm (in MeOH). The bathochromic and bathofluoric shifts can be achieved by introduction of electron-acceptor groups into the pyrene fluorophore followed by the mono or double alkylation of the amino group. The later modifications take place in the course of reductive amination of glycans and convert the primary amino group to a more electron-donating secondary or tertiary amine. The electronic effects of the substituents can be illustrated, and their relative strengths can be compared by the magnitudes and signs of the Hammett constants (see Table 1).

If one assumes that the amino group is attached to C-1, then the substituents can be introduced to C-3, C-6 and C-8 (in the course of electrophilic substitution reaction). The introduction of acceptor groups into the "active" positions 6 and 8 of pyrene system (corresponding to the para-position in benzene ring), as well to C-3 (corresponds to the meta-position in benzene ring) leads to the formation of a donor-acceptor dye with red-shifted bands. This red-shift is due to a "push-pull" electronic effect between the electron-donating amino group and the electron-withdrawing groups in positions 3, 6 and 8. Valuable precursor groups are, for example, sulfonic acid residues in APTS (convertible to sulfonamides; see Scheme 8) and thioethers in compound 14, which can be oxidized to sulfones and become much more powerful electron-withdrawing residues (Scheme 9). Alkyl sulfones (represented by compounds 13b, 15, 16 and 18) have highest values of the Hammett δ-constants in Table 1 and this indicates that they are more powerful acceptors than sulfonamides (compounds 7-H, 7-Me, 8-H, 8-Me). Another reason for choosing sulfonamides and alkyl sulfones in the dye design is that they can be combined with hydroxyl residues required for attaching primary phosphate or other ionizable groups.

TABLE 1

Hammett constants for different electron-donor and electron-acceptor groups in meta and para positions. Positive values correspond to electron-acceptors; negative values to electron-donor groups. Hydrogen atom has, by definition, the zero values of "sigma" constants. The data are taken from Hansch, A. Leo, R.W. Taft, A survey of Hammett substituent constants and resonance and field parameters. Chem. Rev. 1991, 91, 165-195.

| Name | Substituent | $\sigma_m$ | $\sigma_p$ |
|---|---|---|---|
| Amino | —NH₂ | −0.16 | −0.66 |
| Alkyl amino | —NHMe | −0.21 | −0.70 |
| Dialkyl amino | —NMe₂ | −0.16 | −0.83 |
| Alkylthio | —SMe | 0.15 | 0.00 |
| Alkyl sulfon | —SO₂Me | 0.60 | 0.72 |
| Alkyl sulfoxide | —SOMe | 0.52 | 0.49 |
| Sulfonamide | —SO₂NH₂ | 0.53 | 0.60 |

Before starting to introduce any groups into the 1-amino pyrene scaffold (the first reaction would be always an aromatic electrophilic substitution), in some cases it was necessary to protect the amino group of 1-aminopyrene 10 (Scheme 9). The inventors used acetylation with trifluoroacetic anhydride (quite a new option) and obtained the acetylated amine 11. In this case, the trifluoroacetyl group is a better choice than acetyl group (which was used, for example, by Li et al., J. Am. Chem. Soc. 1994, 116, 9890-9893) because it is acid-stable, but can be easily cleaved under mild basic conditions. After the protection of the amino group by trifluoroacetylation, the electrophilic substitution in positions 3, 6 and 8 of compound 11 led to the tribromo aminopyrene (12). This tribromide represented a very important intermediate, as the aromatic bromine residues can be readily converted to a number of other functionalities. For example, a convenient synthetic way for the introduction of the thioether groups was published by Mispelaere-Canvivet et al., Tetrahedron 2005, 61, 5253-5259, who reported a Pd-catalyzed cross-coupling of thiols with aryl bromides. It was found that unprotected 3-mercapto-1-propanol can be directly used to obtain triol 14. The straightforward oxidation of 14 to the trisulfonyl derivative 13a was performed using concentrated hydrogen peroxide in acetic acid and sodium tungstate as a catalyst (compare: Xu et al., Molecules 2010, 15, 766-779). Compound 13a was deprotected in methanol by treatment with aq. Na₂CO₃ to give the free amine 13b which was, in turn, phosphorylated to compound 15.

Direct phosphorylation of aromatic amines with unprotected amino groups (7-R to 8-R in Scheme 8 and 13b to 15 in Scheme 9) using POCl₃ in trimethyl phosphate followed by treatment with aqueous Et₃N*H₂CO₃ buffer proved to be possible. Aromatic amino groups also underwent phosphorylation, but due to very poor electron density, these amino groups readily lost the phosphate residues in aqueous solutions (under slightly acidic or basic conditions).

On the contrary, primary phosphate groups in dyes 8-R (R=H, CH₃) and 15 are hydrolytically stable at the pH=3 (reductive amination) and the pH=8 (electrophoresis).

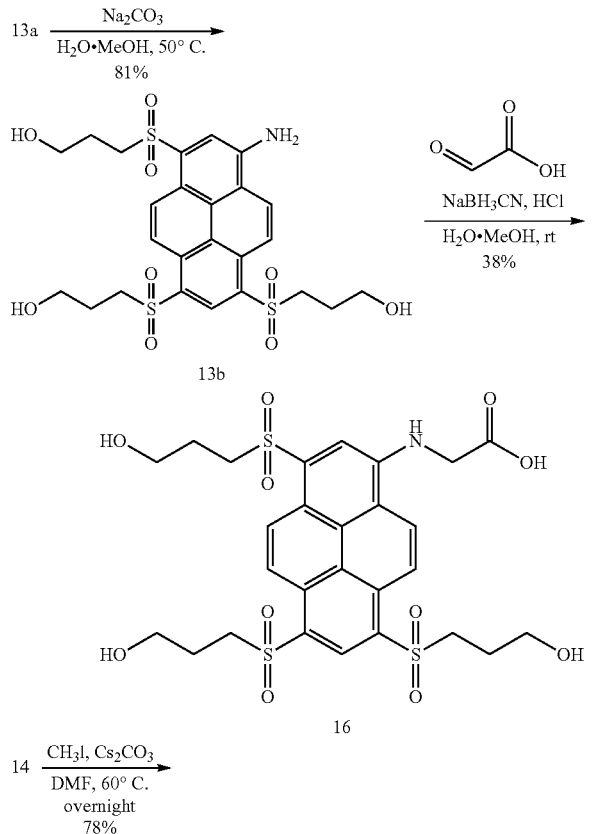

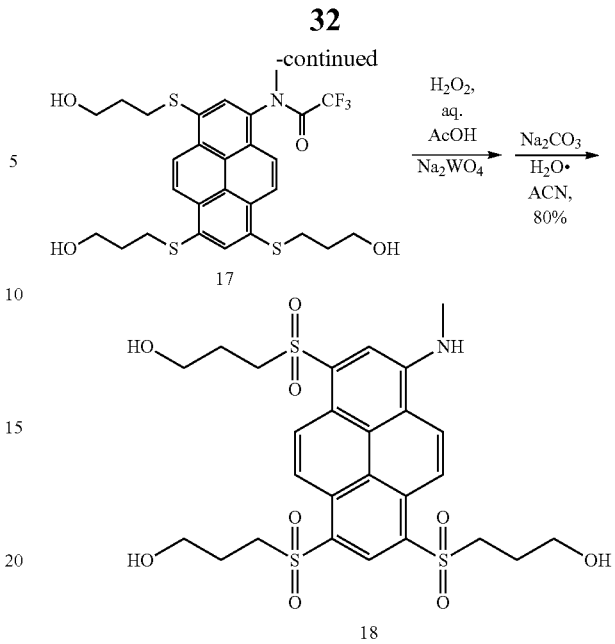

The amino group in tri-sulfone 13a was deprotected by gentle heating in aqueous-methanolic solution of sodium carbonate, and aminosulfone 13b was isolated in a good yield. Reductive amination of aminosulfone 13b with glyoxylic acid monohydrate in the course of Borch reaction (Borch et al., *J. Am. Chem. Soc.* 1969, 91, 3996-3997) led to the pyrene dye 500P (16) with the yield of 38%. The reaction was carried out by addition of sodium cyanoborohydride in portions, glyoxylic acid monohydrate and concentrated aqueous HCl to compound 13b over several days. The moderate yield could be explained by the low reactivity of the amino group deactivated by three electron-withdrawing alkylsulfonyl groups. Compound 16 represents a fluorescent dye with a versatile reactive center—carboxyl group. The amino group in 16 is carboxymethylated, and it was interesting to see what bathochromic and bathofluoric shifts this kind of derivatization (with a less efficient donor than an alkyl group) will induce. N-Methylated pyrene dye 18 was also prepared. Methyl group is a more powerful electron donor than carboxymethyl group, and in this respect, compound 18 probably represents a better model for the product of the reductive amination of carbohydrates than compound 16.

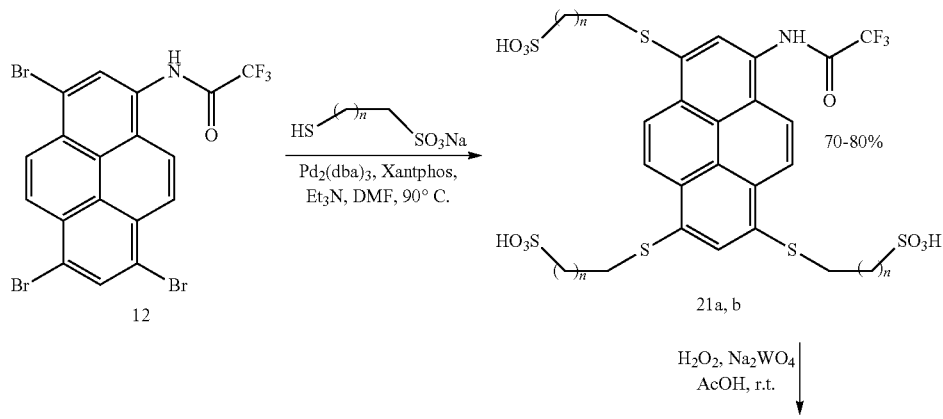

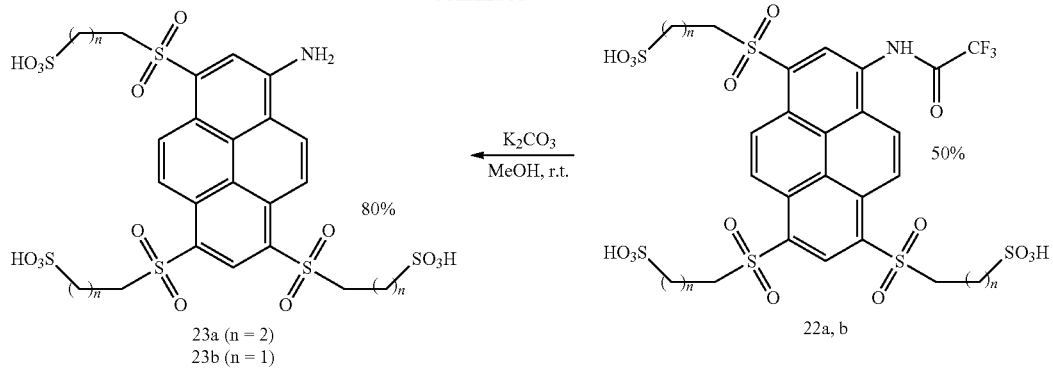

23a (n = 2)
23b (n = 1)

22a, b

The synthesis of alkylsulfonyl-substituted (particularly, sulfoalkylsulfonyl-substituted) 1-aminopyrene dyes 23a and its homolog 23b requires no protection of the sulfonic acid group ($SO_3H$) in the corresponding bifunctional synthone, as depicted in Scheme 11. This greatly simplifies the whole process, compared to that for preparation of its "phosphorylatd counterpart"—dye 15 (see Scheme 9), especially considering that some useful sulfoalkyl-substituted synthones, e. g., sodium 3-mercapto-1-propanesulfonate or sodium 2-mercaptoethanesulfonate, are commercially available. The reaction leads to a highly water-soluble dye, which has three ionizable groups connected to the dye core via thioether functions. Oxidation of the thioether to the sulfone brings a big batochromic and batofluoric shifts relative to the thioether-containing intermediate 21a,b and even to APTS, a well-established benchmark dye (see Schemes 11 and 12 for structures and Table 2 for spectral properties). The cleavage of the protective group at the amino site of the dye leads to the carbohydrate-reactive compounds that represent a case of general Formula C. The whole synthesis sequence is depicted in Scheme 11 above.

Spectral Properties of the New Dyes

TABLE 2

Spectral properties of the phosphorylated aminoacridones 6-H and 6-Me, sulfonylamidopyrenes 8-R (R = H, Me), alkylsulfonyl-modified pyrene dyes 15, 16, 18, 23a, some of their precursors and related compounds (see Schemes 9, 10, 11 and 12 for structures). For selected actual UV/Vis absorbance and fluorescence spectra see also FIG. 2A and FIG. 2B.

| Dye | Absorption, $\lambda_{max}$, nm ($\epsilon$, $M^{-1}$ $cm^{-1}$) | Emission $\lambda_{max}$, nm ($\phi_{fl}{}^a$) | Solvent | Lifetime of excited state ($\tau$, ns) |
|---|---|---|---|---|
| 6-H | 217 (13500), 260 (26000) 295 (28000), 420 (3700) | 485 (excit. 405 nm), 586 (all excit. λ; ~0.05) | $H_2O$ | 22.3 (485 nm em.) 3.7 (585 nm em.) |
| 6-Me | 219 (10300), 263 (18600) 299 (18500), 430 (2900) | 485 and 585 (all excit. 300-470 nm, ~0.06 ) | TEAB[b] | 8.8 (470 nm em.)[c] 2.9 (590 nm em.)[c] |
| 7-H | 477 (22400) | 535 (0.96)[a] | MeOH | 5.6 |
| 7-Me | 493 (23000) | 549 (0.97) | MeOH | 5.9 |
| 8-H | 465 — | 544 (0.88) | $H_2O$ | 5.9 |
| 8-Me | 502 — | 563 (0.85) | $H_2O$ | 3.6 |
| 13b | 486 (21000) | 534 (0.80)[c,d] | MeOH | 4.9 |
| 15 | 477 (19600) | 542 (0.92) | TEAB[b,h] | 5.8 |
| 16 | 499 (18000) | 553 (0.71)[d] | MeOH | 4.9 |
| 18 | 502 (23400) | 550 (0.88) | MeOH | 6.3[f] |
|  | 509 (19500) | 563 (0.67) | $H_2O$ | 6.4[f] |
| APTS[e] | 425 (22000) | 457 (0.95) | PBS |  |
| 19 | 635 (75000) | 655 (0.62) | PBS |  |
| 20 | 581 (120000) | 607 (0.74) | PBS |  |
| 23a | 486[g] (21000) | 542 (0.86)[h] | TEAB[i] |  |

[a]absolute values of the fluorescence quantum yields (if not stated otherwise);
[b]TEAB is aqueous $Et_3N*H_2CO_3$ buffer with pH = 8-8.5;
[c]excitation at 375 nm;
[d]relative value, with Rhodamine 6G as a reference dye with $\phi_{fl}$ = 0.9;
[e]for mono N-alkylated APTS derivatives abs. and emiss. maxima are 457 and 516 nm, respectively ($\epsilon$~19000 $M^{-1}$ $cm^{-1}$);
[f]excitation at 515 nm;
[g]compound 23a is spectrally identical to its homolog 23b;
[h]relative value with fluorescein as a reference dye with $\phi_{fl}$ = 0.9 in 0.1M NaOH under excitation at 496 nm;
[i]switching from TEAB to PBS buffer with pH 7.4 virtually does not affect the spectral properties, i.e., $\phi_{fl}$.

Scheme 12.
Phosphorylated fluorescent dyes 19, 20, sulfonated dyes 23a and APTS as reference compounds possessing large net charged and different spectral properties.

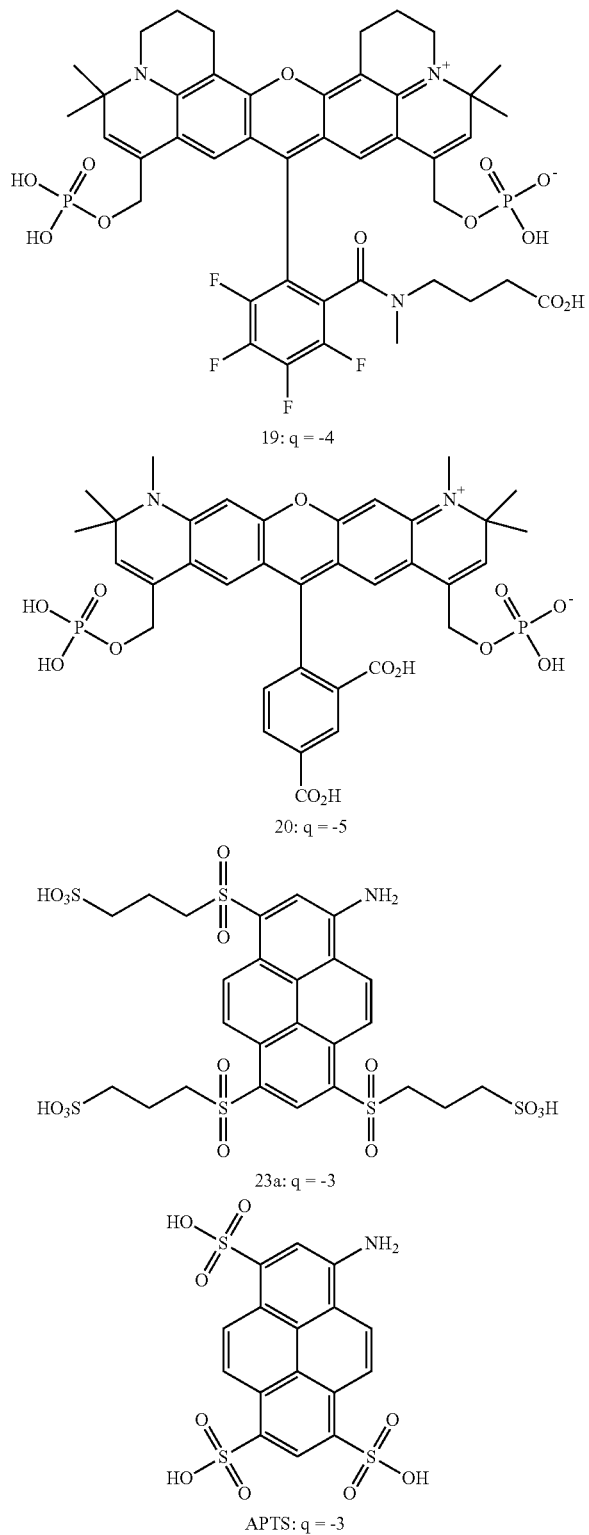

The structural features and spectral data in Table 2 demonstrate that the doubly phosphorylated aminoacridones 6-H and 6-Me, triple phosphorylated pyrene dyes 8-H, 8-Me, and 15 meet the criteria to the fluorescent tags defined above. Additionally, it was necessary to prove if they could be used in reductive amination of glycans, and if the emission of their conjugates would not interfere with the emission of glycans labeled with APTS (for structure and spectral data, see Schemes 9-12 and Table 2). For example, compounds 6-R (R=H, Me) have m/z ratios equal to 134 and 138, respectively (APTS has m/z=151). They have several absorption maxima and emit orange light (with two emission maxima at 485 nm and 585 nm and relative intensities of ca. 1:2; see FIG. 2A). Though their absorption at 488 nm is relatively low, the red-shifted emission is a remarkable feature and is accompanied with a Stokes shift of ca. 160 nm. The absolute values of the fluorescence quantum yields for compounds 6-R are 5-6%. Therefore, in spite of their relatively low brightness, yellow-orange emitting acridone dyes 6-R are potentially at least as useful as the yellow-green emitting aminopyrene dyes 8-R and 15, which are brighter. The dyes of both types represent new tags which can either be used for labelling of glycans, including "heavy" and "exotic" glycans which could not yet been detected due to limitations posed by APTS with its relatively low net charge (−3) and low mobility of the "heavy" carbohydrates decorated with an APTS label. Indeed, due to the presence of four negative charges and extremely low m/z ratio, phosphorylated dyes introduced here are able to provide better electrophoretic mobility of conjugates, reduce their migration times and thus reveal and highlight bulky and massive carbohydrates.

All pyrene dyes listed in Table 2 are highly fluorescent. The non-phosphorylated pyrenes 7-R (R=H, Me), 13b, 16 and 18 allow to estimate the extinction coefficients with higher accuracy. The extinction coefficients of the most long-wavelength bands are in the range of 18000-23000, while the positions of the maxima vary from 465 to 507 nm. Therefore, the fluorescence can be readily induced by the argon ion laser emitting at 488 nm. Emission maxima are found in the range from 535 to 563 nm, and the fluorescence quantum yields are always high (71-97%). Therefore, sulfonated 1-aminopyrenes (general Formulae B-D) represent much brighter dyes than 2-sulfonamido-7-aminoacridones (Formula A). The brightness is proportional to the product of the extinction coefficient (at 488 nm) and fluorescence quantum yield. We can assume that for acridone dyes this value is ca. 1500×0.06=90, and for pyrenes—20000×0.9=18000. This rough estimation means that trisulfonated 1-aminopyrenes are ca. 200 times brighter dyes than 2-sulfonamido-7-aminoacridones. This property makes 1-aminopyrene dyes of the present invention (Formulae B-D) to be superior tags than 2-sulfonamido-7-aminoacridones (Formula A) and APTS. If one assumes that for APTS conjugates the extinction coefficient at the maximum (457 nm) is 19000 (Scheme 3), and the absorption at 488 nm is typically ca. 35% of the maximal absorption at 457 nm, then one obtains the relative brightness of 6000 (assuming the same fluorescence quantum yield). Therefore, the dyes of the present invention are ca. 3 times brighter than APTS under excitation with the 488 nm laser (in conjugates with glycans). Pyrene dyes of the present invention, in particular, compounds 8-H, 15 and 23a,b represent new tags which can be used for labelling of glycans, including "heavy" and "exotic" glycans which could not yet been detected due to limitations posed by APTS its relatively low net charge (−3) and low brightness. Also very importantly, none of those aminopyrene dyes (i. e., 8-H, 13b, 15, 23a,b) showed significant changes in the fluorescence quantum yields while switching from neutral (PBS buffer, pH=7.4) to basic (TEAB buffer, pH=8.0-8.5) medium.

In order to shift the emission band to the red spectral region the N-methylated derivative 8-Me was prepared. This dye possesses a N-methylamino group and therefore, it represents a fluorophore which is very similar to the product of the reductive amination formed from glycans and the parent dye 8-H (compare with compound 6 in Scheme 2). The absorption maximum has been shifted to the red (+37 nm; 8-H→8-Me), but the emission maximum underwent the bathofluoric shift of "only" 19 nm (see Table 2). Thus, the Stokes shift reduced from 79 nm to 61 nm.

There is another tool for increasing bathochromic and bathofluoric shifts in the series of aromatic fluorescent dyes, provided that they possess electron-donor and electron-acceptor groups having the so-called "push-pull" electronic interactions between them (direct polar conjugation). In the case of 1-aminopyrene dyes, the donor group is fixed (and its electron donating properties cannot be enhanced), but the electron-withdrawing groups in positions 3, 6 and 8 may be varied. For example, thioethers in compound 14 (Scheme 9) can be oxidized to the corresponding sulfones and acquire more powerful electron-withdrawing residues than the sulfonamide in compounds 7-R, 8-R and 9-R (Scheme 8). Indeed, alkyl sulfone groups (R—SO$_2$, that is present in compounds 13b, 15, 16, 18 and 23a,b; see Schemes 8, 9 and 11) have the highest values of the Hammett 6-constants, as seen in Table 1, and this indicates that they are even more powerful acceptors than sulfonamide moieties (that is present in compounds 7-H, 7-Me, 8-H, 8-Me; see Schemes 8 and 9). However, after preparing compounds 8-H and 15 and comparing their spectral properties in aqueous solutions (Table 2), it was determined that, as expected, the bathochromic shift was 12 nm, but the position of the emission maximum and the band form are the same (as seen in FIG. 2B). The simplest explanation for that is based on the assumption that the single amino group (as a donor) is "at its limit" and not capable to provide more electron density to the 7-system decorated with three very powerful acceptor groups, however strong they are. Fortunately, upon the reductive alkylation of the nitrogen atom (see Scheme 2), further bathochromic and bathofluoric shifts occurred (compare the spectral data for compounds 8-H and 8-Me discussed above), and compound 15 afforded bright conjugates with glycans.

A further aspect of the present invention relates to a general and straightforward method for synthesizing fluorescent pyrene dyes of Formula C, wherein X at each occurrence is SO$_3$H and n is 1-12, preferably 1-6, which involves an exchange reaction of aryl halogen with bifunctional reagents that have pre-synthesized thioalkyl and unprotected sulfonic acid functions, optionally followed by oxidation of the thioether to the sulfone. Thus, the synthesis yields sulfoalkylsulfonyl-substituted dyes where sulfonic acid group (SO$_3$H) is connected to the aromatic dye core via an alkylsulfonyl (alkanesulfonyl) linker SO$_2$(CH$_2$)$_n$.

More specifically, such a method comprises at least the following steps: 1) protection of 1-aminopyrene with an appropriate protective group; 2) halogenation, usually bromination, as depicted in Scheme 9; 3) cross-coupling reaction, usually catalyzed with palladium or copper salts or complexes, of the trihalogeno-substituted pyrene derivative with a bifunctional reagent with a thiol and sulfonic acid (sulfonate) functions, as depicted in Scheme 11; 4) oxidation of the thioether to the sulfone; 5) deprotection of the amino group.

A closely related aspect of the invention relates to a method for synthesizing fluorescent aminopyrene dyes with absorbance maxima of 477-510 nm, net charge of 0 or down to −6 and larger, emission maxima of 535-560 nm in water, having the general Formulae B and C, particularly compounds 7-R, 13a, 13b, 15, 16, 18, 23a and 23b, which involves an exchange reaction of the aryl halogen to a substituted thioalkyl function, followed by oxidation to the sulfone and, optionally, by phosphorylation at the hydroxyl site.

The present invention further relates to a method for synthesizing phosphorylated fluorescent aminopyrene or aminoacridone dyes with net charges of −4, −6 and larger, that have the general Formulae A and D, particularly compounds 6-R and 8-R, which involves sulfamidation of amino alcohols, followed by phosphorylation at the hydroxyl site.

Figure 1:
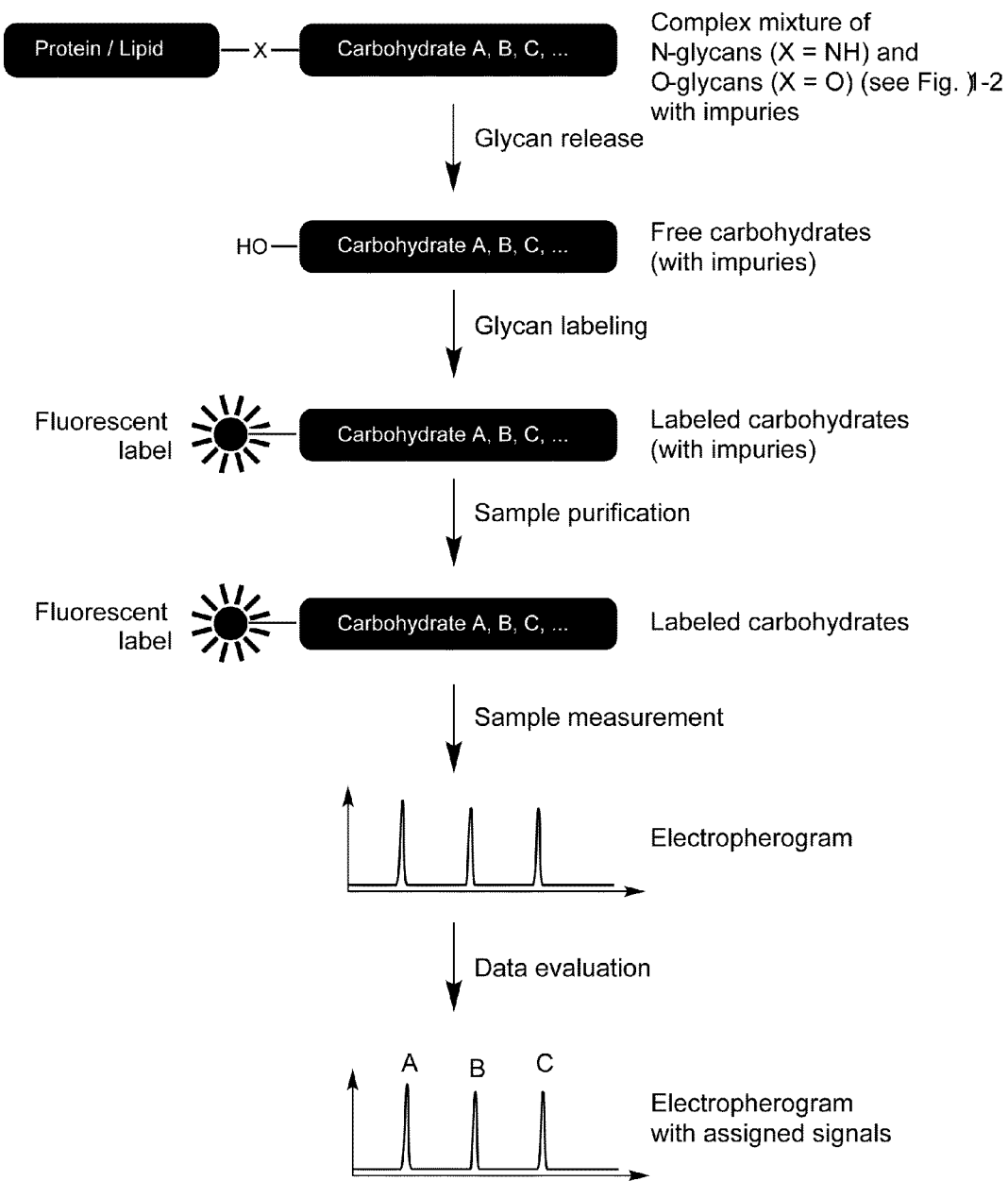
FIG. 1 Principal steps of separation-based glycan analysis.
Figure 2A:
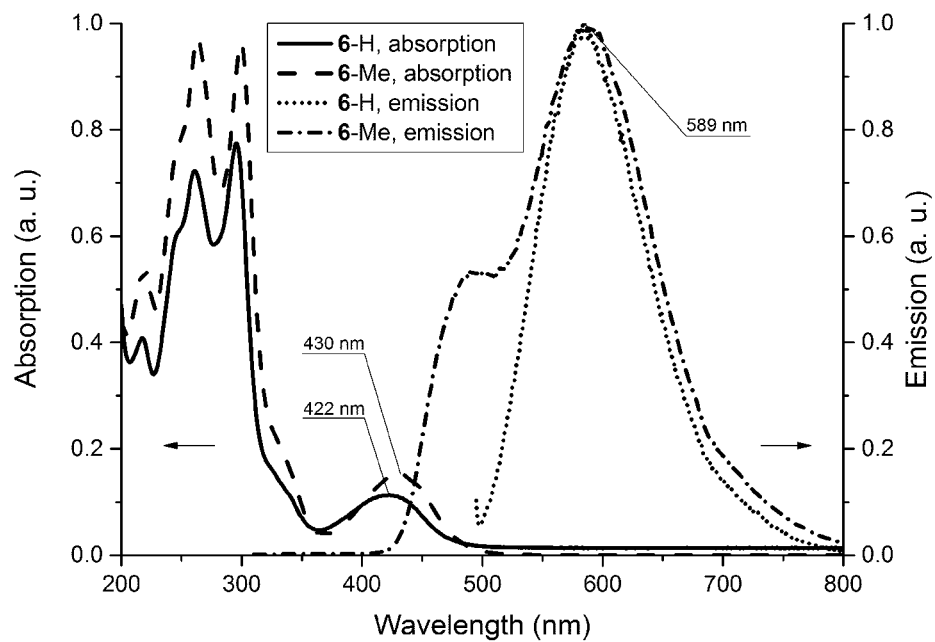
FIG. 2A shows actual normalized absorbance and fluorescence spectra of the new aminoacridone dyes: 6-H, 6-Me in TEAB buffer (pH 8-8.5)
Figure 2B:
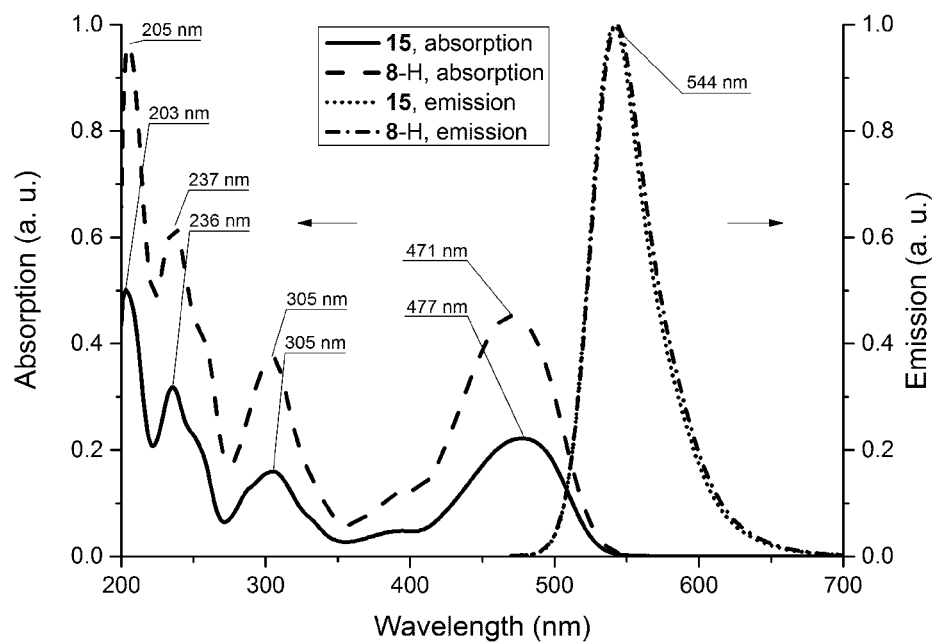
FIG. 2B shows actual normalized absorbance and fluorescence spectra of the new phosphorylated aminoppyrene dyes 8-H and 15 in TEAB buffer (pH 8-8.5)
Figure 3:
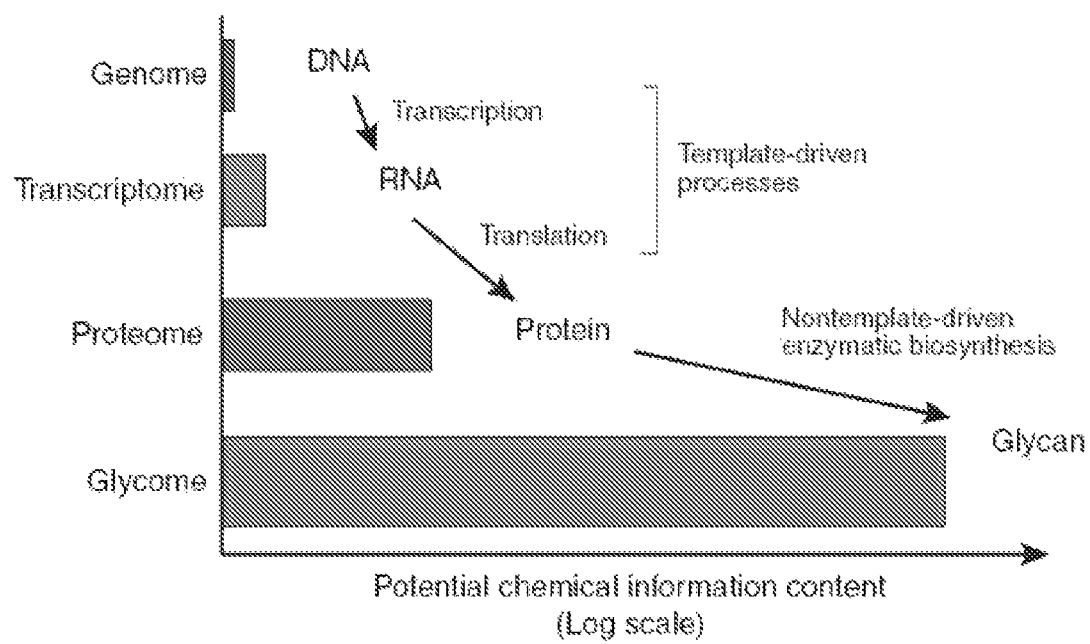
FIG. 3 is a scheme showing the information flow from the genome to the glycome.

The following Examples illustrate the present invention in more detail.

GENERAL MATERIALS AND METHODS 1.1.1 Preparative Methods

If not otherwise stated, reactions were carried out under an argon atmosphere. Solvents met Reag. PhEur purity standard (p.a.). Commercially available substances were used without further purification and purchased from Sigma Aldrich, Acros Organics, Alfa Aesar, ABCR, Merck Millipore, Carbolution Chemicals, etc.

1.1.2 Chromatographic Methods 1.1.2.1 Thin Layer Chromatography (TLC)

Normal phase TLC was performed on silica gel 60 F$_{254}$ (Merck Millipore). For TLC on reversed phase silica gel 60 RP-18 F$_{254}$ (Merck Millipore) was used. Preparative TLC was performed on HPTLC Silica gel 60 F$_{254}$ with concentrating zone 10×2.5 cm (Merck Millipore). Compounds were detected by exposing TLC plates to UV-light (254 or 366 nm). Amines were detected by using ninhydrin solution (0.5% in EtOH).

1.1.2.2 Column Chromatography

Silica gel 60 with a particle size of 40-63 μm was purchased from Merck Millipore. Reversed phase column chromatography was performed on POLYGOPREE® 60-50 C$_{18}$ (Macherey Nagel). Deactivated silica gel 60 was purchased from MP Biomedical. Routine separation was performed with an automated Isolera™ One system (Biotage GmbH) with commercially available cartridges.

1.1.3 Analytical Instruments 1.1.3.1 Absorption Spectroscopy

Absorption spectra were recorded with a double-beam UV-vis spectrophotometer (Varian, series 4000). For the determination of the absorption spectra, quartz cells with a 1 cm path length were used. Emission spectra and fluorescence quantum yield were obtained on a Quantaurus-QY Absolute PL quantum yield spectrometer C11347 (Quantaurus QY) or on a Cary Eclipse fluorescence spectrometer (Varian).

1.1.3.2 Nuclear Magnetic Resonance (NMR)

NMR spectra were recorded on an Agilent 400MR DD2 spectrometer. All spectra are referenced to tetramethylsilane as an internal standard (δ=0.00 ppm) using the signals of the residual protons of CHCl$_3$ (7.26 ppm) in CDCl$_3$, CHD$_2$OD (3.31 ppm) in CD$_3$OD, CHD$_2$COCD$_3$ (2.05 ppm) in (CD$_3$)$_2$CO or DMSO-d$_5$ in DMSO-d$_6$. Multiplicities of the signals are described as follows: s=singlet, br. s=broad singlet, d=doublet, t=triplet, q=quartet, m=multiplet. Coupling constants $^nJ_{x,y}$ are given in Hz, where n is the number of bonds between the coupled nuclei x and y. For $^{13}$C-signals, which were revealed by indirect detection by HSQC, only resonances of the carbon atoms linked to H-atoms were recorded.

1.1.3.3 Mass-Spectrometry (MS)

Low resolution mass spectra (ESI-MS) with electro-spray ionization (ESI) were obtained on a Varian 500-MS spectrometer. High resolution mass spectra (ESI-HRMS) were obtained on a Bruker micro TOF (ESI-TOF-MS) spectrometer.

1.1.3.4 High-Performance Liquid Chromatography (HPLC)

HPLC system (Knauer): Smartline pump 1000 (2×) with 10 mL pump-head, UV detector 2500, column thermostat 4000, mixing chamber, injection valve with a 20 or 50 μL loop for the analytical and 500 μL loop for preparative columns; 6-port-3-channel switching valve; analytical column: Eurospher-100 C18 5 μm (if not stated otherwise), or Kinetex C18 100, 5 μm, 250×4.6 mm, flow 1.2 mL/min; preparative column: Kinetex C18 100, 5 μm, 250×21 mm, flow 10 mL min/mL, solvent A: water+0.1% v/v trifluoroacetic acid (TFA); solvent B: MeCN+0.1% v/v TFA (if not stated otherwise.) For isolation and purification of phosphorylated dyes on preparative scales, acetonitrile-water systems containing 0.05-0.1 M of Et$_3$N*H$_2$CO$_3$ buffer (pH=8-8.9; Sigma-Aldrich, or self-prepared from 1 M aq. Et$_3$N and CO$_2$ gas obtained by evaporation of solid CO$_2$).

Example 1

Synthesis of Fluorescent Acridone Dyes and their Precursors

2-Nitroacridine-9 (10H)-one (1-H)

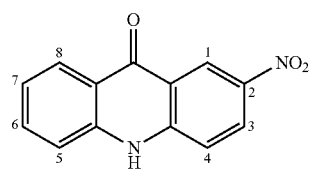

The reaction between 2-chloro-5-nitrobenzoic acid and aniline in the presence of K$_2$CO$_3$ and catalytic amounts of Cu(NO$_2$)$_2$ (185° C., 2-4 h) afforded 4-nitro-N-phenylanthranilic acid according to the procedure described in WO 2007/049057 (3 May 2007) by R. Ramage, B. Maltman, G. Cotton, S. C. M. Couturier, and R. A. S. McMordie; see also: US2012/0015373 (19 Jan. 2012) by J. A. Smith and R. M. West. 4-Nitro-N-phenylanthranilic acid was cyclized to 2-nitroacridine-9 (10H)-one (1-H)(POCl$_3$, reflux, 3 h). $^1$H NMR (400 MHz, DMSO-d$_6$) δ=12.4 (s, 1H, NH), 8.96 (d, J=2.8, 1H, H-1), 8.46 (dd, J=9.2, 2.7 Hz, 1H, H-3), 8.23 (dd, J=8.1, 1.6 Hz, 1H, H-8), 7.81 (ddd, J=8.5, 7.0 and 1.6 Hz, 1H, H-6/7), 7.66 (d, J=9.1 Hz, 1H, H-4), 7.58 (dm, 1H, H-5), 7.37 (ddd, J=8.1, 7.0 and 1.1 Hz, 1H, H-7/6) ppm.

2-Nitro-9-oxo-9,10-dihydroacridine-7-sulfonic acid (2-H)

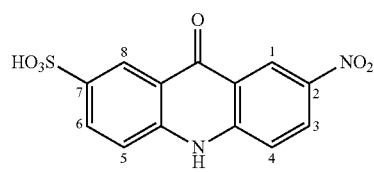

Compound 1-H was dried and sulfonated with a 20% oleum (100° C., 1.5 h) to afford the title compound 2-H (US2012/0015373). For example, to 530 mg (2.21 mmol) of 2-nitro-10H-acridine-9-one (1-H), 20% SO$_3$ in H$_2$SO$_4$ (25 mL) was added dropwise and the reaction mixture was stirred at 100° C. for 90 minutes. Then the reaction mixture was very carefully and slowly poured onto ice (>30 g), and 4 mL of conc. aq. HCl was added. The brown precipitate was separated by centrifugation, washed with 4 M aq. HCl (2×5 mL) and lyophilized. Yield—463 mg (65%) of brown solid. HPLC: $t_R$=5.6 min; H$_2$O/ACN (+0.1% TFA): 80/20→50/50 in 25 min, detection at 254 nm. $^1$H NMR (400 MHz, D$_2$O) δ=7.61 (dd, J=8.0 and 2.6 Hz, 1H, H-3), 7.59 (br. s, 1H, H-1), 7.57 (d, J=2.6 Hz, 1H, H-8), 7.33 (dd, J=8.6 and 2.1 Hz, H-6), 6.53 (dd, J=8.8 and 1.0 Hz, 1H, H-4), 6.47 (d, J=8.6 Hz, 1H, H-5) ppm. ESI-MS (C$_{13}$H$_8$N$_2$O$_6$S, M=320), negative mode: m/z (rel. int., %)=319 (100) [M−H]$^-$.

N,N-(2-Hydroxyethyl)-2-nitro-9-oxo-9,10-dihydroacridine-7-sulfonamide (4-H)

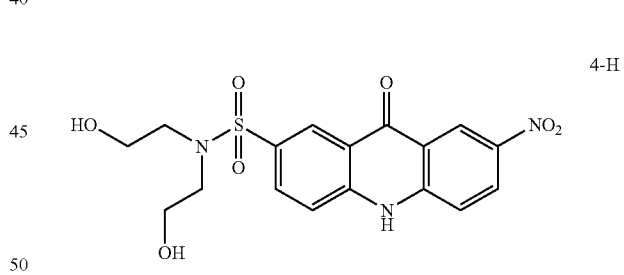

Compound 2-H (55 mg, 0.17 mmol) was cooled down to 0° C. and chlorosulfonic acid (1.7 mL, d=1.75 g/mL, 3.0 g, 26 mmol) was added dropwise. The reaction mixture was stirred at room temperature for 6 h and poured onto ice (7-10 g). The beige precipitate was separated by centrifugation, washed with ice-water (2×5 mL) and dried in vacuo. The obtained sulfonyl chloride was added to a solution of N-methyl ethanolamine (86 mg, 0.80 mmol) in MeCN/H$_2$O (1:1) at 0° C. The reaction mixture was warmed-up to room temperature and stirred at 50° C. overnight. The precipitate dissolved gradually. Yield—33 mg (48%) of a yellow solid which was obtained upon concentration of the reaction mixture in vacuo (in the course of evaporation of acetonitrile). HPLC: $t_R$=16.7 min H$_2$O/CAN (+0.1% TFA): 80/20→50/50 in 25 min, 254 nm. $^1$H NMR (400 MHz, DMSO-d$_6$) δ=12.7 (br. s, 1H, NH), 8.95 (d, J=2.6 Hz, 1H, H-1), 8.55 (d, J=2.2 Hz, 1H, H-8), 8.51 (dd, J=9.2, 2.7 Hz, 1H, H-6), 8.13 (dd, J=8.8, 2.2 Hz, 1H, H-3), 7.72 ("t", J=8.9 Hz, 2H, H-4,5), 4.83 (t, J=5.5 Hz, 2H, OH), 3.51 (q, J=6.3 Hz, 4H, CH$_2$), 3.18 (t, J=6.4 Hz, 4H, CH$_2$) ppm. C$_{17}$H$_{17}$N$_3$O$_7$S, M=407 g/mol; ESI-MS, negative mode: m/z (rel. int., %)=406 (100) [M–H]$^-$.

N,N'-(2-Hydroxyethyl)-2-nitro-9-oxo-9,10-dihydroacridine-7-sulfonamide O,O'-diphosphate (5-H)

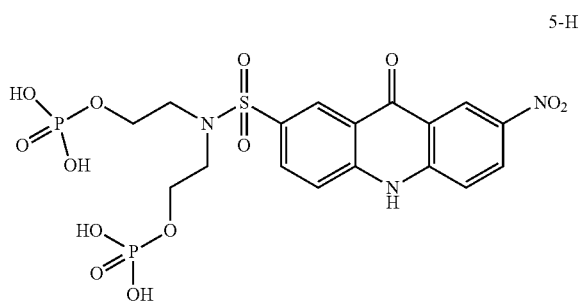 [SMILES: O=c1c2cc([N+](=O)[O-])ccc2[nH]c2ccc(S(=O)(=O)N(CCOP(=O)(O)O)CCOP(=O)(O)O)cc12]

5-H

Compound 4-H (50 mg, 0.12 mmol) was dissolved in 10 mL MeCN, and this solution was added under Ar to 5 mL of freshly distilled POCl$_3$. The suspension was stirred at 30° C. for 2 h. The solvent and the excess of POCl$_3$ were removed in vacuo, the residue was dissolved in aqueous TEAB buffer (1 M), and the title compound was isolated on RP-18 using MeCN—0.05 M aq. TEAB buffer (1:3) as an eluent. Yield—27 mg (40%) of a yellow solid (after lyophilization). HPLC: t$_R$=3.5 min; H$_2$O/ACN (+0.1% TFA): 70/30→0/100 in 25 min, 254 nm. HPLC: t$_R$=9.2 min, H$_2$O/ACN (+0.1% TFA): 80/20→50/50 in 25 min, 254 nm. $^1$H NMR (400 MHz, D$_2$O) δ=8.72 (d, J=2.6 Hz, 1H, H-1), 8.35 (d, J=2.2 Hz, 1H, H-8), 8.24 (dd, J=9.3, 2.6 Hz, 1H, H-6), 7.95 (dd, J=8.9, 2.2 Hz, 1H, H-3), 7.47 (d, J=8.9 Hz, 1H, H-4/5), 7.39 (d, J=9.2 Hz, 1H, H-5/4), 3.84-3.78 (m, 4H, CH$_2$), 3.37 (t, J=5.9 Hz, 4H, CH$_2$). $^{31}$P NMR (81 MHz, D$_2$O): δ=1.0 ppm. C$_{17}$H$_{19}$N$_3$O$_{13}$P$_2$S, M=567 g/mol). ESI-MS, negative mode: m/z (rel. int., %)=566 (100) [M–H]$^-$.

2-Amino-N,N-(2-hydroxyethyl)-9-oxo-9,10-dihydroacridine-7-sulfonamide O,O'-diphosphate (6-H)

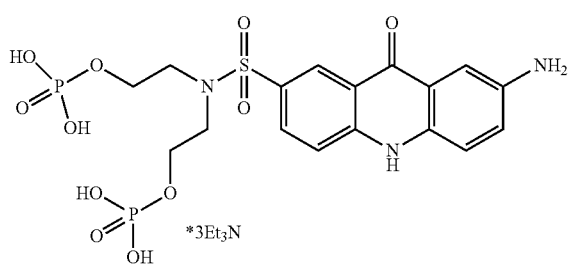

6-H

Pd/C (the oxidized form (VWR International, 10% Pd, 7 mg) was mixed under argon with propanol-2 (attention: Pd/C causes ignition when gets dry in air during the reaction workup, especially filtration!), water (1 mL) was added; the mixture was flushed with hydrogen, and stirred for 30 min. Compound 5-H (27 mg, 0.48 mmol) was dissolved in propanol-2 (0.5 mL), and this solution was added to the suspension of the pre-reduced catalyst. The reaction mixture was stirred overnight in the atmosphere of hydrogen. HPLC control indicated nearly full conversion to a new substance with yellow fluorescence and t$_R$=2.9 min (HPLC area 92%), 8.8 min (7.5%; starting material) H$_2$O/ACN (+0.1% TFA): 80/20→50/50 in 25 min, 254 nm. The reaction mixture was flushed with argon, the catalyst was separated by centrifugation, washed with aqueous propanol-2, and the combined supernatant was concentrated in vacuo. The title compound was isolated by preparative HPLC (see below). C$_{17}$H$_{21}$N$_3$O$_{11}$P$_2$S (exact mass 537.0372), ESI-MS, negative mode: m/z (rel. int., %)=536 (100) [M–H]$^-$. ESI-HRMS: 536.0278 (found [M–H]$^-$), calculated: 536,0299. Final purification (for reductive amination of sugars) was achieved by preparative HPLC using an aqueous 0.05 M TEAB buffer (pH 8) and Kinetex column (5 μm C18 100, 250×10 mm), ACN/H$_2$O: 5/95-30/70 in 20 min, 4 mL/min; t$_R$~10-11 min (strongly depends on concentration of the analyte). Purity control: 0.05 M TEAB aqueous buffer (pH 8) and Kinetex column (5 μm C18 100, 250×4.6 mm), ACN/H$_2$O: 5/95-50/50 in 20 min, 1.2 mL/min; t$_R$=8.1 min. $^1$H NMR (400 MHz, D$_2$O) δ=8.35 (d, J=2.2 Hz, 1H, H-8), 7.82 (dd, J=9.3 and 2.6 Hz, 1H, H-6), 7.29 (d, J=9.3, 1H, H-5), 7.12 (d, J=2.2 Hz, 1H, H-1), 7.04 (dd, J=2.4 and 8.9 Hz, 1H, H-3), 7.01 (d, J=8.9 Hz, 1H, H-4), 3.87 (q, J=6.0, 4H, (OH)$_2$POCH$_2$), 3.40 (t, J=5.9 Hz, 4H, NCH$_2$), 3.05 (q, ~16H, CH$_2$N in Et$_3$N), 1.13 (t, ~23H, CH$_3$ in Et$_3$N) ppm. λ$_{max}$ (absorption, H$_2$O (ε, M$^{-1}$ cm$^{-1}$)=217 (13500), 260 (26000), 295 (28000), 420 (3700) nm; λ$_{max}$ (emission, H$_2$O)=485 nm (excitation at 405 nm), 586 nm (excitation at 300 nm, 420 nm or 470 nm); fluorescence lifetimes—22.3 ns (excitation at 405 nm, emission detected at 485 nm) and 3.7 ns (excitation at 470 nm, emission detected at 585 nm).

10-Methyl-2-nitroacridin-9 (10H)-one (1-Me)

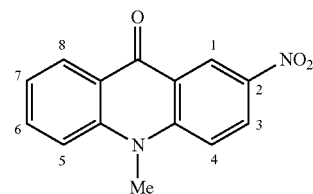

1-Me

NaH (600 mg of a 60% suspension in mineral oil; 360 mg, 15 mmol) was washed with dry pentane (3×15 mL) under argon atmosphere, suspended in dry DMSO, and then 2-nitroacridine-9 (10H)-one (1-H, 2.5 g, 10.4 mmol) was added to this suspension in small portions. The organic substance dissolves gradually, and the solution turned magenta (violet). It was warmed-up to 50-60° C., stirred for 30 min, cooled to room temperature, and then MeI (4 mL, 64 mmol) was added to the reaction mixture. In the course of stirring overnight at room temperature, the suspension gradually turned yellow. Then the reaction mixture was poured onto ice with water (75 mL). The precipitate was collected by filtration, washed with water, and recrystallized from AcOH (200 mL). Yield—2.1 g (80%) of a yellow solid. HPLC: t$_R$=13.9 min A/B: 70/30→0/100 in 25 min, 254 nm. C$_{14}$H$_{10}$N$_2$O$_3$, M=254 g/mol). ESI-MS, positive mode: m/z (rel. int., %)=277.0579 (100) [found M+Na]$^+$; 277.0584 (calculated). $^1$H NMR (400 MHz, DMSO-d$_6$) δ=9.01 (d, J=2.9, 1H, H-1), 8.50 (dd, J=9.6, 2.9 Hz, 1H, H-3), 8.32 (ddd, J=7.9, 1.6, 0.7 Hz, 1H, H-8), 8.02 (d, J=9.6 Hz, 1H, H-4), 7.95-7.85 (m, 2H, H-6/7), 7.44 (ddd, J=8.0, 6.2, 1.7 Hz, 1H, H-5), 3.98 (s, 3H, CH₃) ppm.

10-Methyl-2-nitro-9-oxo-9,10-dihydroacridine-7-sulfonic acid (2-Me)

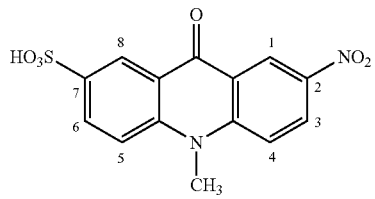

To compound 1-Me (400 mg, 1.57 mmol), 20% SO₃ in H₂SO₄ (7.2 mL, 16.8 mmol) was added dropwise, and the reaction mixture was stirred at 100° C. for 90 min. Then the reaction mixture was poured very carefully and slowly onto ice (>30 g), and 4 mL of conc. HCl was added. The brown precipitate was separated by centrifugation, washed with cold 4 M HCl (2×5 mL) and lyophilized. Yield—376 mg (72%) of the title compound as a brown solid. HPLC: $t_R$=7.9 min A/B: 80/20→50/50 in 25 min, 254 nm. ¹H NMR (400 MHz, DMSO-d₆): δ=9.03 (d, J=2.9 Hz, 1H, H-1), 8.55 (d, J=2.1 Hz, 1H, H-8), 8.52 (dd, J=9.5, 2.9 Hz, 1H, H-3), 8.08-8.02 (m, 2H, H-4, H-6), 7.90 (d, J=9.1 Hz, 1H, H-5), 4.00 (s, 3H, CH₃) ppm. $C_{14}H_{10}N_2O_6S$, M=334 g/mol. ESI-MS, negative mode: m/z (rel. int., %)=333 (100) [M−H]⁻. ¹H NMR (100 MHz, DMSO-d₆): δ=176.7 (CO), 146.2, 143.3, 142.6, 141.2, 132.8, 128.1, 123.8, 123.3, 121.4, 121.0, 118.8, 117.3, 35.3 (N-Me) ppm.

N,N-(2-Hydroxyethyl)-10-methyl-2-nitro-9-oxo-9,10-dihydroacridine-7-sulfonamide (4-H)

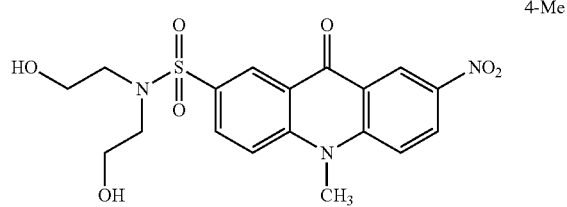 [SMILES: Cn1c2ccc([N+](=O)[O-])cc2c(=O)c2cc(S(=O)(=O)N(CCO)CCO)ccc21]

To compound 2-Me (62 mg, 0.19 mmol), chlorosulfonic acid (3.5 mL, 53 mmol) was added dropwise at 0° C. The reaction mixture was stirred at 50° C. for 30 min and at room temperature overnight. Then the reaction mixture was dropwise poured into ice (10 g), and the beige precipitate separated by centrifugation. It was washed with ice-water (2×10 mL) and lyophilized. The obtained sulfonyl chloride was added to the solution of diethanolamine (185 mg, 1.76 mmol) in THF (2 mL) at 0° C. The reaction mixture was stirred at room temperature overnight. The precipitate was separated by centrifugation, washed with ice water and lyophilized. Yield—57 mg (70%) of the title product as a yellow solid. HPLC: $t_R$=16.9 min A/B: 80/20→50/50 in 25 min, 254 nm. ESI-MS, positive mode: m/z (rel. int., %)=444 (100) [M+Na]⁺. $C_{18}H_{19}N_3O_7S$, M=421 g/mol. ESI-MS, positive mode: m/z=422.1005 [found M+H]⁺; 422.1016 (calculated); 444.0829 [found M+Na]⁺; 444.0836 (calculated). ¹H NMR (400 MHz, DMSO-d₆): δ=8.99 (d, J=2.8 Hz, 1H, H-1), 8.61 (d, J=1.6 Hz, 1H, H-8), 8.56 (dd, J=9.5 and 2.9 Hz, 1H, H-3), 8.19 (dd, J=9.1, 2.4 Hz, 1H, H-6), 8.10 ("d", J=9.4 Hz, 2H, H-4,5), 4.82 (t, J=5.5 Hz, 2H, OH), 4.02 (s, 3H, NMe), 3.52 (q, J=6.0 Hz, 4H, OCH₂), 3.20 (t, J=6.3 Hz, 4H, NCH₂) ppm.

N,N-(2-Hydroxyethyl)-9,10-dihydro-9-oxo-10-methyl-2-nitroacridine-7-sulfonamide O,O'-diphosphate (5-Me)

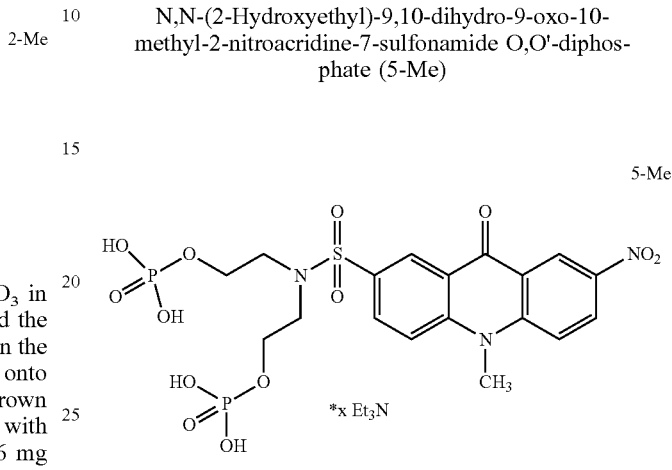

To a solution of 4-Me (31 mg, 73 μmol) in trimethyl phosphate (0.5 mL) POCl₃ (0.2 mL) was added under Ar at 0° C. The suspension was stirred at room temperature for 2 hours. Then the solvent and the excess of POCl₃ were removed in vacuo the residue was diluted with an excess of aq. Et₃N—H₂CO₃ buffer (pH 7.5) and kept at 4° C. overnight. The title compound was isolated on RP-18 using MeCN—0.1 M aq. Et₃N—H₂CO₃ buffer (1:5) as an eluent, lyophilized and used in the final reduction step (see below). $C_{18}H_{21}N_3O_{13}P_2S$, M=581 g/mol. ESI-MS, negative mode: m/z (rel. int., %)=580.0191 (100) [found M−H]⁻; 580.0198 (calculated).

2-Amino-N,N'-(2-hydroxyethyl)-9,10-dihydro-9-oxo-10-methylacridine-7-sulfonamide O,O'-diphosphate (6-Me)

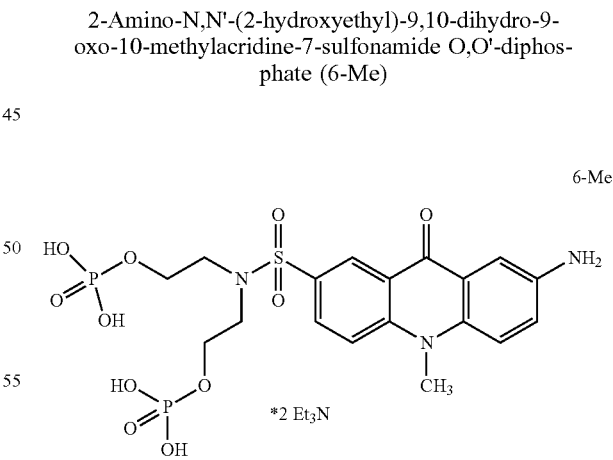

Pd/C(VWR International, the oxidized form, 10% Pd) 7 mg of was mixed under argon with propanol-2, water (1 mL) was added; the mixture was flushed with hydrogen, and stirred for 30 min. Compound 5-Me (27 mg) was dissolved in propanol-2 (0.5 mL), and this solution was added to the suspension of the pre-reduced catalyst. The reaction mixture was stirred overnight in the atmosphere of hydrogen. HPLC control indicated nearly full conversion to a new substance with yellow fluorescence and $t_R$=16.1 min (HPLC area 95%), 19.2 min (5%; starting material?) H$_2$O/ACN (+0.05 M Et$_3$N*H$_2$CO$_3$ buffer in aqueous phase): 99/1→80/20 in 20 min, dioden array detector, Kinetex column 5 μm C18 100, 4.6×250 mm, 20° C., 1.2 mL/min. The reaction mixture was flushed with argon, the catalyst was separated by centrifugation, washed with aqueous propanol-2, and the combined supernatant was concentrated in vacuo. The title compound was isolated by preparative HPLC using an aqueous 0.05 M TEAB buffer (pH 8) and Kinetex column (5 μm C18 100, 250×10 mm), ACN/H$_2$O: 5/95-30/70 in 20 min, 4 mL/min; $t_R$~11.4 min. C$_{18}$H$_{23}$N$_3$O$_{11}$P$_2$S (exact mass 551.0529). ESI-MS, negative mode: m/z (rel. int., %)=550 (100) [M–H]$^-$. ESI-HRMS: 550.0441 (found [M–H]$^-$), calculated: 550, 0456. $^1$H NMR (400 MHz, D$_2$O): δ=8.29 (d, J=2.4 Hz, 1H, H-8), 7.84 (dd, J=9.3 and 2.4 Hz, 1H, H-6), 7.43 (d, J=9.3, 1H, H-5), 7.12 (d, J=9.3 Hz, 1H, H-3), 7.03 (d, J=2.8 Hz, 1H, H-1), 6.97 (dd, J=9.2 and 2.8 Hz, 1H, H-4), 3.85 (q, J=6.1, 4H, POCH$_2$), 3.49 (s, 3H, NMe), 3.37 (t, J=5.9 Hz, 4H, NCH$_2$), 3.04 (q, ~14H, CH$_2$N in Et$_3$N), 1.13 (t, ~20H, CH$_3$ in Et$_3$N) ppm. $^{31}$P NMR (162 MHz, CDCl$_3$): δ=1.1 ppm. $\lambda_{max}$ (0.05 M aq Et$_3$N*H$_2$CO$_3$ buffer, pH 8, c, M$^{-1}$ cm$^{-1}$)=219 (10 300), 263 (18 600), 299 (18 500), 430 (2900) nm; $\lambda_{max}$ (emission, 0.05 M aq Et$_3$N*H$_2$CO$_3$ buffer, pH 8)=485 nm and 585 nm (two maxima in ca. 1:2 ratio, independent from excitation wavelength which may be at 300 nm, 420 nm or 470 nm); fluorescence quantum yield: 5-6% (absolute value).

Example 2

Synthesis of Fluorescent 1-Aminopyrene Dyes and their Precursors

3-Aminopyrene-1,6,8-trisulfonic acid trisodium salt (APTS) was prepared from 1-aminopyrene and a 20% oleum in the presence of Na$_2$SO$_4$ as described by Z. Sharrett, S. Gamsey, L. Hirayama, B. Vilozny, J. T. Suri, R. A. Wessling, B Singaram, *Org. Biomol. Chem.* 2009, 7, 1461-1470.

3-Amino-N,N',N''-tris(2-hydroxyethyl)-N,N',N''-trimethylpyrene-1,6,8-trisulfonamide (7-H)

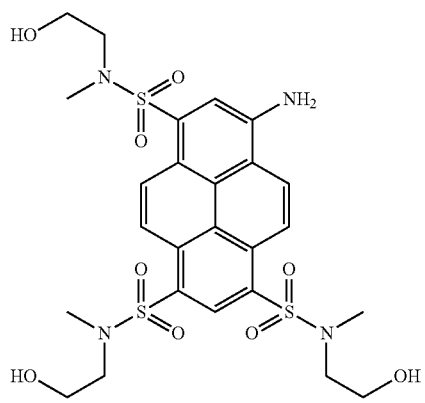

7-H 446 mg (0.98 mmol) of APTS (trisodium salt) was cooled down to 0° C. in an ice bath, and then chlorosulfonic acid (7.5 mL, 0.11 mol) was added dropwise with stirring. The reaction mixture was stirred at 65° C. for 3 h. After cooling down to room temperature, the reaction mixture was transferred onto crushed ice. The red precipitate of trisulfonyl chloride was isolated by centrifugation, washed with ice-water (2×10 mL) and added to a solution of N-methylethanolamine (1.0 g, 13 mmol) in aqueous acetonitrile (1:1, 25 mL) at 0° C. The reaction mixture was vigorously stirred at room temperature, until it became homogeneous, and then lyophilized. The title compound was isolated by chromatography on SiO$_2$ (100 g) with CHCl$_3$/MeOH/H$_2$O (80:18:2) mixture as an eluent. Yield—252 mg (41%) of a brown-orange solid obtained after the second chromatographic purification. HPLC: $t_R$=15.8 min, ACN/H$_2$O: 20/80-50/50 in 25 min, 1.2 mL/min, 254 nm. C$_{25}$H$_{32}$N$_4$O$_9$S$_3$ (exact mass 628.1331); ESI-HRMS: 651.1212 (found [M+Na]$^+$), calculated: 651,1224. $^1$H NMR (400 MHz, CD$_3$OD) δ=9.19 (d, J=9.8 Hz, 1H), 9.06 (s, 1H), 8.99 (d, J=9.6 Hz, 1H), 8.82 (d, J=9.8 Hz, 1H), 8.74 (d, J=9.7 Hz, 1H), 8.18 (s, 1H), 3.69 (m, 6H, CH$_2$), 3.42 (m, 6H, CH$_2$), 3.04 (s, 3H, NCH$_3$), 3.01 (s, 6H, 2×NCH$_3$) ppm; $\lambda_{max}$ (absorption)=477 nm (ε=22 400 M$^{-1}$ cm$^{-1}$, MeOH), max (emission)=535 nm (MeOH, excitation at 470 nm); fluorescence lifetime 5.6 ns (MeOH); fluorescence quantum yield (0.96; absolute value in MeOH).

3-Amino-N,N',N''-tris(2-hydroxyethyl)-N,N',N''-trimethyl-pyrene-1,6,8-trisulfonamide O,O',O''-triphosphate tris(triethylammonium salt) (8-H)

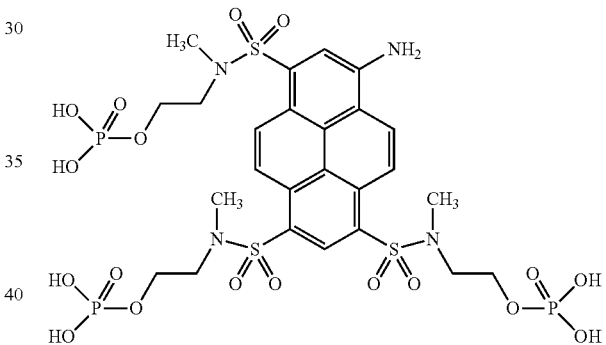

8-H

Compound 7-H (40 mg, 64 μmol) was dissolved in (MeO)$_3$PO (5 mL) and this solution was added to freshly distilled POCl$_3$ (0.2 mL) with stirring at room temperature. A weak exothermic reaction was observed, and the solution turned orange-brown. The reaction mixture was stirred several hours at room temperature. All volatile materials (excess of POCl$_3$ and most of trimethyl phosphate) were removed in vacuum (first using rotary evaporator and then—oil pump; 0.5 mbar, 60° C., cold trap cooled with dry ice for collecting trimethyl phosphate and POCl$_3$). The residue was treated and stirred with 1 M Et$_3$N*H$_2$CO$_3$ buffer (TEAB; initial pH=8), and the pH was controlled. Phosphorylation of the amino group also takes place, but this phosphate group is readily cleaved. Fresh portions of the TEAB buffer were added when the solution became acidic, until the pH stabilized at about 5-7. TLC control on regular SiO$_2$ was possible in iPrOH/H$_2$O/25% aq. NH$_3$ (10/5/1); R$_f$~ 0.3 (yellow spot with green fluorescence). The reaction mixture was lyophilized, and the title compound was isolated by chromatography on regular SiO$_2$ using iPrOH/H$_2$O/25% aq. NH$_3$ (10/5/1) mixture as an eluent. HPLC control indicated homogeneous fractions containing the substance with $t_R$=10.2 min (ACN/H$_2$O (+0.1% TFA): 20/80-50/50 in 25 min, 1.2 mL/min, 254 nm). Lyophilization afforded 60 mg of the red-orange foam. C$_{25}$H$_{35}$N$_4$O$_{18}$P$_3$S$_3$ (exact mass 868.0321)*×NH$_3$ ESI-MS, negative mode: m/z (rel. int., %)=867 (100) [M−H]$^-$, 889 (60) [M−2H+Na]$^-$.

Final purification was achieved by preparative HPLC using a 0.1 M TEAB buffer and a preparative Kintex column (e.g., Kinetex, 5 μm C18 100, 250×4.6 mm, ACN/H$_2$O: 10/90-30/70 in 20 min, 1.2 mL/min; t$_R$=10.8 min). Freeze-drying of the eluate gave the title compound as yellow foam. $^1$H NMR (400 MHz, CD$_3$OD) δ=9.14 (d, J=9.7 Hz, 1H), 9.03 (s, 1H), 8.96 (d, J=9.7 Hz, 1H), 8.77 (d, J=9.8 Hz, 1H), 8.67 (d, J=9.7 Hz, 1H), 8.17 (s, 1H), 3.94-4.06 (m, 6H, CH$_2$), 3.49-3.59 (m, 6H, CH$_2$), 3.08 (s, 3H, NCH$_3$), 3.04 (q, J=7.3 Hz, 18H, CH$_2$N in Et$_3$N), 3.02 (s, 3H, NCH$_3$), 1.22 (t, J=7.3 Hz, 27H, CH$_3$CH$_2$ in Et$_3$N) ppm; λ$_{max}$ (absorption)=205, 237, 305 and 471 nm (0.05 M aq Et$_3$N*H$_2$CO$_3$ buffer, pH 8), λ$_{max}$ (emission)=544 (0.05 M aq Et$_3$N*H$_2$CO$_3$ buffer, pH 8); fluorescence lifetime 5.9 ns (in H$_2$O; excitation at 470 nm); fluorescence quantum yield: 0.77 (H$_2$O, standard: Coumarin 153 with emission efficiency of 0.54 in ethanol, λ$_{excit}$=400 nm), 0.88 (absolute value in 0.05 M aq Et$_3$N*H$_2$CO$_3$ buffer, pH 8; excitation at 460 nm).

3-(Trifluoroacetyl)amino-N,N',N"-tris(2-hydroxy-ethyl)-N,N',N"-trimethylpyrene-1,6,8-trisulfonamide (9-H)

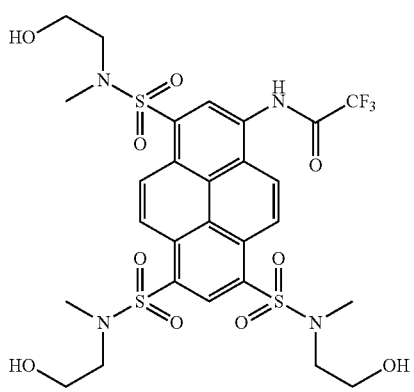

9-H

Compound 7-H (179 mg, 0.28 mmol) was suspended in 10 mL of DCM, and a 10% solution of trifluoroacetic anhydride in DCM (d=1.33 g/mL, 0.9 mL, ~0.57 mmol) followed by Et$_3$N (126 μL, d=0.73 g/mL, 0.91 mmol) was added at room temperature. The reaction mixture was stirred for 30 min. All volatile materials were evaporated under reduced pressure, the residue was dissolved in methanol (50 mL) and NaHCO$_3$ (50 mg) was added. After stirring at room temperature for 30 min, the reaction mixture was neutralized with acetic acid, and all volatile materials were removed in vacuo. These operations remove trifluoroacetate groups from hydroxyl groups. The title compound was isolated by chromatography regular silica gel (50 g) using CH$_2$Cl$_2$/aceton (2:1) as an eluent. Yield—165 mg (82%) of a yellow solid. HPLC: t$_R$=10.8 min, ACN/H$_2$O: 20/80-100/0 in 25 min, 254 nm. C$_{27}$H$_{31}$F$_3$N$_4$O$_{10}$S$_3$, (exact mass 724.1154). ESI-MS, negative mode: m/z (rel. int., %)=723 (100) [M−H]$^-$. $^1$H NMR (400 MHz, acetone-d$_6$) δ=11.2 (br. s, 1H, NH), 9.49 (d, J=10.0 Hz, 1H), 9.38 ("dd", J=9.7 and 1.9 Hz, 2H), 9.26 (s, 1H), 9.02 (s, 1H), 8.76 (d, J=9.7 Hz, 1H), 3.83-3.90 (m, 3H, OH), 3.71 (m, 6H, OCH$_2$), 3.43 (m, 6H, NCH$_2$), 3.08/3.06/3.06 (3×s, Σ 9H, NMe) ppm. $^{19}$F NMR (376 MHz, acetone-d$_6$) δ=−75.7 ppm 3-[N-methyl-N-(trifluoroacetyl)]amino-N,N',N"-tris (2-hydrox-yethyl)-N,N',N"-trimethylpyrene-1,6,8-trisulfonamide (9-Me)

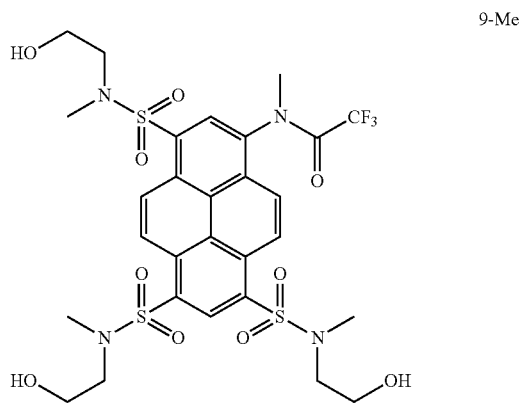 [SMILES: CN(C(=O)C(F)(F)F)c1cc(S(=O)(=O)N(C)CCO)c2ccc3c(S(=O)(=O)N(C)CCO)cc(S(=O)(=O)N(C)CCO)c4ccc1c2c43]

9-Me

To a solution of compound 7-H (120 mg, 0.17 mmol) in DMF (2 mL), CsCO$_3$ (42 mg, 0.13 mmol) and CH$_3$I (960 mg, 6.7 mmol) were added under argon. The reaction mixture was stirred at 70° C. for 40 min, and the solvent was evaporated under reduced pressure. The title compound was isolated by chromatography on regular SiO$_2$ (50 g) using a 15:1 mixture of DCM and methanol as an eluent; yield—110 mg (88%) of a yellow solid. Due to the presence of the secondary amide group, two rotamers (two sets of signals) were detected in $^1$H NMR spectrum of this substance, and therefore it was difficult to interpret. HPLC: t$_R$=12.2 min, ACN/H$_2$O: 20/80-100/0 in 25 min, 254 nm. C$_{28}$H$_{33}$F$_3$N$_4$O$_{10}$S$_3$ (exact mass 738.1311). ESI-MS, positive mode: m/z (rel. int., %)=739 (100) [M+H]$^+$, 761 (35) [M+Na]$^+$.

3-Methylamino-N,N',N"-tris(2-hydroxyethyl)-N,N', N"-trimethylpyrene-1,6,8-trisulfonamide (7-Me)

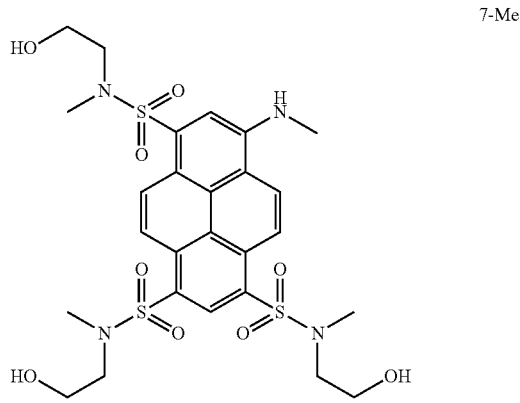 [SMILES: CNc1cc(S(=O)(=O)N(C)CCO)c2ccc3c(S(=O)(=O)N(C)CCO)cc(S(=O)(=O)N(C)CCO)c4ccc1c2c43]

7-Me

The title compound was obtained from the corresponding N-methyl-N-trifluoroacetamide (9-Me; see above) upon treatment with Na$_2$CO$_3$, which was taken in excess as a saturated solution, in aqueous methanol (ca. 1:1) so that reaction mixture remained homogeneous. The product was isolated as an orange solid (20 mg) by chromatography on SiO$_2$ using a 15:1 mixture of DCM and methanol as an eluent.

$^1$H NMR (400 MHz, CD$_3$OD) δ=9.15 (d, J=9.8 Hz, 1H), 9.06 (s, 1H), 8.98 (d, J=9.6 Hz, 1H), 8.77 (d, J=9.8 Hz, 1H), 8.63 (d, J=9.7 Hz, 1H), 7.93 (s, 1H), 3.77-3.63 (m, 6H, CH$_2$), 3.40 (m, 6H, CH$_2$), 3.21 (s, 3H, NCH$_3$), 3.00 (s, 3H, NCH$_3$), 2.99 (s, 6H, 2×NCH$_3$) ppm; C$_{26}$H$_{34}$N$_4$O$_9$S$_3$ (exact mass 642.1488). HRMS (ESI): 665.1353 (found [M+Na]$^+$), calculated: 665.1380. λ$_{max}$(absorption)=493 nm (ε=23000 M$^{-1}$ cm$^{-1}$, MeOH), λ$_{max}$ (emission)=549 nm (MeOH); fluorescence lifetime 5.9 ns (MeOH), fluorescence quantum yield: 0.97 (absolute value in MeOH); 0.83 (relative value obtained in MeOH using Rhodamine 6G as a standard (QY=0.94 in ethanol), excitation at 480 nm).

3-Methylamino-N,N',N''-tris(2-hydroxyethyl)-N,N', N''-trimethylpyrene-1,6,8-trisulfonamide O,O',O''-triphosphate (8-Me) as tris(triethylammonium salt)

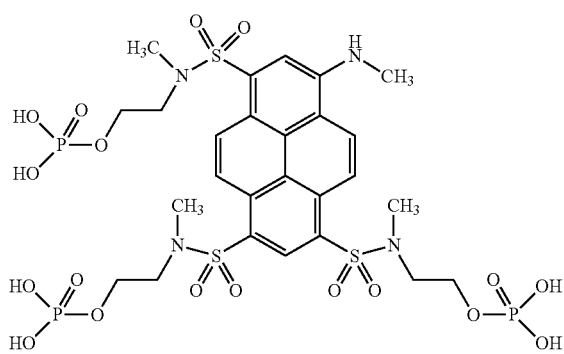

8-Me

To a solution of POCl$_3$ (74 mg, 480 μmol) in 0.1 mL of (MeO)$_3$PO, the solution of compound 7-Me (40 mg, 54 μmol) in 0.5 mL of (MeO)$_3$PO was added dropwise at 0° C. Then the reaction mixture was stirred for 1.5 h at room temperature. All volatile materials (excess of POCl$_3$ and most of trimethyl phosphate) were removed in vacuum (first, using rotary evaporator and then an oil pump; 0.5 mbar, 60° C., cold trap cooled with dry ice for collecting trimethyl phosphate). The residue was treated and stirred with 1 M Et$_3$N*H$_2$CO$_3$ buffer (TEAB; initial pH=8) and pH-value was controlled. Fresh portions of the TEAB buffer were added when the solution became acidic, until the pH-value stabilized at about 5-7. Then the reaction mixture was loaded on RP-18 (ca. 30 g) and the title compound was eluted using 1:4 mixture of MeCN and aqueous 0.1 M Et$_3$N*H$_2$CO$_3$ buffer (pH 7.5). Yield—63%, a yellow solid. HPLC: t$_R$=6.9 min H$_2$O/ACN (+0.1% TFA): 80/20→0/100 in 25 min, 254 nm. C$_{26}$H$_{37}$N$_4$O$_{18}$P$_3$S$_3$ (exact mass 882,0478). ESI-MS, negative mode: m/z (rel. int., %)=881 (100) [M−H]$^-$, 440 (15) [M−2H]$^{2-}$. λ$_{max}$ (absorption)=502 nm (H$_2$O), λ$_{max}$ (emission)=563 nm (H$_2$O); fluorescence quantum yield 0.85 (H$_2$O, standard: Rhodamine 6G with emission efficiency of 0.94 in ethanol, λ$_{excit}$=500 nm). This substance was found to be unreactive in the reductive amination of sugars.

2,2,2-Trifluoro-N-(pyren-1-yl) acetamide (11)

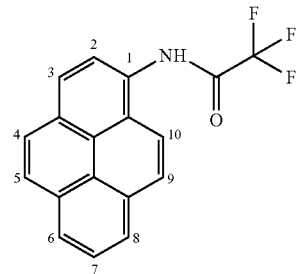

11

1-Aminopyrene (10)(1.00 g, 4.60 mmol) was dissolved in dry DCM (30 mL) under stirring and by using an ultrasonic bath. Trifluoroacetic anhydride (d=1.51, 772 μL, 1.17 g, 5.55 mmol, 1.21 eq.) was added dropwise over a period of 10 min. The obtained suspension was stirred for 30 min at r.t. The precipitate was removed by filtration and washed with cyclohexane (3×15 mL) and dried in vacuo. A white precipitate observed in the filtrate and was also filtered off. The combined precipitates (a light grey powder) represented the title compound (1.13 g, 3.61 mmol, 79%). $^1$H NMR (400 MHz, aceton-d$_6$): δ=8.11 (t, $^3$J$_{H,H}$=7.6 Hz, 1H, 7-H), 8.20 (d, $^3$J$_{H,H}$=9.1 Hz, 1 H), 8.22 (d, $^3$J$_{H,H}$=8.4 Hz, 1H, 2-H), 8.23 (d, $^3$J$_{H,H}$=9.3 Hz, 1H), 8.23 (d, $^3$J$_{H,H}$=9.1 Hz, 1H), 8.34 (d, $^3$J$_{H,H}$=7.6 Hz, 2H, 6-H, 8-H), 8.35 (d, $^3$J$_{H,H}$=8.4 Hz, 1H, 3-H), 8.82 (d, $^3$J$_{H,H}$=9.3 Hz, 1H), 10.78 (br. s, 1H, NH) ppm. 13C NMR (101 MHz, aceton-d$_6$): δ (ppm)=122.5 (CH), 125.2 (C$_q$), 125.4 (CH), 125.9 (C$_q$), 126.0 (CH), 126.7 (CH), 126.9 (CH), 127.0 (C$_q$) 127.6 (CH), 128.2 (CH), 128.8 (CH), 129.1 (C$_q$) 129.2 (CH), 131.7 (C$_q$), 131.8 (C$_q$), 132.2 (C$_q$) ppm. CF$_3$ and CO signals were not detected due to low intensities. $^{19}$F NMR (376 MHz, aceton-d$_6$): δ (ppm)=−75.7 (s, CF$_3$) ppm. C$_{18}$H$_{10}$F$_3$NO (313.0714) HR-MS (ESI): found 314.0783 [M+H]$^+$; calcd. 314.0787.

2,2,2-Trifluoro-N-[3,6,8-tris(bromo)pyren-1-yl]-acetamide (12)

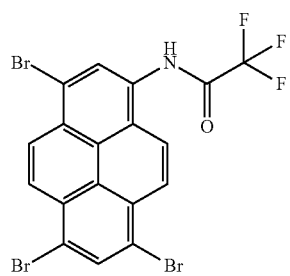

12

N-Trifluoroacetyl-1-aminopyrene 11 (870 mg, 2.76 mmol) was suspended in nitrobenzene (30 mL) and stirred at 50° C. for 30 min. Bromine (500 μL, 19.5 mmol, 7.07 eq.), dissolved in nitrobenzene (5 mL), was added to the solution of pyrene. The reaction mixture was stirred in a closed vessel at 80° C. for 30 min. Afterwards, the mixture was allowed to reach rt. After diluting with cyclohexane (20 mL), the precipitate was removed by filtration, washed with cyclohexane (2×25 mL) and dried in vacuo. The product was obtained as a light yellow powder (1224 mg, 2.26 mmol, 81%). $^1$H NMR (400 MHz, DMSO-d$_6$): δ=8.39 (d, $^3J_{H,H}$=9.7 Hz, 1H, 10-H), 8.47 (d, $^3J_{H,H}$=9.7 Hz, 1H, 9-H), 8.51 (d, $^3J_{H,H}$=9.3 Hz, 1H, 5-H), 8.59 (d, $^3J_{H,H}$=9.3 Hz, 1H, 4-H), 8.66 (s, 1H, 2-H), 8.80 (s, 1H, 7-H) ppm. $^{19}$F NMR (376 MHz, DMSO-d$_6$): δ=−73.57 (s, CF$_3$). MS (ESI): m/z (negative mode, %)=548 (100) [M]$^-$. HR-MS (ESI): calcd. for C$_{18}$H$_7$NOF$_3$$^{79}$Br$_2$$^{80}$Br ([M−H]$^-$) 547.7937, found 547.7930.

2,2,2-Trifluoro-N-[3,6,8-tris[(3-hydroxypropyl) sulfanyl]pyren-1-yl]-acetamide (14)

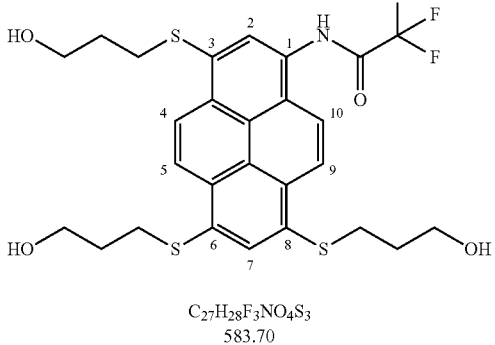

C$_{27}$H$_{28}$F$_3$NO$_4$S$_3$
583.70

K$_2$CO$_3$ (221.2 mg, 400 μmol, 0.53 eq.) and NEt$_3$ (40 μL) were suspended in dry DMF (4 mL) and flushed with argon for 15 min. 3-Mercapto-1-propanol (d=1.067 mg/mL, 272 μL, 290 mg, 3160 μmol, 4.35 eq.), brominated pyrene derivative 12 (400 mg, 757 μmol) and dry DMF (40 mL) were added, and a gentle argon stream was bubbled through the solution for 20 min. Afterwards, Pd$_2$(dba)$_3$ (197.6 mg, 216 μmol, 0.30 eq.) and Xantphos (140.4 mg, 242.8 μmol, 0.33 eq.) were added. The mixture was stirred at 85° C. under argon for 18 h. The solvents were removed in vacuo, the residue was dissolved in MeOH, applied to Celite® and submitted to flash chromatography (SNAP Ultra 100 g cartridge, DCM/MeOH with 2-18% MeOH-gradient over 15 CV) to provide the title compound 14 (298 mg, 511 μmol, 70%) as a pale-yellow solid. This procedure has been repeated several times on various scales and reliably gave 50-70% yields of the title product. $^1$H NMR (400 MHz, DMSO-d$_6$): δ=1.80 (m, 6H, CH$_2$CH$_2$CH$_2$), 3.28 (m, 6H, SCH$_2$CH$_2$), 3.55 (m, 6H, HOCH$_2$CH$_2$), 4.63 (m, 3H, OH), 8.06 (d, $^3J_{H,H}$=9.47 Hz, 1H, 9-H), 8.17 (br. s, 2H, 2-H, 7-H), 8.50 (d, $^3J_{H,H}$=9.47 Hz, 1H, 9-H), 8.53 (d, $^3J_{H,H}$=9.50 Hz, 1H, 5-H), 8.53 (d, $^3J_{H,H}$=9.50 Hz, 1H, 4-H), 11.85 (s, NH, 1H) ppm. 13C NMR (101 MHz, DMSO-d$_6$): δ=29.9 (CH$_2$), 30.0 (CH$_2$), 31.7 (CH$_2$), 31.9 (CH$_2$), 32.0 (CH$_2$), 59.2 (CH$_2$), 59.2 (CH$_2$), 59.2 (CH$_2$), 116.2 (d, $^1J_{F,C}$=289.3 Hz), 121.8 (CH), 123.2 (CH), 123.7 (CH), 124.2 (CH), 124.4 (C$_q$), 124.6 (C$_q$), 124.7 (C$_q$), 125.5 (CH), 127.2 (CH), 127.4 (C$_q$), 127.6 (CH), 128.6 (2×C$_q$), 132.3 (C$_q$), 132.8 (C$_q$), 132.9 (C$_q$), 156.2 (d, $^2J_{C,F}$=36.7 Hz) ppm.

$^{19}$F NMR (376 MHz, DMSO-d$_6$): δ=−73.15 (s, CF$_3$) ppm. HPLC: t$_R$=8.3 min (MeCN/H$_2$O 50:50→100:0+0.1% TFA in 25 min detected at 254 nm). HR-MS (ESI) Calcd. for C$_{27}$H$_{28}$NOF$_3$S$_3$ ([M−H]$^-$) 582.1060, found 582.1049.

2,2,2-Trifluoro-N-[3,6,8-tris[(3-hydroxypropyl) sulfonyl]pyren-1-yl]-acetamide (13a)

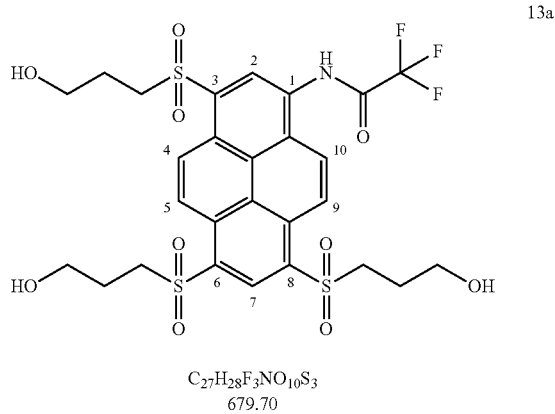 [SMILES: O=C(Nc1cc(S(=O)(=O)CCCO)c2ccc3c(S(=O)(=O)CCCO)cc(S(=O)(=O)CCCO)c4ccc1c2c43)C(F)(F)F]

C$_{27}$H$_{28}$F$_3$NO$_{10}$S$_3$
679.70

Triol 14 (135 mg, 232 μmol) was suspended in a mixture of AcOH (20 mL) and H$_2$O (1 mL). Afterwards, sodium tungstate dihydrate (19.1 mg, 57.9 μmol, 0.25 eq.) was added, and the solution was cooled with an ice-bath until the mixture became viscous. Then aq. H$_2$O$_2$ solution (85-90%, d=~1.45, 5.00 mL, ~189 mmol, ~82 eq.) was added over a period of 10 min. The solution was stirred for 30 min in the ice-bath. After removing the ice-bath, the mixture was stirred for 2 at rt, until the reaction was complete (TLC). The solvents were removed by freeze-drying, and the residue was dissolved in MeCN/H$_2$O. Celite® was added and, after removing all solvents in vacuo, the sample was submitted to flash chromatography (SNAP Ultra 25 g cartridge, ACN/MeOH+5% DCM with MeOH 1-10%-gradient over 20 CV). The isolated compound 13a was obtained as a yellow solid (113 mg, 116 μmol, 50%). $^1$H NMR (400 MHz, DMSO-d$_6$): δ)=1.78 (m, 6H, CH$_2$CH$_2$CH$_2$), 3.41 (m, 6H, HOCH$_2$CH$_2$), 3.73 (m, 6H, SCH$_2$CH$_2$), 4.59 (m, 3H, OH), 8.83 (d, $^3J_{H,H}$=9.46 Hz, 1H, 10-H), 9.02 (s, 1H, 2-H), 9.26 (s, 1H, 7-H), 9.35 (m, 2H, 4-H, 4-H), 9.47 (d, $^3J_{H,H}$=9.46 Hz, 1H, 9-H), 12.35 (s, NH, 1H) ppm. 13C NMR (101 MHz, DMSO-d$_6$): δ=25.7 (CH$_2$), 25.9 (CH$_2$), 53.2 (CH$_2$), 53.3 (CH$_2$), 53.5 (CH$_2$), 58.4 (CH$_2$), 58.4 (CH$_2$), 115.91 (d, $^1J_{F,C}$=289.0 Hz), 124.3 (CH), 124.8 (CH), 125.0, 125.3, 127.3, 127.9, 128.0, 128.1, 129.5 (CH), 131.1 (CH), 132.1 (CH), 132.2, 132.3, 134.5 (CH), 156.5 (t, $^2J_{C,F}$=38.2 Hz) ppm. $^{19}$F NMR (376 MHz, DMSO-d$_6$): δ=−73.46 (s, CF$_3$) ppm. TLC (SiO$_2$): R$_f$=0.68 (ACN:DCM:H$_2$O=10:1:1). HR-MS (ESI): Calcd. for C$_{27}$H$_{28}$NO$_{10}$F$_3$S$_3$ ([M−H]$^-$) 678.0755, found 678.0756.

3,6,8-Tris[(3-hydroxypropyl)sulfonyl]-pyrene-1-amine (13b)

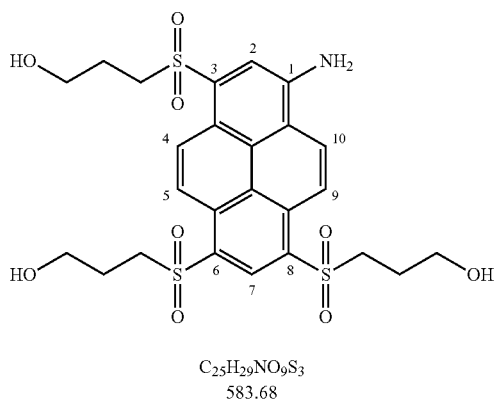

C$_{25}$H$_{29}$NO$_9$S$_3$
583.68

Protected pyrene derivative 13a (20 mg, 29 µmol) was suspended in MeOH (6 mL). Diluted aq. Na$_2$CO$_3$ (750 µL of the sat. aq. Na$_2$CO$_3$-solution mixed with 5 mL H$_2$O) was added, and the solution was stirred for 30 min at rt, followed by 30 min at 50° C. and 90 min at rt. Celite® and MeOH were added and the solvents were removed under reduced pressure. The crude product was purified by fcc (SNAP Ultra 10 g cartridge, DCM/MeOH with 2-20% MeOH-gradient over 12 CV), and the title product 13b was isolated as an orange solid (14 mg, 24 µmol, 81%). $^1$H NMR (400 MHz, DMSO-d$_6$): δ (ppm)=1.73 (m, 6H, CH$_2$C$\underline{\text{H}}_2$CH$_2$), 3.45 (m, 6H, OC$\underline{\text{H}}_2$CH$_2$), 3.51 (m, 6H, SC$\underline{\text{H}}_2$CH$_2$), 4.60 (m, 3H, O$\underline{\text{H}}$), 8.25 (s, 1H, 2-H), 7.83 (br. s, 2H, NH$_2$), 8.77 (d, $^3J_{H,H}$=9.56 Hz, 1H), 8.87 (d, $^3J_{H,H}$=9.66 Hz, 1H), 8.93 (d, $^3J_{H,H}$=9.66 Hz, 1H), 9.02 (s, 1H), 9.15 (d, $^3J_{H,H}$=9.56 Hz, 1H) ppm. 13C NMR (101 MHz, DMSO-d$_6$): δ=25.9, 26.0, 26.1, 52.3, 52.5, 53.4, 58.5, 58.5, 58.6, 115.8, 115.9, 116.9, 118.5, 121.0, 126.1, 126.4, 127.3, 127.9, 128.0, 128.8, 130.0, 132.8, 134.1, 136.9, 148.5 ppm. HPLC: t$_R$=13.1 min (MeCN/H$_2$O 10:90→100:0+0.1% TFA in 25 min detected at 225 nm). TLC (SiO$_2$) R$_f$=0.38 (DCM:MeOH=9:2). HR-MS (ESI): Calcd. for C$_{25}$H$_{29}$NO$_9$S$_3$ ([M−H]$^-$) 582.0932, found 582.0927. UV-VIS (In MeOH): ε=21000 M$^{-1}$ cm$^{-1}$, λ$_{max}$ (absorption)=486 nm, λ$_{max}$ (florescence)=534 nm, QY=0.80.

Tri-O-phosphorylated 3,6,8-tris[(3-hydroxypropyl) sulfonyl]-pyrene-1-amine (15)

C$_{25}$H$_{32}$NO$_{18}$P$_3$S$_3$
823,00

A solution of the deprotected pyrene derivative 13b (2.00 mg, 3.43 µmol) in trimethylphosphate (0.2 mL) was added dropwise to freshly distilled and ice-cooled POCl$_3$ (0.25 mL, 2.69 mmol) under argon atmosphere. The mixture was stirred at 0° C. for 30 min and 4 h at room temperature. All volatile components were distilled in vacuo (0.7 mbar) into a flask cooled in a dry ice/acetone bath (first at room temperature, later heating until 60° C.) and the residue was further dried by lyophilization (0.02 mbar). An aqueous Et$_3$N—H$_2$CO$_3$ buffer (1 M, ca. 6-8 mL) was added to the residue until the pH is adjusted to 8 (gas evolution). The sample was concentrated to a volume of ca 1 mL by freeze-drying and purified by preparative HPLC (Kinetex 5 µm EVO C18 100 A 250×21 mm column, MeCN/water+ 0.05 M TEAB, with MeCN-gradient 10-30% over 20 min, peak at 9.1 min).

$^1$H NMR (400 MHz, CD$_3$OD): δ=1.24 (t, 36H, J=7 Hz, 12 C$\underline{\text{H}}_3$, 3 Et$_3$N) 2.04 (m, 6H, CH$_2$C$\underline{\text{H}}_2$CH$_2$), 3.58-3.72 (m, 6H, Ar—SO$_2$C$\underline{\text{H}}_2$CH$_2$), 3.07 (q, J=7 Hz, 24H, C$\underline{\text{H}}_2$CH$_3$, 3 Et$_3$N), 3.88-3.93 (m, 6H, CH$_2$C$\underline{\text{H}}_2$SO$_3$), 8.17 (s, 1H), 8.73 (d, J=9.5 Hz, 1H), 8.73 (d, J=9.5 Hz, 1H), 8.86 (d, J=9.5 Hz, 1H), 9.18 (s, 1H) 9.21 (d, J=9.5 Hz, 1H), ppm.

$^{13}$C NMR (101 MHz, CD$_3$OD): δ=9.2 (CH$_3$), 21.6 (CH$_2$), 22.1 (CH$_2$), 25.8 (CH$_2$), 47.4 (CH$_2$), 54.1 (CH$_2$), 55.3 (CH$_2$), 56.5 (CH$_2$), 63.8 (CH$_2$), 71.0 (CH$_2$), 71.6 (CH$_2$), 117.8 (C), 118.3 (CH), 120.2 (CH), 122.9 (CH), 127.7 (C), 128.2 (C), 128.7 (CH), 129.3 (C), 129.8 (C), 130.2 (CH), 131.8 (CH), 134.8 (C), 136.0 (C), 138.3 (C), 149.8 (C), ppm. $^{31}$P NMR (161.9 MHz, CD$_3$OD): δ=0.97 ppm (s, OP(O)(OH)$_2$))

HPLC: t$_R$=5.48 min (MeCN/H$_2$O 10:90→100:0+0.05 M TEAB in 20 min detected at 254 nm). TLC (RP—SiO$_2$ C18): R$_f$=0.7-0.8 (MeCN:H$_2$O+0.05 M TEAB=9:2). MS (ESI): Calcd. for C$_{25}$H$_{32}$NO$_{18}$P$_3$S$_3$ (822.9994): [M−H]$^-$ 821.9922. UV-VIS (0.05 M aq. Et$_3$N*H$_2$CO$_3$ (TEAB) buffer, pH 8-8.5): λ$_{max}$ (absorption)=203, 236, 305, 477 nm; λ$_{max}$ (emission)=542 nm, ε=19600 M$^{-1}$ cm$^{-1}$, QY$_{fl.}$=92% (absolute value in a TEAB buffer, pH 8-8.5, as measured by Hamamatsu apparatus C11347-12 with an integration sphere) and 74-76%, respectively, as measured with a Fluorolog-3 spectrometer with an R2658 PMT, relative to an alkaline solution of fluorescein as a standard, whose QY$_{fl.}$=90% in a 0.1M NaOH under excitation at 496 nm).

N-[3,6,8-Tris[(3-hydroxypropyl) sulfonyl]pyren-1-yl]glycine (16)

3,6,8-Tris[(3-hydroxypropyl) sulfonyl]pyrene-1-(methylamine) (18)

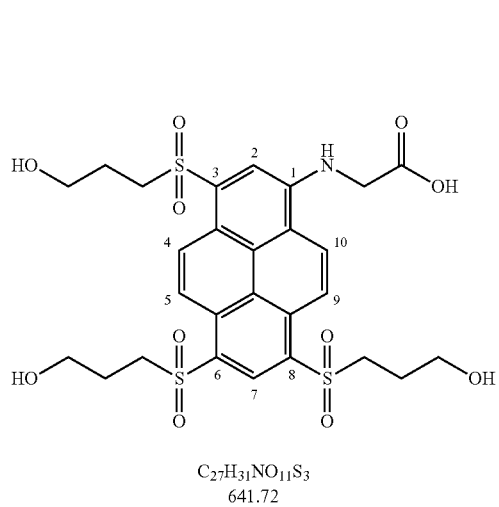

$C_{27}H_{31}NO_{11}S_3$
641.72

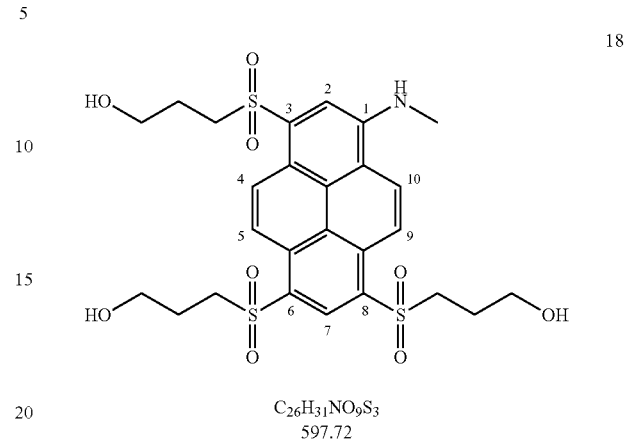

$C_{26}H_{31}NO_9S_3$
597.72

The deprotected amino pyrene 13b (19 mg, 34 µmol) was suspended in MeOH (11 mL). Glyoxylic acid monohydrate (12.6 mg, 136 µmol, 4.0 eq.) was added, and the mixture was acidified by addition of conc. HCl (12 µL, 140 µmol, 4.3 eq.). After 1 h stirring at rt, NaBH$_3$CN (17 mg, 270 µmol, 8.0 eq.) was added. After 3 h, another portion of glyoxylic acid monohydrate (11 mg, 120 µmol, 3.5 eq.) was added. After stirring overnight, a second portion of NaBH$_3$CN (29 mg, 460 µmol, 14 eq.) and conc. HCl (20 µL, 240 µmol, 7.1 eq.) were added. After stirring for one more day at rt, a third portion of glyoxylic acid monohydrate (91 mg, 990 µmol, 29 eq.), NaBH$_3$CN (27 mg, 430 µmol, 12.6 eq.) and conc. HCl (20 µL, 240 µmol, 7.1 eq.) were added, and the reaction was stirred for one night. The solvent was removed in vacuo, and the crude product was purified by RP-column chromatography with H$_2$O/ACN+0.2% TFA with 9-25%-ACN gradient. The product was isolated as a red solid (8.3 mg, 13 µmol, 38%).

$^1$H NMR (400 MHz, DMSO-d$_6$): δ=1.74 (m, 6H, CH$_2$CH$_2$CH$_2$), 3.38 (m, 6H, SCH$_2$CH$_2$), 3.63 (m, 6H, HOCH$_2$CH$_2$), 4.26 (br. s, 2H, CH$_2$COOH), 4.59 (m, 3H, OH), 7.89 (br. s, 1H, NH) 8.45 (m, 2H, 4-H, 5-H), 8.81 (d, $^3J_{H,H}$=9.46 Hz, 1H, 10-H), 8.89 (s, 1H, 2-H), 9.06 (s, 1H, 7-H), 9.21 (d, $^3J_{H,H}$=9.46 Hz, 1H, 9-H) ppm. TLC (SiO$_2$) R$_f$=0.22 (ACN:H$_2$O:DCM+formic acid=20:2:1).

HPLC: t$_R$=4.4 min (MeCN/H$_2$O 30:70→100:0+0.1% TFA in 25 min detected at 254 nm). HPLC: t$_R$=9.5 min (MeCN/H$_2$O 10:90→100:0+0.1% TFA in 25 min detected at 465 nm). MS (ESI): m/z (negative mode, %)=641 (100) [M]$^-$. HR-MS (ESI): Calcd. for C$_{27}$H$_{31}$NO$_{11}$S$_3$ ([M+Na]$^+$) 664.0951, found 664.0925. UV-VIS (In MeOH): ε=18000 M$^{-1}$ cm$^{-1}$, λ$_{max}$. (absorption)=499 nm, λ$_{max}$. (fluorescence)=553 nm, QY=0.71.

Compound 14 (75 mg, 0.13 mmol) was suspended in dry DMF (0.1 mL) under argon, Cs$_2$CO$_3$ (55 mg, 0.17 mmol) was added followed by MeI (0.15 mL). The reaction mixture was stirred for 1 h in a screw-cap tube at 50° C. HPLC indicated that the reaction was complete. HPLC: starting material t$_R$=13.7 min (MeCN/H$_2$O 30:70→100:0+0.1% TFA in 25 min detected at 254 nm). HPLC: product t$_R$=15.8 min (MeCN/H$_2$O 30:70→100:0+0.1% TFA in 25 min detected at 254 nm). DMF was removed under vacuum, and the residue was taken up in dichloromethane-water mixture. The organic layer was separated, washed with brine, dried over sodium sulfate, filtered and evaporated in vacuo. Compound 17 (56 mg, 78%, the N-methylated product, see the general scheme of the synthesis for structure) was isolated by chromatography on SiO$_2$ (25 g) in the course of elution with 0-5% MeOH in ethyl acetate. To oxidize it into the sulfone, compound 17 was dissolved in acetic acid (5 mL), water was added (3 mL), followed by Na$_2$WO$_4$*2H$_2$O (12 mg, catalyst), and the mixture was cooled to 0° C. Hydrogen peroxide (1.5 mL of a ca. 80% solution) was added at 0° C. The reaction mixture turned dark, and then the dark color disappeared. HPLC indicated complete conversion to a new substance with t$_R$=8.48 min (MeCN/H$_2$O 30:70→100:0+0.1% TFA in 25 min detected at 254 nm). All volatile materials were removed in vacuo, and the dry residue was dissolved in aqueous acetonitrile. The cleavage of the CF$_3$CO group (deprotection) in the intermediate compound was performed as follows: a saturated aqueous solution of Na$_2$CO$_3$ (ca. 20 wt.-%, 1.5 mL) was added, and the solution was stirred at room temperature. The ratio acetonitrile-water has to be chosen in such a way, that the addition of 1.5 mL of saturated aqueous Na$_2$CO$_3$ solution will provide a homogeneous reaction mixture. The reaction mixture turns to be bright orange in several minutes; it was stirred overnight at room temperature. HPLC indicated complete conversion to a new substance (title compound) with t$_R$=6.4 min (MeCN/H$_2$O 30:70-100:0+0.1% TFA in 25 min detected at 254 nm). Sodium carbonate was neutralized by addition of glacial AcOH, and the frozen reaction mixture was lyophilized. The solid residue was dissolved in hot aqueous acetonitrile and applied onto a column with RP—SiO$_2$ (C18, 50 g). Elution with acetonitrile-water mixture (1/3-1/2, +1% AcOH) resulted first in a green-yellow "band" of impurity, followed by an orange zone of the title compound (17). Lyophilization of the orange solution afforded 48 mg (80%) of the title compound as an orange-red powder (slightly soluble in methanol and water). HPLC: $t_R$=6.0 min (MeCN/H$_2$O 30:70→100:0+0.1% TFA in 20 min detected at 254 nm; Kinetex column). $^1$H NMR (400 MHz, CD$_3$OD+DMSO-d$_6$, ref. 3.30 ppm for CHD$_2$OD): δ=1.92 (m, 6H, CH$_2$C$\underline{H}_2$CH$_2$), 3.28 (s, 3H, MeNH), 3.57 (q, 6H, $^3J_{H,H}$=6.1 Hz, OC$\underline{H}_2$CH$_2$), 3.68 (m, 6H, SO$_2$C$\underline{H}_2$CH$_2$), 8.12 (s, 1H, 2-H), 8.89 (d, $^3J_{H,H}$=9.6 Hz, 1H), 8.93 (d, $^3J_{H,H}$=9.6 Hz, 1H), 9.10 (d, $^3J_{H,H}$=9.6 Hz, 1H), 9.22 (s, 1H), 9.32 (d, $^3J_{H,H}$=9.7 Hz, 1H) ppm. HR-MS (ESI): C$_{26}$H$_{31}$NO$_9$S$_3$ (597.1116); [M–H]$^-$ found 596,1078, calc. 596.1088. UV-VIS (MeOH): ε=23400 M$^{-1}$ cm$^{-1}$, λ$_{max.}$ (absorption)=502 nm, λ$_{max.}$ (fluorescence)=550 nm, QY=0.88. UV-VIS (H$_2$O): ε=19500 M$^{-1}$ cm$^{-1}$, λ$_{max.}$ (absorption)=509 nm, λ$_{max.}$ (fluorescence)=563 nm, QY=0.88.

Some Additional Selected Fluorescent Dyes with Large Negative Net Charges and Favorable Spectral Properties (See Also Scheme 12 and Table 2).

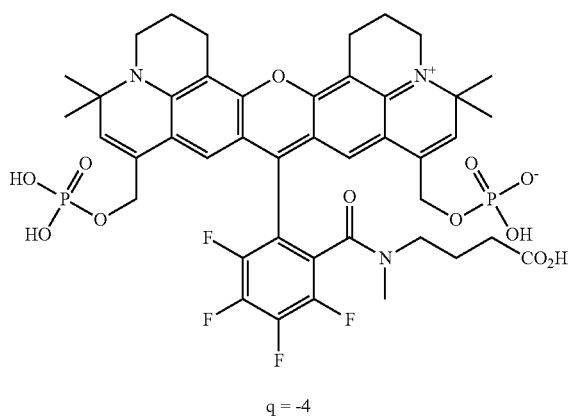

19 q = -4

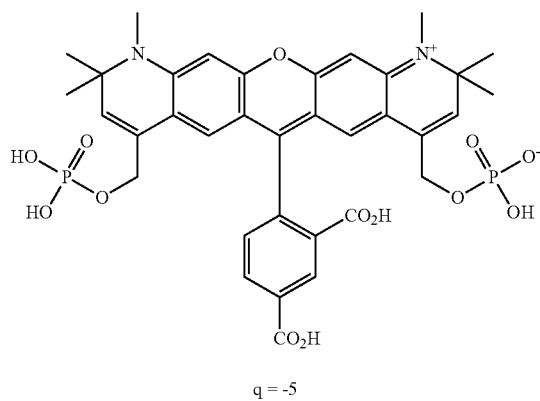

20 q = -5

The red-emitting rhodamine dye with multiple ionizable groups of structure 20 was obtained by phosphorylation of the corresponding hydroxyl-substituted rhodamine precursor and isolated analogously to compound 19 (another phosphorylated rhodamine dye, see Schemes 6 and 11 above) previously described by K. Kolmakov, C. A. Wurm, R. Hennig, E. Rapp, S. Jakobs, V. N. Belov and S. W. Hell in *Chem. Eur. J.* 2012, 18, 12986-12998 (see compound 7-H therein for the properties and the phosphorylation details). The hydroxyl-substituted precursor for compound 20 was synthesized according to K. Kolmakov, C. A. Wurm, D. N. H. Meineke, F. Göttfert, V. P. Boyarskiy, V. N. Belov and S. W. Hell (*Chem. Eur. Journal,* 2013, 20, 146-157; see compound 14-Et therein). The phosphorylation was followed by saponification of the ethyl ester group via a routine procedure, as described.

Purity and identity of compound 20 was confirmed by the following analytical data: $^1$H NMR (400 MHz, DMSO-d$_6$): δ=1.23 (s, 6H, CH$_3$), 1.28 (s, 6H, CH$_3$), 2.62 (s, 6H, NCH$_3$), 4.21 (m, 4H, 2CH$_2$), 5.70 (s, 2H), 6.76 (s, 2H), 7.16-7.30 (br. m, 4H), 8.55 (m, 1H), 8.36 (m, 1H) ppm. $^{13}$C NMR (101 MHz, DMSO-d$_6$): δ=29.1 (CH$_3$), 34.2 (CH$_3$), 95.8 (CH$_2$), 118.2 (CH), 121.7 (C) 122.6 (C), 125.5 (CH), 127.3 (CH), 127.4 (CH), 128.0 (CH), 129.8 (CH), 133.9 (C), 136.8 (C), 155.0 (CO), 157.0 (CO) ppm.

$^1$H NMR (400 MHz, CD$_3$OD, 20 as a Et$_3$N-salt): δ=1.12 (t, J=7 Hz, 9H, C$\underline{H}_3$CH$_2$), 1.25 (t, J=7 Hz, 27H, C$\underline{H}_3$CH$_2$), 1.52 (s, 6H, CH$_3$), 1.53 (s, 6H, CH$_3$), 3.11, 3.31 (m, 24H, CH$_3$C$\underline{H}_2$), 3.18 (s, 6H, NCH$_3$), 3.61 (m, 2H, CH$_2$), 4.45 (m, 2H, C$\underline{H}_2$), 6.03 (s, 2H), 6.8 (s, 2H), 6.9 (s, 2H), 7.28 (d, J=8 Hz, 1H), 8.16 (d, J=8 Hz, 1H), 8.66 (m, 1H) ppm. $^{31}$P NMR (161.9 MHz): δ=–0.2 (DMSO-d$_6$) and 0.63 (CD$_3$OD) ppm (s, OP(O)(OH)$_2$)).

HPLC: $t_R$=3.9 min (Kinetex EVO C-18 column, with 0.02 M aq. Et$_3$N (A) and 3% MeCN (B), isocratic flow 0.5 mL/min, detection at 254 nm). TLC: R$_f$=0.25 (silica gel plates, MeCN/H$_2$O 5:1+0.2% Et$_3$N).

HR-MS (ESI): calc. for C$_{35}$H$_{35}$N$_2$O$_{13}$P$_2^-$ ([M–H]$^-$) 753.1614, found 753.1672. A red-violet highly water-soluble dye with a very intense red fluorescence: UV-VIS (PBS buffer, pH=7.4) λ$_{max.}$ abs.=582 nm, λ$_{max.\,fl.}$=609 nm, ε=120000 M$^{-1}$ cm$^{-1}$, QY$_{fl.}$=0.76% (abs. value in TEAB buffer, excitation at 540 nm).

3,6,8-Tris[(3-sulfopropyl)sulfonyl]-pyrene-1-amine (23a)

The synthesis of a sulfoalkylsulfonyl-substituted 1-aminopyrene derivative 23a and of its homolog 23b involved halogen exchange in the tribromo-substituted precursor 12 (see Scheme 11 above) with synthones containing SH and SO$_3$H functions and was followed by oxidation to the sulfone.

2,2,2-Trifluoro-N-[3,6,8-tris[(3-sulfopropyl) sulfanyl]pyrene-1-yl]-acetamide (21a)

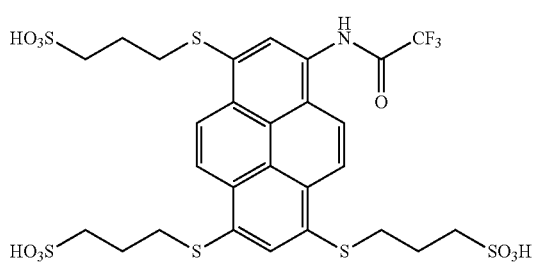

21a 2,2,2-trifluoro-N-[3,6,8-tris(bromo)pyren-1-yl]-acetamide (tribromo-substituted precursor 12, 180 mg, 0.33 mmol; for preparation and properties see above) and sodium 3-mercapto-1-propanesulfonate (600 mg, 3.37 mmol, 10 equiv) was reacted in dry DMF (20 mL) at 90° C. upon stirring under an argon atmosphere in presence of triethylamine (0.6 mL) as a base with $Pd_2(dba)_3$ (20 mg, 0.02 mmol) and xantphos reagent (30 mg, 0.05 mmol) as catalysts. As the reaction completed (3-5 h), the crude product (Na salt of 21a) was first purified over reversed-phase silica gel (C-18) and $H_2O$—MeCN (gradient 0-70%) as mobile phase. The homogeneous fractions were combined, filtered (syringe filters 0.45 μm), concentrated and freeze-dried. The additional purification of the crude product (340 mg, containing inorganic salts) was performed by repeated preparative HPLC using Kinetex Gemini NX C-18 solid phase (5 μm) with 50 mmol TEAB buffer (A) and MeCN (B) under gradient (0-20% B) conditions. The pure fractions were combined, concentrated at t≤40° C. and freeze-dried to furnish 70-80% of the yellow crystalline water-soluble solid as a triethylammonium salt of compound 21a.

Analytical data: $^1H$ NMR (400 MHz, DMSO-$d_6$): δ=1.08 (m, 27H, $CH_3CH_2$) 1.98 (m, 6H, $CH_2CH_2CH_2$), 2.66 (m, 6H, $SCH_2CH_2$), 2.88 (m, 18H, $CH_2CH_3$), 3.39 (m, 6H, $O_3SCH_2CH_2$), 8.13 (d, J=9.5 Hz, 1H), 8.15 (d, J=9.5 Hz, 1H), 8.26 (br. s, 1H), 8.45 (d, J=9.5 Hz, 1H), 8.48 (d, J=9.5 Hz, 1H), 8.52 (s, 2H) ppm. $^1H$ NMR (400 MHz, $CD_3OD$): δ=1.21 (t, J=7 Hz, 27H, $CH_3CH_2$) 2.15 (m, 6H, $CH_2CH_2CH_2$), 2.99 (m, 6H, $SCH_2CH_2$), 3.10 (q, J=7 Hz, 18H, $CH_2CH_3$), 3.38 (m, 6H, $O_3SCH_2CH_2$), 8.06 (d, J=9.5 Hz, 1H), 8.22 (s, 1H), 8.31 (s, 1H), 8.43 (d, J=9.5 Hz, 1H), 8.51 (br. s, 1H, NH), 8.63-8.70 (m, 2H) ppm.

$^{13}C$ NMR (101 MHz, DMSO-$d_6$): δ=9.4 ($CH_3$), 22.5 ($CH_2$), 25.0 ($CH_2$), 25.1 ($CH_2$), 32.3 ($CH_2$), 32.4 ($CH_2$), 45.7 ($CH_2$), 50.0 ($CH_2$), 115.3 (CH), 118.2 (CH), 122.3 (CH), 123.1 (CH), 123.4 (CH), 124.3 (C), 124.8 (CH), 124.9 (C), 125.5 (CH), 127.2 (C), 127.3 (C), 127.7 (C), 127.9 (C), 132.0 (C), 132.1 (C), 156.3 (C), 156.6 (C), 171.0 (CO) ppm. $^{19}F$ NMR (376 MHz, DMSO-$d_6$): δ=−73.20 (s, $CF_3$) ppm.

HPLC: $t_R$=8.2 min (Kinetex column EVO C-18 100, 5 μm, 4.6×250 mm), 0.05 M aq. TEAB (A) and 25% MeCN (B), isocratic flow 0.5 mL/min, detection at 254 nm). TLC: $R_f$=0.6 (silica gel plates, MeCN/$H_2O$ 7:1+0.2% $Et_3N$, also seen by its intense blue fluorescence under illumination with UV-light at 365 nm). HR-MS (ESI): calc. for $C_{27}H_{27}F_3NO_{10}S_6^-$ ([M–H]$^-$) 773.9911, found 773.9845.

UV-VIS (PBS buffer, pH=7.4) $λ_{max}$. (absorption)=428 nm. The synthesis is based on the general recipe for palladium-catalized cross-coupling of thiols and aryl bromides described by C. Mispeleare-Canivet and co-workers, Tetrahedron 2005, 61, 5253-5259.

2,2,2-Trifluoro-N-[3,6,8-tris[(3-sulfopropyl) sulfonyl]pyrene-1-yl]-acetamide (22a)

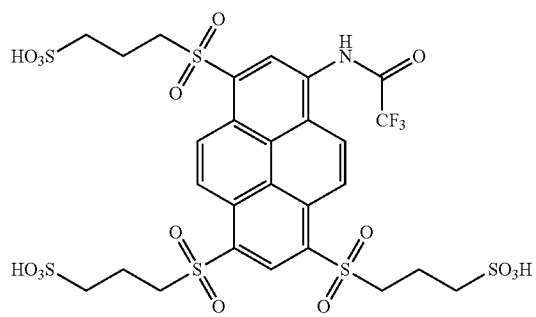

22a

The thioether 21a (as a triethylammonium salt) was oxidized to the sulfone as follows: 50 mg (0,046 mmol, as a $Et_3N$ salt with M=1077) of the substrate was dissolved in a mixture of HOAc (4 mL) and water (0.4 mL). Upon cooling to +5° C. 1 ml of 50 wt. % $H_2O_2$ and 0.5 mL of 1 wt. % aq. solution of $Na_2WO_4 \times 2H_2O$ (a catalyst) was added. The reaction mixture was kept for 30 min at this temperature, left overnight at RT, diluted with water (20 mL) and freeze-dried. The product was purified by means of preparative HPLC using Kinetex Gemini NX C-18 solid phase (5 μm) with 0.5 vol. % aqueous HOAc (A) and MeCN (B) under gradient (0-50% B) conditions. The pure fractions were pooled, concentrated at t≤40° C. and freeze-dried to furnish 28 mg (52%) of a red crystalline solid as a triethylammonium salt (M.W.=1173), which has an intense yellow-orange fluorescence in water.

Analytical data for compound 22a: $^1H$ NMR (400 MHz, $CD_3OD$): δ=1.27 (m, 27H, $CH_3CH_2$) 2.24 (m, 6H, $CH_2CH_2CH_2$), 2.97 (m, 6H, $SO_2CH_2CH_2$), 3.19 (m, 18H, $CH_2CH_3$), 3.84 (m, 6H, $CH_2CH_2SO_3$), 8.73 (d, J=9 Hz, 1H), 9.03 (s, 1H), 9.39-9.41 (m, 2H), 9.02 (s, 1H), 9.52 (d, J=9 Hz, 1H) ppm. $^{13}C$ NMR (101 MHz, $CD_3OD$): δ=8.9 ($CH_3$), 20.1 ($CH_2$), 47.9 ($CH_2$), 50.2 ($CH_2$), 55.7 ($CH_2$), 56.2 ($CH_2$), 56.6 ($CH_2$), 126.4 (C), 126.6 (CH), 127.0 (C), 128.0 (CH), 129.6 (CH), 130.0 (C), 131.7 (C), 133.5 (C), 134.1 (C), 134.4 (C), 134.9 (C), 136.4 (C), 158.8 (C=O), ppm. $^{19}F$ NMR (376 MHz, $CD_3OD$): δ=−76.50 (s, $CF_3$) ppm.

HPLC: $t_R$=5.2 min (Kinetex column EVO C-18 100, with 0.05 M aq. TEAB (A) and 25% MeCN (B), isocratic flow 0.5 mL/min, detection at 254 nm). TLC: $R_f$=0.5 (silica gel plates, MeCN/$H_2O$ 7:1+0.2% $Et_3N$, seen by its intense orange fluorescence under illumination with UV-light at 365 nm). HR-MS (ESI): calc. for $C_{27}H_{27}F_3NO_{16}S_6^-$ ([M–H]$^-$) 869.9606, found 869.9536. UV-VIS (PBS buffer, pH=7.4) $λ_{max}$ abs.=476 nm.

3,6,8-Tris[(3-sulfopropyl)sulfonyl]-pyrene-1-amine (23a)

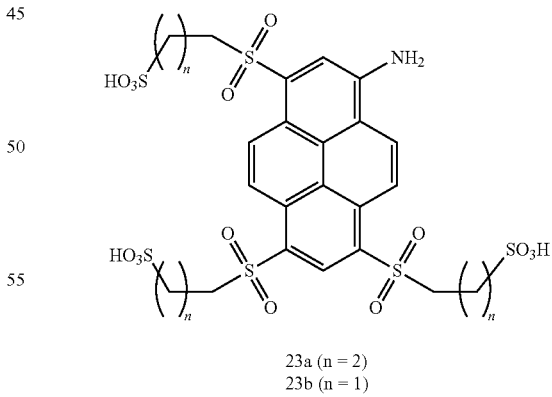

23a (n = 2)
23b (n = 1)

The protective $COCF_3$ group in compound 22a was cleaved by a conventional method under basic conditions at RT (see T. W Greene, P. G. M. Wuts "Protective groups in organic synthesis" Third Edition 1999, p. 557). The reaction progress was monitored by TLC, the reaction mixture neutralized to pH 7-8 with HOAc and concentrated at t≤40° C.

The residue was subjected to preparative HPLC using Gemini NX C-18 solid phase (5 μm) with 0.3 vol. % aqueous Et₃N (A) and 10% MeCN (B) under isocratic mode. The pure fractions were concentrated and freeze-dried to furnish 22 mg (79%) of compound 23a as a triethylammonium salt. Properties: red crystalline solid, well-soluble in water to give solutions with a very intense yellow-greenish fluorescence.

Analytical data: $^1$H NMR (400 MHz, CD₃OD): δ=1.27 (t, 27H, J=7 Hz, C$\underline{H}_3$CH₂, 3 Et₃N) 2.13-2.29 (m, 6H, CH₂C$\underline{H}_2$CH₂), 2.88-3.17 (m, 6H, Ar—SO₂C$\underline{H}_2$CH₂), 3.16 (q, J=7 Hz, 18H, C$\underline{H}_2$CH₃, 3 Et₃N), 3.69-3.84 (m, 6H, CH₂C$\underline{H}_2$SO₃), 8.13 (s, 1H), 8.66 (d, J=9 Hz, 1H), 8.83 (d, J=9 Hz, 1H), 8.93 (d, J=9 Hz, 1H), 9.17 (d, J=9 Hz, 1H), 9.20 (s, 1H) ppm. $^{13}$C NMR (101 MHz, CD₃OD) δ=9.2 (CH₃), 20.0 (CH₂), 20.1 (CH₂), 20.2 (CH₂), 47.9 (CH₂), 50.4 (CH₂), 55.4 (CH₂), 55.7 (CH₂), 56.5 (CH₂), 60.1 (CH₂), 117.7 (C), 118.3 (CH), 120.3 (CH), 123.0 (CH), 127.7 (C), 128.1 (C), 128.6 (CH), 129.4 (C), 129.9 (C), 130.2 (CH), 131.7 (CH), 134.9 (C), 136.0 (C), 138.1 (C), 149.6 (C), ppm. HPLC: $t_R$=4.7 m n (Kinetex column EVO C-18 100, with 0.05 M aa. TEAB (A) and 25% MeCN (B), isocratic, 0.5 mL/min, detection at 254 nm). TLC: $R_f$=0.4 (silica gel plates, MeCN/H₂O 7:1+0.2% Et₃N, seen by its intense green fluorescence under illumination with UV-light at 365 nm). HR-MS (ESI) negative mode: calc. for $C_{25}H_{28}NO_{15}S_6^-$ ([M–H]$^-$) 774.9873, found 774.9804; positive mode: calc. for $C_{25}H_{33}N_2O_{15}S_6$+([M+NH₄]$^+$) 793, 0205, found 793.0146. UV-VIS (TEAB buffer, pH=8.5): ε=21 000 M$^{-1}$ cm$^{-1}$, $\lambda_{max}$. abs.=486 nm, $\lambda_{max}$. fl.=542 nm., $\Phi_{fl}$=86% (in TEAB buffer, relative to fluorescein as a reference dye with $\Phi_{fl}$=0.9 in 0.1 M NaOH under excitation at 496 nm).

Using the commercially available sodium 2-mercaptoethanesulfonate as a thiol-containing reagent with a shorter alkyl chain, the dye 23b (a homolog of dye 23a depicted above, which also belongs to the general Formula C with each X═SO₃H and n=1) was obtained in the exactly same fashion and with a high yield from bromide 12. Its spectral and photophysical properties (ε, $\lambda_{max}$ and $\Phi_{fl}$, see also Table 2) proved to be fully identical to those of the dye 23a.

Example 3

Reductive Amination of Glycans

For reductive amination of glycans using the compounds of the present invention, the prior art protocol for fluorescent labeling of N-glycans with 8-aminopyrene-1,3,6-trisulfonic acid trisodium salt (APTS) and a borane-based reducing agent (Bigge J C, Patel T P, Bruce J A, Goulding P N, Charles S M, Parekh R B, *Analytical Biochemistry* 1995, 230, 229-238; Ruhaak L R, Hennig R, Huhn C, Borowiak M, Dolhain RJEM, Deelder A M, Rapp E, Wuhrer M, *Journal of Proteome Research* 2010, 9, 6655-6664) or a modified version thereof may be followed.

The invention claimed is:

1. A fluorescent dye having multiple ionizable and/or negatively charged groups which is selected from the group consisting of compounds of the following general Formula B or of salts thereof:

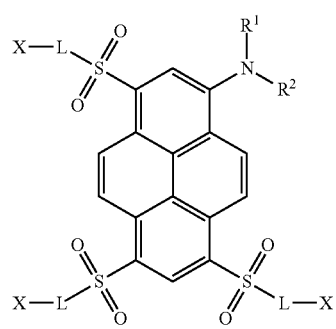

Formula B wherein R$^1$ and/or R$^2$ are independent from each other and may represent:

H, deuterium (D), alkyl or deutero-substituted alkyl;

R$^1$-R$^2$ may form a four-, five-, six-, or seven-membered non-aromatic carbocycle with an additional primary amino group NH₂, secondary amino group NHR$^a$, where R$^a$=C₁-C₆ alkyl, or hydroxyl group OH attached to one carbon atom of this carbocycle; or R$^1$-R$^2$ may form a four-, five-, six-, or seven-membered non-aromatic heterocycle with an additional heteroatom included in the heterocycle;

a hydroxyalkyl group (CH₂)$_m$OH, where m=1-12, with a straight or branched alkyl chain;

one of R$^1$ or R$^2$ groups may be a carbonate or carbamate derivative (CH₂)$_m$OCOOR$^4$ or (CH₂)$_m$NHCOOR$^4$, where m=1-12 and R$^4$=methyl, ethyl, 2-chloroethyl, N-succinimidyl, sulfo-N-succinimidyl, 1-oxybenzotriazolyl, a phenyl group or a substituted phenyl group;

(CH₂)$_m$NR$^a$R$^b$, where m=1-12, with a straight or branched alkyl chain; R$^a$, R$^b$ are independent from each other and may be H, or optionally substituted C₁-C₄ alkyl group(s);

one of R$^1$ or R$^2$ groups may be a primary amino group to form aryl hydrazines Ar-NR$^6$NH₂ where Ar is the entire pyrene residue in Formula B and R$^6$=H or alkyl;

one of R$^1$ or R$^2$ groups may be a hydroxy group to form aryl hydroxylamines Ar-NR$^7$OH where Ar is an entire pyrene residue in Formula B and R$^7$=H or alkyl;

one of R$^1$ or R$^2$ groups may be an alkyloxyamino group (CH₂)$_n$ONH₂ with n=1-12;

one of R$^1$ or R$^2$ groups may be CO(CH₂)$_n$COOR, with n=1-5 and a straight or branched alkyl chain (CH₂)n and with R$^8$ selected from H, straight or branched C₁-C₆ alkyl, CH₂CN, 2- and 4-nitrophenyl, 2,3,5,6-tetrafluorophenyl, pentachlorophenyl, pentafluoro-phenyl, N-succinimidyl, sulfo-N-succinimidyl, 1-oxybenzo-triazolyl;

further, one of R$^1$ or R$^2$ may be (CH₂)$_n$CONHR$^9$, with n=1-5 and R$^9$=H, C₁-C₆ alkyl, (CH₂)$_m$N₃, (CH₂)$_m$—N-maleimido, (CH₂)$_m$—NHCOCH₂X (X═Br or I), where m=2-6 and with straight or branched alkyl chains in (CH₂)n and R$^9$; or one of R$^1$ or R$^2$ may represent CH₂—C₆H₄—NH₂, COC₆H₄—NH₂, CONHC₆H₄—NH₂ or CSNHC₆H₄—NH₂ with C₆H₄ being a 1,2-, 1,3- or 1,4-phenylene, COC₅H₃N—NH₂ or CH₂—C₅H₃N—NH₂ with C₅H₃N being pyridin-2,4-diyl, pyridin-2,5-diyl, pyridin-2,6-diyl, or pyridin-3,5-diyl; or one of R$^1$ or R$^2$ may be an alkyl azide (CH)N₃ or alkine;

wherein linker L may be divalent or polyvalent and comprises at least one carbon atom and may represent alkyl, heteroalkyl, perfluoroalkyl, alkyloxy, single or multiple difluoromethyl ($CF_2$), and alkene or alkine moieties in any combinations, at any occurrence, linear or branched, with a length ranging from $C_1$ to $C_{12}$;

the linker L may also include a carbonyl ($CH_2CO$, $CF_2CO$) moiety, also as a part of an amide group; or the linker L may also comprise or contain a residue of 1,3,5-triazine, thus providing two attachment points for group X;

X denotes a solubilizing and/or ionizable anion-providing moiety, further, the anion-providing moiety is optionally linked through non-aromatic O, N and S-containing heterocycles, or, alternatively, one of the groups X optionally bears any of the moieties listed above for groups $R^1$ and $R^2$, also with any type of linkage listed for group L, and independently from other substituents;

with the proviso that in all compounds represented by Formula B three or six negatively charged groups are present in the residues X of Formula B under basic conditions, and the negatively charged groups represent at least partially deprotonated residues of ionizable groups selected from the following: OH, SH, COOH, $SO_3H$, $OSO_3H$, $OP(O)(OH)_2$, $OP(O)(OH)R^a$, where $R^a = C_1-C_4$ alkyl or substituted $C_1-C_4$ alkyl, $P(O)(OH)_2$, and $P(O)(OH)R^a$, where $R^a = C_1-C_4$ alkyl or substituted $C_1-C_4$ alkyl.

2. The fluorescent dye according to claim 1, wherein X at each occurrence represents 1 to 4 groups $SO_3H$ attached to the respective linker group L at one or more sites.

3. The fluorescent dye according to claim 1 having Formula C and at least one alkyl sulfonyl group

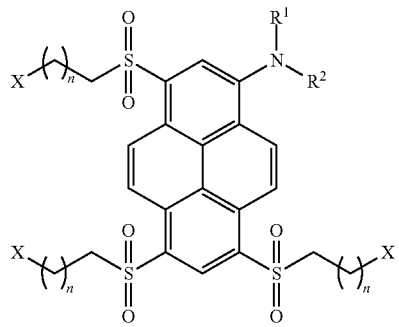

Formula C or a salt thereof,
wherein
n=1-12;
$R^1$ and/or $R^2$ are independent from each other and may represent:

H, deuterium (D), alkyl or deutero-substituted alkyl;

$R^1$-$R^2$ may form a four-, five, six-, or seven-membered non-aromatic carbocycle with an additional primary amino group $NH_2$, secondary amino group $NHR^a$, where $R^a = C_1-C_6$ alkyl, or hydroxyl group OH attached to one carbon atom of this carbocycle; or $R^1$-$R^2$ may form a four-, five-, six-, or seven-membered non-aromatic heterocycle with an additional heteroatom included in the heterocycle;

a hydroxyalkyl group $(CH_2)_mOH$, where m=2-12, with a straight or branched alkyl chain;

one of $R^1$ or $R^2$ groups may be a carbonate or carbamate derivative $(CH_2)_mOCOOR^4$ or $(CH_2)_mNHCOOR^4$, where m=1-12 and $R^4$=methyl, ethyl, 2-chloroethyl, N-succinimidyl, sulfo-N-succinimidyl, 1-oxybenzotriazolyl, a phenyl group or a substituted phenyl group;

$(CH_2)_mNR^aR^b$, where m=2-12, with a straight or branched alkyl chain; $R^a$, $R^b$ are independent from each other and may be H, or optionally substituted $C_1-C_4$ alkyl group(s);

one of $R^1$ or $R^2$ groups may be a primary amino group to form aryl hydrazines, as described for Formula B;

one of $R^1$ or $R^2$ groups may be a hydroxy group to form aryl hydroxylamines, as described for Formula B;

one of $R^1$ or $R^2$ groups may be an alkyloxyamino group $(CH_2)_nONH_2$ with n=1-12;

one of $R^1$ or $R^2$ may be $(CH_2)_nCONHR^6$, with n=1-12, and $R^6$=H, $C_1-C_6$ alkyl, $(CH_2)_mN_3$, $(CH_2)_m$—N-maleimido, $(CH_2)_m$—$NHCOCH_2X$ (X=Br or I), where m=2-6 and with straight or branched alkyl chains in $(CH_2)n$ and $R^6$; or one of $R^1$ or $R^2$ may represent $CH_2$—$C_6H_4$—$NH_2$, $COC_6H_4$—$NH_2$, $CONHC_6H_4$—$NH_2$ or $CSNHC_6H_4$—$NH_2$ with $C_6H_4$ being a 1,2-, 1,3- or 1,4-phenylene, $COC_5H3N$—$NH_2$ or $CH_2$—$C_5H_3N$—$NH_2$ with $C_5H_3N$ being pyridin-2,4-diyl, pyridin-2,5-diyl, pyridin-2,6-diyl, or pyridin-3,5-diyl;

the $(CH_2)n$—$CH_2$ linker, with n=1-12, between the $SO_2$ fragment and the residue X in Formula B may represent a straight-chain, branched or cyclic group having 2-6 carbon atoms;

X=SH, COOH, $SO_3H$, $OSO_3H$, $OP(O)(OH)_2$, $OP(O)(OH)R^a$, where $R^a$=optionally substituted $C_1-C_4$ alkyl, $P(O)(OH)_2$, $P(O)(OH)R^a$, where $R^a$=optionally substituted $C_1-C_4$ alkyl;

with the proviso that in all compounds represented by Formula C three or six negatively charged groups are present in the residues X of Formula C under basic conditions, and the negatively charged groups represent at least partially deprotonated residues of ionizable groups selected from the following: OH, SH, COOH, $SO_3H$, $OSO_3H$, $OP(O)(OH)_2$, $OP(O)(OH)R^a$, where $R^a = C_1-C_4$ alkyl or substituted $C_1-C_4$ alkyl, $P(O)(OH)_2$, and $P(O)(OH)R^a$, where $R^a = C_1-C_4$ alkyl or substituted $C_1-C_4$ alkyl.

4. The fluorescent dye according to claim 2, wherein X at each occurrence is $SO_3H$ and n is 1-12.

5. The fluorescent dye according to claim 3 one of Formula B or C, wherein $R^1$ and/or $R^2$ in Formula B or C represents H, deuterium (D), alkyl or deutero-substituted alkyl, wherein one, several or all H atoms in the alkyl group may be replaced by deuterium atoms, 4,6-dihalo-1,3,5-triazinyl ($C_3N_3X_2$) where X is halogen, 2-, 3- or 4-aminobenzoyl ($COC_6H_4NH_2$), N-[(2-, N-[(3- or N-[(4-aminophenyl)ureido group ($NHCONHC_6H_4NH_2$), N-[(2-, N-[(3- or N-[(4-aminophenyl)thioureido group ($NHCSNHC_6H_4NH_2$) or linked carboxylic acid residues and their reactive esters of the general formulae $(CH_2)_{m1}COOR^3$, $(CH_2)_{m1}OCOOR^3$, $(CH_2)_{n1}COOR^3$ or $(CO)_{m1}(CH_2)_{m2}(CO)_{n1}(NH)_{n2}(CO)_{n3}(CH_2)_{n4}COOR^3$ where the integers m1, m2 and n1, n2, n3, and n4 independently range from 1 to 12 and from 0 to 12, respectively, with the linked carboxylic acid residues and their respective esters being straight, branched, saturated, unsaturated, partially or completely deuterated, and/or included into a carbo- or heterocycle containing N, O or S, whereas $R^3$ is H, D or a nucleophile-reactive leaving group.

6. The fluorescent dye according to claim 1 that has a hydroxylamine or a hydrazine moiety as an analyte-reactive group, which is connected directly with a dye core or where the hydroxylamine, hydrazine or sulfonyl hydrazide moieties are connected via a linker group.

7. The fluorescent dye according to claim 1 having one of the following formulae:

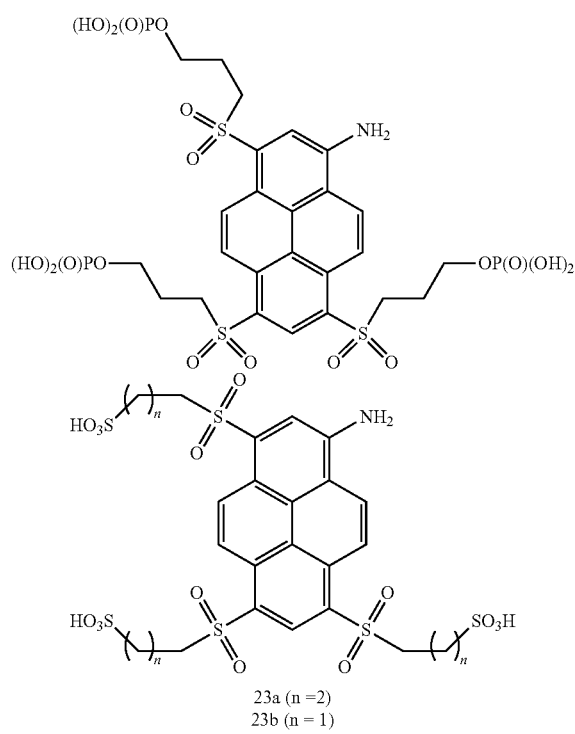

23a (n = 2)
23b (n = 1)

or a salt thereof.

8. The fluorescent dye according to claim 3 having Formula B or C which has a net charge z of 0, −1, −3, −6 or −12.

9. The fluorescent dye according to any one of claims 1, 6 or 8, which is a salt comprising negatively charged sulfonate and/or phosphate groups and counterions selected from inorganic or organic cations, and/or comprising a positively charged group or a charge-transfer complex formed at the nitrogen site $N(R^1)R^2$ in the dye of formula B or C with a counterion selected from anions of a strong mineral, organic or a Lewis acid.

10. The fluorescent dye according to any one of claims 1, 6, or 8, wherein carbohydrate-reactive groups, are connected to the nitrogen site $N(R^1)R^2$ in the dye of formula B or C via all types of linkers listed for group L in formula B.

11. The fluorescent dye according to any one of claims 1, 6 or 8 and salts thereof for use in a reductive amination and in a condensation with reducing sugars.

12. The fluorescent dye according to any one of claims 1, 6 or 8 and salts thereof for use as a fluorescent label for amino acids, peptides, proteins, including primary and secondary antibodies, single-domain antibodies, docetaxel, avidin, streptavidin and their modifications, aptamers, nucleotides, nucleic acids, toxins, lipids, carbohydrates, including 2-deoxy-2-amino glucose and other 2-deoxy-2-aminoaminopyranosides, glycans, biotin, and other small molecules having molecular masses of less than 1500 Da.

13. The fluorescent dye according to claim 12 belongs to the following compound set: 13a, 13b, 16 and 18

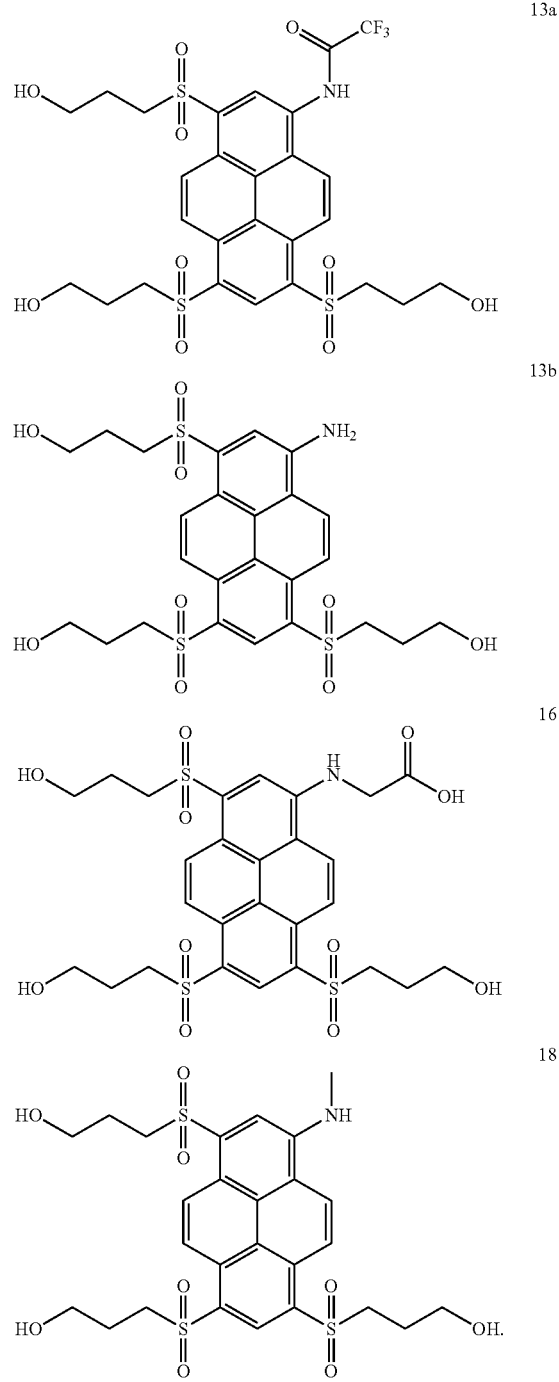

14. A method of using the fluorescent dye according to any one of claims 1, 6 or 8 and salts thereof as fluorescent reagents for conjugation to analytes, wherein the method comprises a conjugation step comprising forming at least one covalent chemical bond or at least one molecular complex with a chemical entity or substance.

15. Carbohydrate-dye conjugates comprising the fluorescent dye according to any one of claims 1, 6 or 8.

16. The carbohydrate-dye conjugates according to claim 15 wherein the fluorescent dye is selected from the compounds shown below:

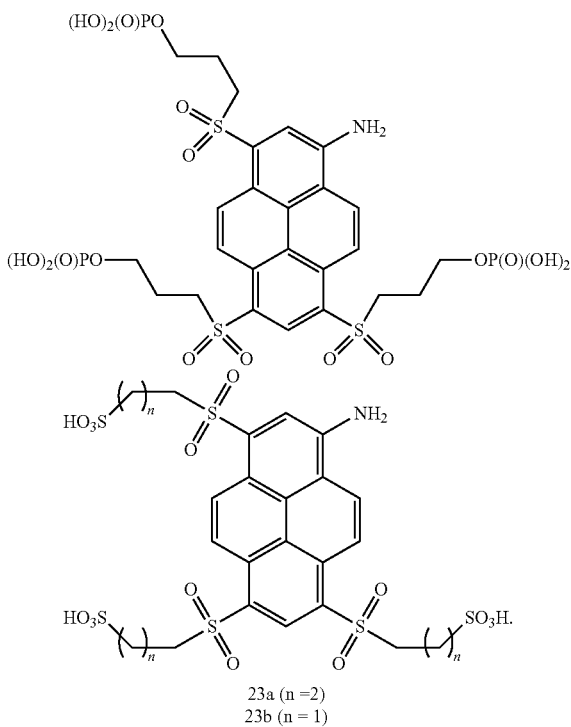

23a (n =2)
23b (n = 1)

17. A kit or composition comprising one or more of the fluorescent dye of claims 1, 6 or 8.

18. A method for synthesizing fluorescent aminopyrene dyes with an absorbance maxima of 477-510 nm, a net charge of 0 or down to −6, and an emission maxima of 535-560 nm in water, said method comprising an exchange reaction of an aryl halogen to a substituted thioalkyl function, followed by oxidation to a sulfone and, optionally, by phosphorylation at the hydroxyl site, wherein the fluorescent aminopyrene dyes have the general formula B or of salts thereof:

Formula B

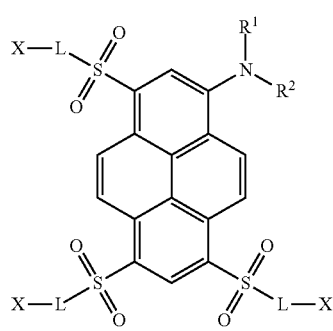

wherein $R^1$ and/or $R^2$ are independent from each other and may represent:

H, deuterium (D), alkyl or deutero-substituted alkyl;
$R^1$-$R^2$ may form a four-, five-, six-, or seven-membered non-aromatic carbocycle with an additional primary amino group $NH_2$, secondary amino group $NHR^a$, where $R^1$ =$C_1$-$C_6$ alkyl, or hydroxyl group OH attached to one carbon atom of this carbocycle; or $R^1$-$R^2$ may form a four-, five-, six-, or seven-membered non-aromatic heterocycle with an additional heteroatom included in the heterocycle;
a hydroxyalkyl group $(CH_2)_mOH$, where m=1-12, with a straight or branched alkyl chain;
one of $R^1$ or $R^2$ groups may be a carbonate or carbamate derivative $(CH_2)_mOCOOR^4$ or $(CH_2)_mNHCOOR^4$, where m=1-12 and $R^4$=methyl, ethyl, 2-chloroethyl, 1V-succinimidyl,
sulfo-N-succinimidyl, 1-oxybenzotriazolyl, a phenyl group or a substituted Phenyl group;
$(CH_2)_mNR^aR^b$, where m=1-12, with a straight or branched alkyl chain; $R^a$, $R^b$ are independent from each other and may be H or optionally substituted $C_1$-$C_4$ alkyl group(s);
one of $R^1$ or $R^2$ groups may be a primary amino group to form aryl hydrazines Ar-$NR^6NH_2$ where Ar is the entire pyrene residue in Formula B and $R^6$=H or alkyl;
one of $R^1$ or $R^2$ groups may be a hydroxy group to form aryl hydroxylamines Ar-$NR^7OH$ where Ar is an entire pyrene residue in Formula B and $R^7$=H or alkyl;
one of $R^1$ or $R^2$ groups may be an alkyloxyamino group $(CH_2)_nONH$ with n=1-12;
one of $R^1$ or $R^2$ groups may be $CO(CH_2)_nCOOR^8$, with n=1-5 and a straight or branched alkyl chain $(CH_2)_n$ and with $R^8$ selected from H, straight or branched $C_1$-$C_6$ alkyl, $CH_2CN$, 2- and 4-nitrophenyl, 2,3,5,6-tetrafluorophenyl, pentachlorophenyl, pentafluoro-phenyl, N-succinimidyl, sulfo-N-succinimidyl, 1-oxybenzo-triazolyl;
further, one of $R^1$ or $R^2$ may be $(CH_2)_nCONHR^9$, with n=1-5 and $R^9$ =H, $C_1$-$C_6$ alkyl, $(CH_2)_mN_3$, $(CH_2)_m$—N-maleimido, $(CH_2)_mNHCOCH_2X$ (X=Br or I), where m=2-6 and with straight or branched alkyl chains in $(CH_2)n$ and $R^9$; or
one of $R^1$ or $R^2$ may represent $CH_2$-$C_6H_4$—$NH_2$, $COC_6H_4$—$NH_2$, $CONHC_6H_4$—$NH_2$ or $CSNHC_6H_4$—$NH_2$ with $C_6H_4$ being a 1,2-, 1,3- or 1,4-phenylene, $COC_5H_3N$—$NH_2$ or $CH_2$-$C_4H_3N$—$NH_2$ with $C_5H_3N$ being pyridin-2,4-diyl, pyridin-2,5-diyl, pyridin-2,6-diyl, or pyridin-3,5-diyl; or one of $R^1$ or $R^2$ may be an alkyl azide $(CH)N_3$ or alkine;
wherein linker L may be divalent or polyvalent and comprises at least one carbon atom and may represent alkyl, heteroalkyl, perfluoroalkyl, alkyloxy, single or multiple difluoromethyl ($CF_2$), and alkene or alkine moieties in any combinations, at any occurrence, linear or branched, with a length ranging from $C_1$ to $C_{12}$;
the linker L may also include a carbonyl ($CH_2CO$, $CF_2CO$) moiety, also as a tart of an amide group; or
the linker L may also comprise or contain a residue of 1,3,5-triazine, thus providing two attachment points for group X;
X denotes a solubilizing, and/or ionizable anion-providing moiety,
further, the anion-providing moiety is optionally linked through non-aromatic O, N and S-containing heterocycles, or, alternatively, one of the groups X optionally bears any of the moieties listed above for groups $R^1$ and $R^2$, also with any type of linkage listed for group L, and independently from other substituents;
with the proviso that in all compounds represented by Formula B three or six negatively charged groups are present in the residues X of Formula B under basic conditions, and the negatively charged groups represent at least partially deprotonated residues of ionizable groups selected from the following: OH, SH, COOH, $SO_3H$, $OSO_3H$, $OP(O)(OH)_2$, $OP(O)(OH)R^a$, where $R^a=C_1-C_4$ alkyl or substituted $C_1-C_4$ alkyl, $P(O)(OH)_2$, and $P(O)(OH)R^a$, where $R^a=C_1-C_4$ alkyl or substituted $C_1-C_4$ alkyl, or wherein the fluorescent aminopyrene dues have the general formula C:

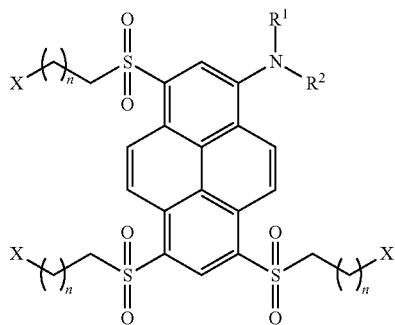

Formula C or a salt thereof,
wherein
n=1-12;
$R^1$ and/or $R^2$ are independent from each other and may represent;
H, deuterium (D), alkyl or deutero-substituted alkyl;
$R^1$-$R^2$ may form a four-, five, six-, or seven-membered non-aromatic carbocycle with an additional primary amino group $NH_2$, secondary amino group $NHR^a$, where $R^a = C_1-C_6$, alkyl, or hydroxyl group OH attached to one carbon atom of this carbocycle; or
$R^1$-$R^2$ may form a four-, five-, six-, or seven-membered non-aromatic heterocycle with an additional heteroatom included in the heterocycle;
a hydroxyalkyl group $(CH_2)_mOH$, where m=2-12, with a straight or branched alkyl chain,
one of $R^1$ or $R^2$ groups may be a carbonate or carbamate derivative $(CH_2)_mOCOOR^4$ or $(CH_2)_mNHCOOR^4$, where m=1-12 and $R^4$=methyl, ethyl, 2-chloroethyl, N4-succinimidyl, sulfo-N-succinimidyl, 1-oxybenzotriazolyl, a phenyl group or a substituted phenyl group;
$(CH_2)_mNR^aR^b$, where in m=2-12, with a straight or branched alkyl chain, $R^a$, $R^b$ are independent from each other and may be H, or optionally substituted $C_1-C_4$ alkyl group(s);

one of $R^1$ or $R^2$ groups may be a primary amino group to form aryl hydrazines, as described for Formula B;
one of $R^1$ or $R^2$ groups may be a hydroxy group to form aryl hydroxylamines, as described for Formula B;
one of $R^1$ or $R^2$ groups may bean alkyloxyamino group $(CH_2)_nONH_2$ with n=1-12;
one of $R^1$ or $R^2$ may be $(CH_2)_nCONHR^6$, with n=1-12, and $R^6$=H, $C_1-C_6$ alkyl, $(CH_2)_mN_3$, $(CH_2)_m$—N-maleimido, $(CH_2)_m$—$NHCOCH_2X$ (X=Br or I), where m=2-6 and with straight or branched alkyl chains in $(CH_2)n$ and $R^6$; or
one of $R^1$ or $R^2$ may represent $CH_2-C_6H_4$—$NH_2$, $COC_6H_4$—$NH_2$, $CONHC_6H_4$—$NH_2$ or $CSNHC_6H_4$—$NH_2$ with $C_6H_4$ being a 1,2, 1,3- or 1,4-phenylene, $COC_5H_3N$—$NH_2$ or $CH_2$—$CH_2N$—$NH_2$ with $C_5H_3N$ being pyridin-2,4-diyl, pyridin-2,5-diyl, pyridin-2,6-diyl, or pyridin-3,5-diyl;
the $(CH_2)n$-$CH_2$ linker, with n=1-12, between the $SO_2$ fragment and the residue X in Formula B may represent a straight-chain, branched or cyclic group having 2-6 carbon atoms,
X=SH, COOH, $SO_3H$, $OSO_3H$, $OP(O)(OH)_2$, $OP(O)(OH)R^a$, where $R^a$=optionally substituted $C_1-C_4$ alkyl, $P(O)(OH)_2$, $P(O)(OH)R^a$, where $R^a$=optionally substituted $C_1-C_4$ alkyl;
with the proviso that in all compounds represented by Formula C three or six negatively charged groups are present in the residues X of Formula C under basic conditions, and the negatively charged groups represent at least partially deprotonated residues of ionizable groups selected from the following OH, SH, COOH, $SO_3H$, $OSO_3H$, $OP(O)(OH)_2$, $OP(O)(OH)R^a$, where $R^a = C_1-C_4$ alkyl or substituted $C_1-C_4$ alkyl, $P(O)(OH)_2$, and $P(O)(OH)R^a$, where $R^a=C_1-C_4$ alkyl or substituted $C_1-C_4$ alkyl.

19. A kit or composition comprising one or more of the carbohydrate-dye conjugates of claim 15.

20. The fluorescent dye according to claim 1, wherein X comprises a moiety selected from the group consisting of hydroxyalkyl $(CH_2)_nOH$, thioalkyl $((CH_2)_nSH)$, carboxy alkyl $((CH_2)_nCO_2H)$, alkyl sulfonate $((CH_2)_nSO_3H)$, alkyl sulfate $((CH_2)OSO_3H)$, alkyl phosphate $((CH_2)_nOP(O)(OH)_2)$ and phosphonate $((CH_2)_nP(O)(OH)_2)$, wherein n is an integer ranging from 0 to 12, or an analog thereof wherein one or more of the $CH_2$ groups are replaced by $CF_2$.

* * * * *